(12) United States Patent
Iida et al.

(10) Patent No.: US 10,188,469 B2
(45) Date of Patent: Jan. 29, 2019

(54) INSTRUMENT, MANIPULATOR SYSTEM, AND CONTROL METHOD OF INSTRUMENT

(71) Applicant: OLYMPUS CORPORATION, Tokyo (JP)

(72) Inventors: Masatoshi Iida, Tokyo (JP); Takumi Isoda, Tokyo (JP); Noriaki Yamanaka, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 632 days.

(21) Appl. No.: 14/722,654

(22) Filed: May 27, 2015

(65) Prior Publication Data

US 2015/0335388 A1 Nov. 26, 2015

Related U.S. Application Data

(63) Continuation of application No. PCT/JP2013/082649, filed on Nov. 28, 2013.
(Continued)

(51) Int. Cl.
*A61B 19/00* (2006.01)
*A61B 34/30* (2016.01)
(Continued)

(52) U.S. Cl.
CPC .............. *A61B 34/30* (2016.02); *A61B 34/37* (2016.02); *A61B 90/361* (2016.02);
(Continued)

(58) Field of Classification Search
CPC ...... A61B 18/1492; A61B 2017/00473; A61B 2018/1495; A61B 2090/0811;
(Continued)

(56) References Cited

U.S. PATENT DOCUMENTS 5,855,583 A 1/1999 Wang et al.
6,309,397 B1 10/2001 Julian et al.
(Continued)

FOREIGN PATENT DOCUMENTS

CN 101513360 A 8/2009
JP S62-028880 A 2/1987
(Continued)

OTHER PUBLICATIONS

International Search Report dated Mar. 11, 2014 issued in PCT/JP2013/082649.
(Continued)

*Primary Examiner* — Elizabeth Houston
*Assistant Examiner* — Mohamed Gabr
(74) *Attorney, Agent, or Firm* — Scully, Scott, Murphy & Presser, P.C.

(57) ABSTRACT

A manipulator system includes a medical instrument which is capable of being inserted into a body; a manipulator which is capable of holding the instrument; a holding detector which detects a holding state where the manipulator holds the instrument; an instruction-receiving part which detects an instruction for operating the instrument; and a controller which operates the instrument only in a case where the instruction-receiving part detects the instruction when the holding detector detects the holding state.

2 Claims, 40 Drawing Sheets

Related U.S. Application Data

(60) Provisional application No. 61/731,139, filed on Nov. 29, 2012, provisional application No. 61/732,637, filed on Dec. 3, 2012, provisional application No. 61/740,641, filed on Dec. 21, 2012.

(51) Int. Cl.
  *A61B 90/00* (2016.01)
  *A61B 34/37* (2016.01)
  *A61B 18/14* (2006.01)
  *A61B 17/00* (2006.01)
  *A61B 90/30* (2016.01)

(52) U.S. Cl.
  CPC ........... *A61B 18/1492* (2013.01); *A61B 90/30* (2016.02); *A61B 2017/00464* (2013.01); *A61B 2017/00473* (2013.01); *A61B 2018/1422* (2013.01); *A61B 2018/1495* (2013.01); *A61B 2090/0811* (2016.02); *F04C 2270/0421* (2013.01)

(58) Field of Classification Search
  CPC ......... A61B 34/30; A61B 34/37; A61B 90/30; A61B 90/361; F04C 2270/0421
  See application file for complete search history.

(56) References Cited

U.S. PATENT DOCUMENTS

| | | | |
|---|---|---|---|
| 7,083,571 B2 | 8/2006 | Wang et al. | |
| 8,303,576 B2 | 11/2012 | Brock | |
| 2002/0072736 A1 | 6/2002 | Tierney et al. | |
| 2002/0151784 A1* | 10/2002 | Mizoguchi | G02B 21/0012 600/407 |
| 2005/0228224 A1 | 10/2005 | Okada et al. | |
| 2005/0267335 A1 | 12/2005 | Okada et al. | |
| 2011/0208206 A1* | 8/2011 | Diamant | A61B 17/2202 606/128 |
| 2012/0239011 A1 | 9/2012 | Hyodo et al. | |
| 2014/0148819 A1* | 5/2014 | Inoue | A61B 17/29 606/130 |

FOREIGN PATENT DOCUMENTS

| | | |
|---|---|---|
| JP | 06-054801 A | 3/1994 |
| JP | 08-224248 A | 9/1996 |
| JP | H08-224245 A | 9/1996 |
| JP | H08-280709 A | 10/1996 |
| JP | 2002-017747 A | 1/2002 |
| JP | 2002-537884 A | 11/2002 |
| JP | 2003-284726 A | 10/2003 |
| JP | 2004-517659 A | 6/2004 |
| JP | 2004-248878 A | 9/2004 |
| JP | 2005-046361 A | 2/2005 |
| JP | 2005-296412 A | 10/2005 |
| JP | 2005-334237 A | 12/2005 |
| JP | 2006-135159 A | 5/2006 |
| JP | 2006-158977 A | 6/2006 |
| JP | 2007-143869 A | 6/2007 |
| JP | 2008-184763 A | 8/2008 |
| JP | 4271088 B | 6/2009 |
| JP | 2011-007257 A | 1/2011 |
| JP | 2011-148088 A | 8/2011 |
| JP | 2012-187311 A | 10/2012 |
| WO | 00/51486 A1 | 9/2000 |
| WO | 02/41782 A2 | 5/2002 |
| WO | 2005/110267 A1 | 11/2005 |

OTHER PUBLICATIONS

Japanese Office Action dated May 10, 2016 in related Japanese Patent Application No. 2015-527597.
Japanese Office Action dated Nov. 8, 2016 in related Japanese Patent Application No. 2015-527597.
Extended Supplementary European Search Report dated Nov. 8, 2016 in related European Patent Application No. 13 85 8131.9.
Chinese Office Action dated Jul. 9, 2018 in Chinese Patent Application No. 201380061286.8.

* cited by examiner

FIG. 41
FIRST MODE
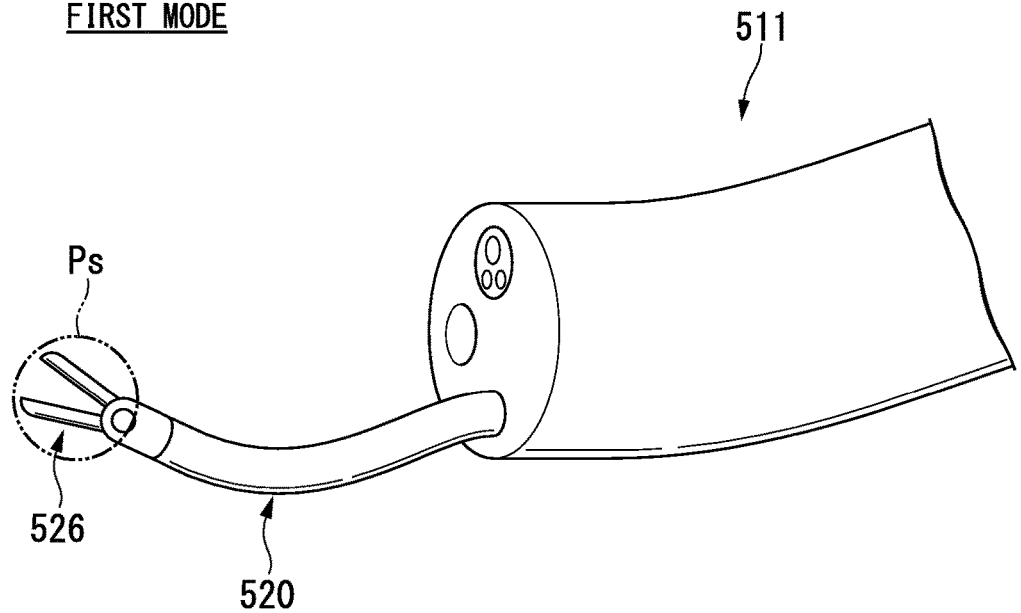
SECOND MODE
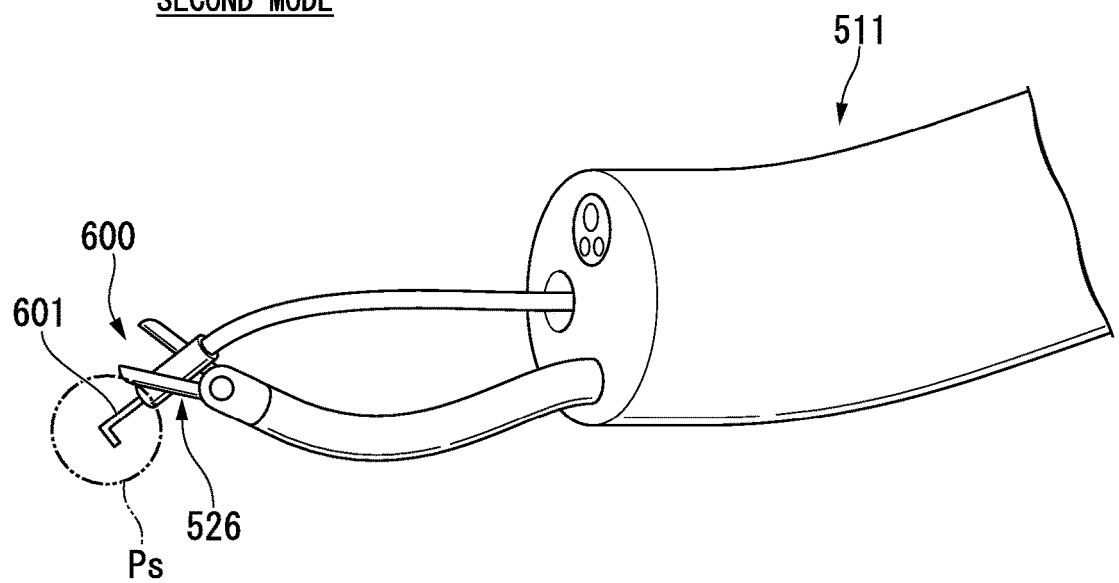

FIG. 43
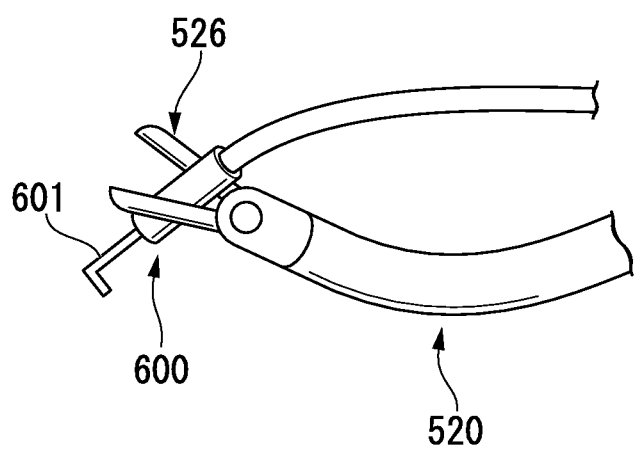
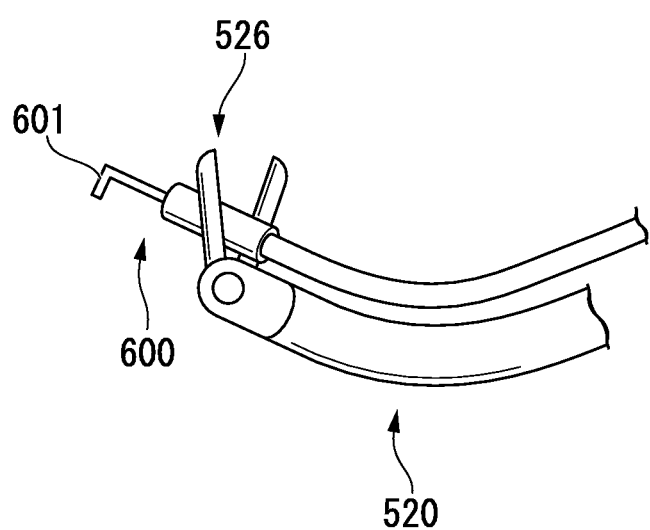

INSTRUMENT, MANIPULATOR SYSTEM, AND CONTROL METHOD OF INSTRUMENT

This application is a communication application based on PCT application No. PCT/JP2013/082649 filed on Nov. 28, 2013, whose priority is claimed on U.S. Patent Application No. 61/740,641 provisionally applied in the United States on Dec. 21, 2012, U.S. Patent Application No. 61/732,637 provisionally applied in the United States on Dec. 3, 2012, and U.S. Patent Application No. 61/731,139 provisionally applied in the United States on Nov. 29, 2012. The contents of both the PCT application and U.S. Provisional applications are incorporated herein by reference.

TECHNICAL FIELD

The present invention relates to an instrument used after being inserted into the body, a manipulator system equipped with the instrument, and a control method of the instrument.

BACKGROUND ART

In recent years, in order to cut back personnel in medical facilities, research into medical treatments using robots has been carried out. Particularly in the surgery field, various manipulator systems that perform treatments for patients by using manipulators having multi-degrees of freedom (multiple joints) are suggested. As such manipulator systems, a manipulator system is known that holds an instrument at a distal portion of a manipulator and can remotely operate this instrument.

For example, in a robot surgical procedure apparatus described in U.S. Pat. No. 6,309,397, a carriage can be operated from a console where an operator, such as a surgeon, is sitting. The console is provided with a master operation unit for operating the carriage and a display unit for displaying an image to be described below.

The carriage is configured so as to be movable and is installed on the side of a patient who receives a procedure. Generally, three manipulators are attached to the carriage. One manipulator among the three is provided with an image acquisition device, such as an endoscope. An instrument is connected to the remaining two manipulators. An image acquired by the image acquisition device is transmitted to the above console and displayed on the display unit. The respective manipulators are operable by the master operation unit.

In the instrument, an end effector is pivotably provided at a distal portion of a shaft. The end effector for attaching a clip is used. The end effector has a pair of finger elements that have dents formed in opposed surfaces. By arranging a clip in the dents, the clip can be reliably mounted on the end effector.

A procedure using the manipulator system configured in this way is performed as follows. In the following, particularly a treatment using the instrument will be described.

A plurality of cannulas are attached to the body wall of the patient. A cartridge to which a plurality of clips are attached is connected to a manipulator. The master operation unit is operated to drive the manipulator, and the cartridge to which the plurality of clips is attached is introduced into the body of the patient through one cannula. The end effector for clip mounting is introduced into the body of the patient through another cannula.

The end effector is operated from the outside of the body of the patient by a servo mechanism or a manual operation in order to mount a clip, and attaches the clip to a target tissue within the body. For example, by pressing the end effector against the cartridge, one of the clips in the cartridge is mounted on the end effector, and the clip is attached to another target tissue.

In this way, the end effector does not need to take a clip out of a body cavity once and introduce the clip into the body again in order to mount the clip.

SUMMARY OF THE INVENTION

According to a first aspect of the present invention, a manipulator system includes a medical instrument which is capable of being inserted into a body; a manipulator which is capable of holding the instrument; a holding detector which detects a holding state where the manipulator holds the instrument; an instruction-receiving part which detects an instruction for operating the instrument; and a controller which operates the instrument only in a case where the instruction-receiving part detects the instruction when the holding detector detects the holding state.

According to a second aspect of the present invention, in the above first aspect, the holding detector detects the holding state according to a conduction state and a cutoff state between a pair of contacts.

According to a third aspect of the present invention, in the above second aspect, the holding detector has a switch that is provided in the instrument and that switches the conduction state and the cutoff state between the pair of contacts by being pressed in a reference direction, and the manipulator may have a gripper that grips the switch.

According to a fourth aspect of the present invention, in the above third aspect, the instrument may have a first instrument and a second instrument. The controller may operate only the first instrument in a case where the instruction-receiving part detects the instruction when the holding detector detects a first holding state between the manipulator and the first instrument, and operate only the second instrument in a case where the instruction-receiving part detects the instruction when the holding detector detects a second holding state between the manipulator and the second instrument.

According to a fifth aspect of the present invention, in the above third aspect, the switch may have a first switch that switches a conduction state and a cutoff state between a pair of first contacts, and a second switch that switches a conduction state and a cutoff state between a pair of second contacts, the instrument may be provided with the first switch and the second switch, the controller may make the instrument perform a first operation in a case where the instruction-receiving part detects the instruction when the holding state is detected according to a conduction state or a cutoff state between the pair of first contacts, and may make the instrument perform a second operation different from the first operation in a case where the instruction-receiving part detects the instruction when the holding state is detected according to a conduction state or a cutoff state between the pair of second contacts.

According to a sixth aspect of the present invention, in the above first aspect, the holding detector may detect the holding state on the basis of an image in which the manipulator and the instrument are captured.

According to a seventh aspect of the present invention, a medical instrument is provided that is insertable into a body and operates in a state where the instrument is held by a manipulator within the body. The manipulator includes a holding detector that detects a holding state where the instrument is held.

According to an eighth aspect of the present invention, in the above seventh aspect, the instrument may further include a sheath which is formed by a material having flexibility; an extendable mechanism which is provided within the sheath, wherein a distal portion thereof moves to a distal side as an action portion provided on an outer surface thereof is moved to an axis side of the sheath; and a treatment part which is provided at the distal portion of the extendable mechanism.

According to a ninth aspect of the present invention, in the above eighth aspect, the holding detector has a switch that is provided in the instrument and that switches the conduction state and the cutoff state between a pair of contacts by being pressed in a reference direction, and the axis side of the sheath with respect to the action portion and the reference direction may be set so as to be parallel to each other.

According to a tenth aspect of the present invention, a control method of an instrument includes: controlling the operation of a medical instrument insertable into a body; and operating the instrument only when an instruction for operating the instrument is detected when the manipulator holds the instrument in the body.

BRIEF DESCRIPTION OF DRAWINGS

FIG. 41 is a view showing a difference between a first mode and a second mode in a medical manipulator related to a tenth embodiment of the present invention.

FIG. 43 is a view showing the state of a holder and the instrument before and after switching from the first mode to the second mode.

DESCRIPTION OF EMBODIMENTS

First Embodiment

A first embodiment of a manipulator system related to the present invention will be described below, referring to FIGS. 1 to 4.

Figure 1:
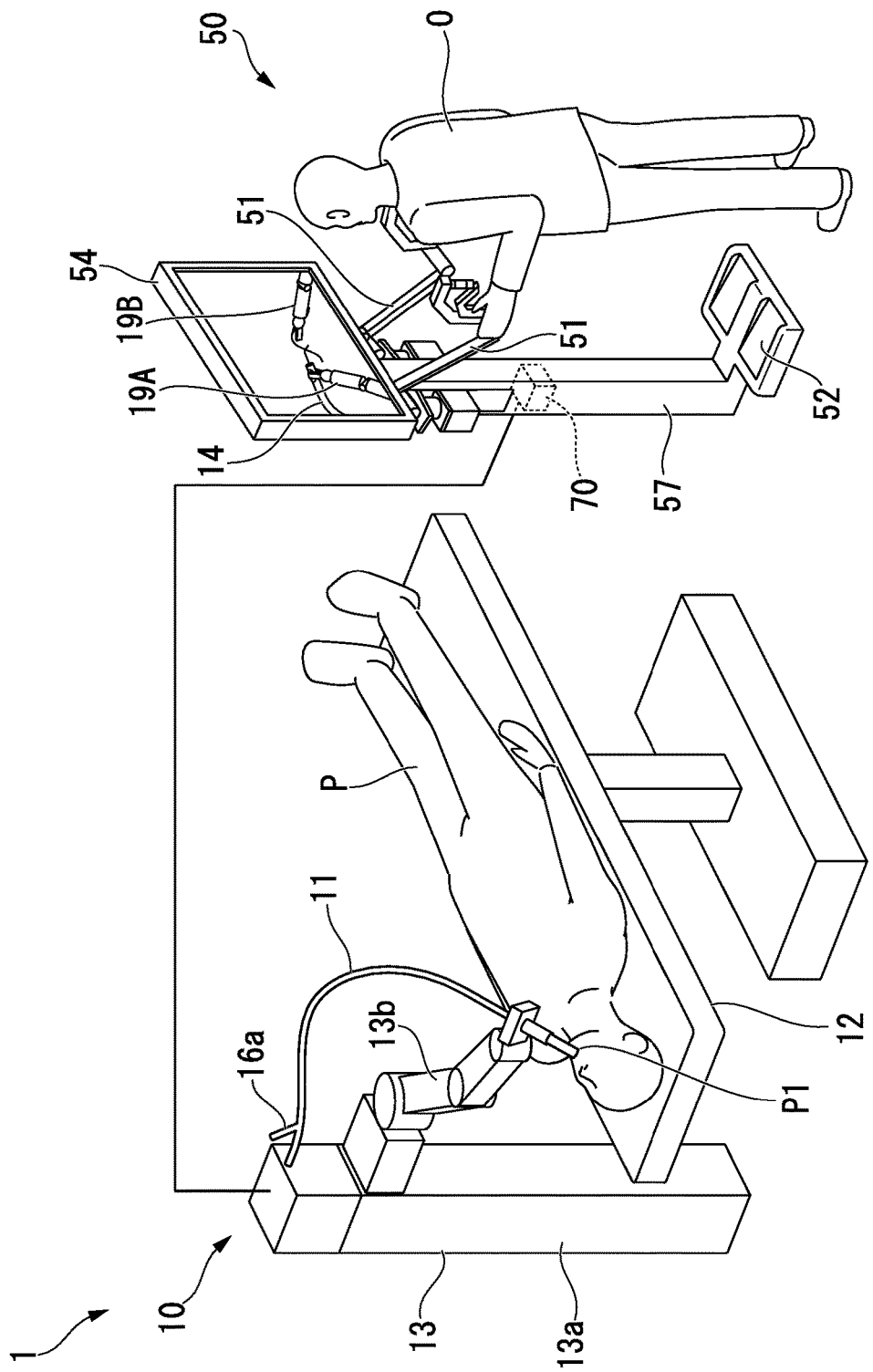
FIG. 1 is an overall view showing a manipulator system of a first embodiment of the present invention.
Figure 2:
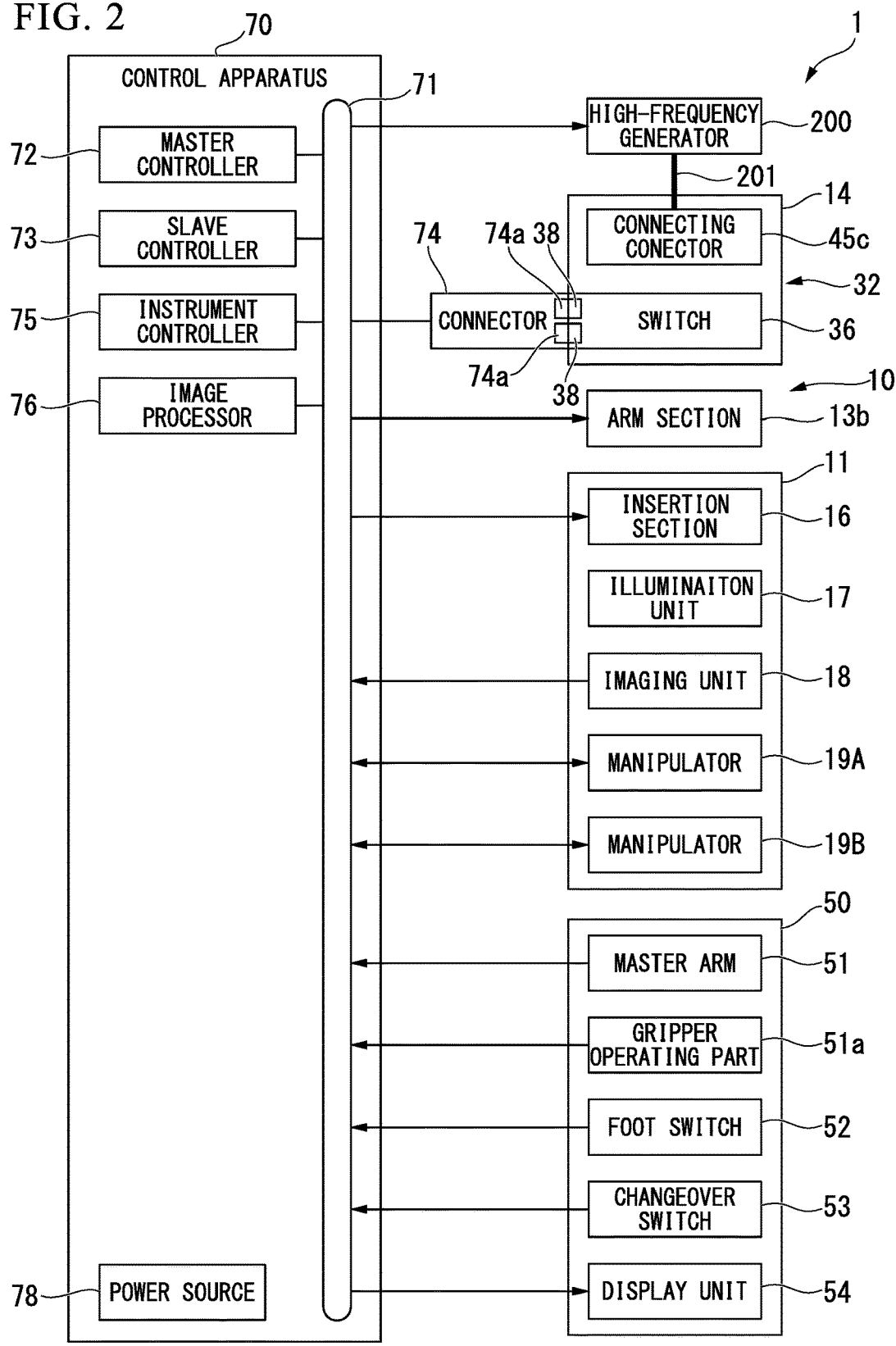
FIG. 2 is a block diagram of the manipulator system.

As shown in FIGS. 1 and 2, the present manipulator system 1 includes a slave apparatus 10 provided with an endoscope device 11, a master apparatus 50 that an operator O, such as a surgeon, operates and that gives operating information, and a control apparatus 70 that controls the slave apparatus 10 according to the operating information.

Figure 3:
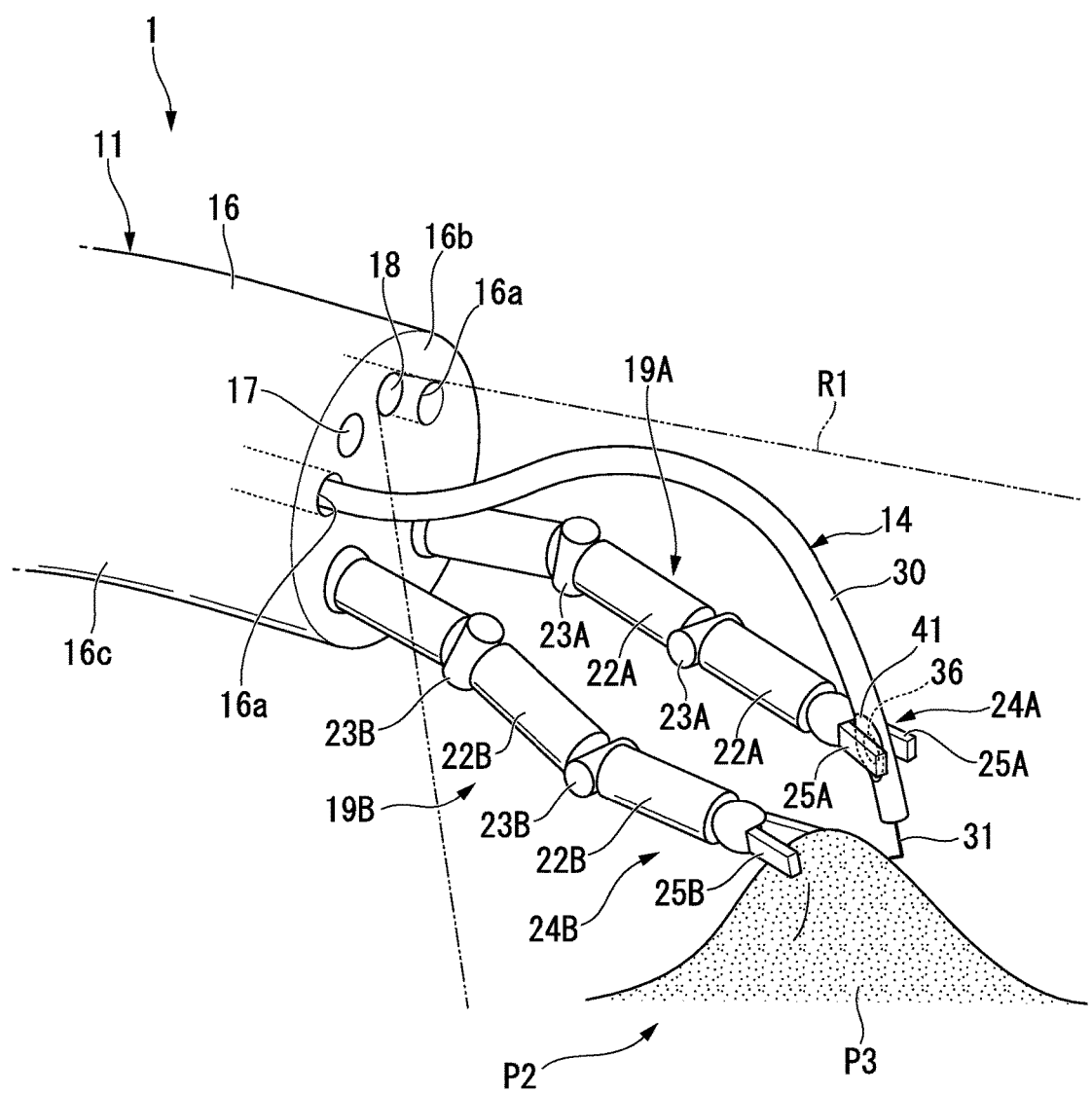
FIG. 3 is a perspective view of a distal portion in an endoscope device of the manipulator system.

The slave apparatus 10, as shown in FIGS. 1 and 3, has a surgical table 12 on which a patient P is placed, a multi-joint robot 13 arranged in the vicinity of the surgical table 12, the above endoscope device 11 attached to the multi-joint robot 13, and a hook-shaped knife (instrument) 14 of the present invention capable of being inserted through a working channel 16a provided in the endoscope device 11.

The multi-joint robot 13, as shown in FIG. 1, is a multi-joint robot of a well-known configuration having an arm section 13b and a proximal end portion of the multi-joint robot is fixed to a base 13a. The arm section 13b has a so-called multi-joint structure. The arm section 13b operates according to the operating information output from the master apparatus 50.

The endoscope device 11, as shown in FIG. 3, has a longitudinal and flexible insertion section 16. A pair of working channels 16a are formed in the insertion section 16, and the working channels 16a open to a distal surface 16b of the insertion section 16. A bending portion 16c capable of being operated for bending is provided at the portion of the insertion section 16 located further toward a proximal end side than the distal surface 16b. Additionally, the working channels 16a also open to a proximal end portion of the insertion section 16 (refer to FIG. 1).

The distal surface 16b of the insertion section 16 is provided with an illumination unit 17 having LEDs, an imaging unit 18 that has a CCD or the like, and a pair of manipulators 19A and 19B.

The illumination unit 17 illuminates the front of the insertion section 16 by electric power being supplied thereto from a power source 78 to be described below. The imaging unit 18 acquires an image from an observation object within a predetermined visual field R1, converts the image into signals, and outputs the signals to the control apparatus 70.

Since the configuration of the manipulator 19A and the configuration of the manipulator 19B are the same in the present embodiment, the configuration of the manipulator 19A is shown by adding an alphabetic character "A" to a number, and the configuration of the manipulator 19B is shown by adding the alphabetic character "B" to the same number. Accordingly, duplicate description will be omitted.

End portions of a plurality of tubular parts 22A of the manipulator 19A are configured so as to be connected together with a joint part 23A. Although not shown, a joint drive motor is provided further toward the proximal end side than the manipulator 19A, and each joint part 23A is turned with a wire or the like connected to a drive shaft of the joint drive motor. The angle formed between the tubular parts 22A adjacent to each other is calculated by detecting the rotation number of the drive shaft of the joint drive motor with an angle detection sensor, such as an encoder. The control apparatus 70 drives the joint drive motor on the basis of a detection value obtained using the angle detection sensor.

The tubular part 22A provided furthest toward the proximal end side is attached to the distal surface 16b of the insertion section 16. The manipulator 19A configured in this way has a multi-joint structure having at least one degree of freedom.

A gripper 24A is provided at the distal of the tubular part 22A furthest toward the distal side. The gripper 24A has a pair of grip pieces 25A. The grip pieces 25A can be brought close to and separated from each other by a grip piece drive motor and a well-known opening and closing mechanism that are not shown.

The manipulators 19A and 19B and the grippers 24A and 24B of the endoscope device 11 operate according to the operating information output from the master apparatus 50. The grippers 24A and 24B of the manipulators 19A and 19B can grip the portion of a sheath 30 (to be described below) of the hook-shaped knife 14 that is provided with a grip detector 32. That is, in this example, the hook-shaped knife 14 is held as the manipulator 19A grips the hook-shaped knife 14.

The hook-shaped knife 14 is an example of an instrument used after being inserted through a working channel 16a of the endoscope device 11 in the manipulator system 1 of the present embodiment.

Figure 4:
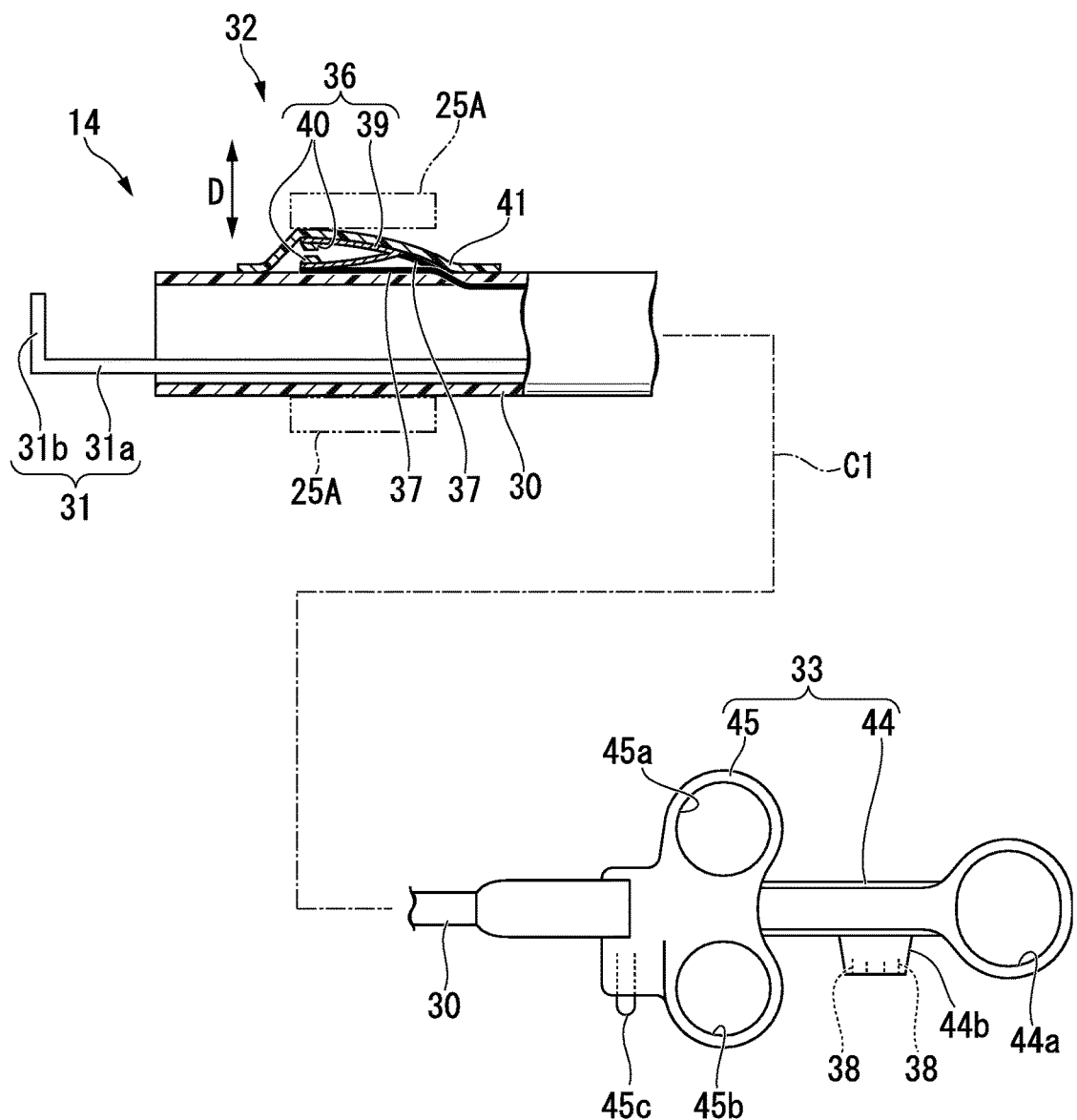
FIG. 4 is a side view when a portion of a hook-shaped knife of the manipulator system is broken.

The hook-shaped knife 14, as shown in FIG. 4, includes the sheath 30, a knife part (treatment part) 31 provided so as to be capable of advancing into and retracting from the sheath 30, the grip detector (holding detector) 32 provided on the outer surface of the sheath 30, and an instrument operating part 33 attached to the proximal end portion of the sheath 30.

The sheath 30 is formed in the shape of a tube from a material having an electrical insulation property and flexibility, such as silicon resin. The knife part 31 is configured so that a hook portion 31b is connected to a distal portion of the knife body 31a, which is formed in the shape of a rod, so as to be orthogonal to the knife body 31a. The length of the hook portion 31b is set to be smaller than the internal diameter of the sheath 30. The knife part 31 can be formed from a metal, such as stainless steel.

The grip detector 32, as shown in FIGS. 2 and 4, has a switch 36, a pair of wiring lines 37 whose distal portions are connected to the switch 36, and a pair of contacts 38 electrically connected to proximal end portions of wiring lines 37.

The switch 36 is arranged so that a pair of electrodes 40 face each other on an inner surface of a distal portion of a spring member 39 formed in the shape of the letter V from resin having an insulation property. In a natural state where no external force other than gravity is exerted, the electrodes 40 are arranged so as to be slightly separated from each other. The distal portions of the wiring lines 37 are electrically connected to the electrodes 40. In this example, each wiring line 37 passes through the sheath 30 from an outer surface side to an inner surface side on a proximal end side of the switch 36, and extends to the proximal end side in the inner surface of the sheath 30.

The switch 36 and the distal portion of each wiring lines 37 are sealed in a watertight manner by a sealing member 41 disposed between the sealing member and the sheath 30. The sealing member 41 is formed in the shape of a sheet from pliable resin having an insulation property.

In order to stably perform a treatment in a state where the hook-shaped knife 14 is gripped by the manipulator 19A, it is preferable that the grip detector 32 be provided at a distal portion of the sheath 30.

The instrument operating part 33 includes an operating part body 44 attached to the proximal end portion of the sheath 30, and a slider 45 that is slidable with respect to the operating part body 44. The operating part body 44 has a finger-hooking ring 44a at a proximal end portion thereof. The operating part body 44 is provided with a contact platform 44b, and a pair of contacts 38 are attached to the contact platform 44b in a state where the contacts are exposed to the outside.

The slider 45 includes finger-hooking rings 45a and 45b. The finger-hooking rings 45a and 45b are arranged in a direction orthogonal to an axis C1 of the sheath 30. The slider 45 includes a connecting connector 45c. The connecting connector 45c is electrically connected to a proximal end portion of the knife body 31a in the knife part 31. A cord 201 provided in a high-frequency generator 200 shown in FIG. 2 is attachable to and detachable from the connecting connector 45c.

The hook-shaped knife 14 configured in this way is able to make the slider 45 slide in the direction of the axis C1 to the operating part body 44, for example, by putting the thumb into the ring 44a of the operating part body 44, putting the index finger and the middle finger into the rings 45a and 45b of the slider 45, and operating the rings with the thumb, the index finger, and the middle finger. At this time, the hook portion 31b of the knife part 31 can be protruded to the outside and retracted from the distal portion of the sheath 30.

The hook-shaped knife 14 is configured so as to be capable of being inserted into the body a patient P. The cord 201 of the high-frequency generator 200 is connected to the connecting connector 45c, and the slider 45 is moved (pushed in) to the distal side with respect to the operating part body 44. Moreover, when some conditions to be described below are satisfied, a medical action of sending a high-frequency current through the knife part 31 (operating the knife part) within the body of the patient P and incising (treating) a tissue open can be executed.

In a natural state, a state between the pair of contacts 38 is a cutoff (OFF) state where an electrical connection is not made. As will be described below, when the hook-shaped knife 14 is inserted into the body of the patient P, the portion of the sheath 30 provided with the switch 36 is gripped by the gripper 24A of the manipulator 19A. At this time, as the switch 36 is pressed in a reference direction D shown in FIG. 4, the state between the pair of contacts 38 is switched from the cutoff state to a conduction (ON) state where an electrical connection is made. As the state between the pair of contacts 38 is the conduction state, the manipulator 19A can detect a gripping state (holding state) where the hook-shaped knife 14 is gripped.

The orientation of the sheath 30 to the orientation (direction in which the manipulator 19A extends) of the gripper 24A when the gripper 24A of the manipulator 19A grips the switch 36 is not limited particularly if the state between the pair of contacts 38 is switched from the cutoff state to the conduction state. The orientation of the sheath 30 to the orientation of the gripper 24A may be orthogonal or may be intersecting.

It is preferable to make the color of the sheath 30 and the color of the sealing member 41 different from each other so that the portion of the sheath 30 provided with the switch 36 can be clearly viewed with the body of the patient P.

The master apparatus 50, as shown in FIGS. 1 and 2, includes a pair of master arms 51 moved by the operator O, a foot switch (instruction-receiving part) 52 that detects an instruction performed by the operator O, a changeover switch 53 that switches an object operated by the master arms 51, and a display unit 54 for displaying an image acquired by the imaging unit 18 of the endoscope device 11.

In the present embodiment, the master arms 51 are operating parts provided in order to operate the arm section 13b of the multi-joint robot 13, the insertion section 16, and the manipulators 19A and 19B. The pair of master arms 51 correspond a right hand and a left hand of the operator O. The master arms 51 have a multi-joint structure in order to control the manipulators 19A and 19B or the like having a multi-joint structure.

Proximal end portions of the master arms 51 are attached to a support 57. A gripper operating part 51a (refer to FIG. 2) for operating the grippers 24A and 24B of the manipulators 19A and 19B is provided at a distal portion located on the operator O side of the master arms 51. When at least one of a pair of gripper operating parts 51a is operated, the pair of master arms 51 and the gripper operating part 51a output the operating information according to the operation of the control apparatus 70.

A well-known configuration can be used as the foot switch 52. The foot switch 52 is provided at a lower end portion of the support 57. As the operator O pushes the foot switch 52 with his/her foot, an instruction signal (instruction) for sending a high-frequency current through the hook-shaped knife 14 is output to the control apparatus 70.

The changeover switch 53 switches an object operated by the master arms 51 among the arm section 13b of the multi-joint robot 13, the insertion section 16, and the manipulators 19A and 19B (hereinafter referred to as the "manipulator 19A or the like"). The changeover switch 53 considers and outputs one or two kinds of information selected from the manipulator 19A or the like to the control apparatus 70.

The display unit 54 can display an image acquired by the imaging unit 18 provided in the endoscope device 11. When the endoscope device 11 is inserted into the body of the patient P, the manipulators 19A and 19B and the hook-shaped knife 14 together with a target tissue are displayed on the display unit 54.

In this example, the display unit 54 is provided at an upper end portion of the support 57.

The control apparatus 70, as shown in FIG. 2, has a master controller 72, a slave controller 73, a connector 74, an instrument controller (controller) 75, and an image processor 76 that are connected to a bus 71, and the power source 78.

The arm section 13b of the multi-joint robot 13, the insertion section 16, the imaging unit 18, and the manipulators 19A and 19B of the endoscope device 11, and the master arms 51, the gripper operating part 51a, the foot switch 52, the changeover switch 53, and the display unit 54 of the master apparatus 50 are connected to the bus 71.

The master controller 72, the slave controller 73, the instrument controller 75, and the image processor 76 are configured by an arithmetic element, a memory, and control programs, respectively.

The master controller 72 calculates command values of the position and orientation of the distal of the manipulator 19A or the like according to the operating information output from the master arms 51 in correspondence with to the selected information output from the changeover switch 53, among the manipulators 19A or the like. Then, the calculated command values are output to the slave controller 73.

The slave controller 73 calculates the driving amounts of the joints of the manipulator 19A or the like, which are required to match the command values of the position and orientation of the distal of the manipulator 19A or the like, using inverse kinematics calculation, on the basis of the command values of the position and orientation calculated by the master controller 72 and the selected information output from the changeover switch 53. Then, the manipulator 19A or the like is driven on the basis of the calculation results.

The connector 74 is provided with a pair of body-side contacts 74a. By attaching the contact platform 44b of the hook-shaped knife 14 to the connector 74, each body-side contact 74a and each contact 38 are electrically connected to each other.

The instrument controller 75 detects whether a state between the pair of body-side contacts 74a, that is, between the pair of contacts 38 is the conduction state or the cutoff state when the contact platform 44b is attached to the connector 74. The instrument controller 75 controls the high-frequency generator 200 so as to output a high-frequency current. The instrument controller 75 makes the high-frequency generator 200 output the high-frequency current only in a case where an instruction signal output from the foot switch 52 is detected, when the state between the pair of contacts 38 is the conduction state (gripping state).

The image processor 76 appropriately converts image signals output from the imaging unit 18 and outputs the image signals to the display unit 54.

The power source 78 supplies the electric power input from the outside to the slave apparatus 10, the master apparatus 50, the master controller 72, or the like.

In this example, as shown in FIG. 1, the control apparatus 70 is provided at the support 57.

Next, a procedure using the manipulator system 1 of the present embodiment with the above configuration will be described with emphasis on a control method of an instrument that controls the operation of the hook-shaped knife 14. Although a case where a target tissue formed in the stomach wall is incised will be described below, a target part is not limited to this, and may be, for example, lumen organs, such as the esophagus, the duodenum, the small intestine, the large intestine, the womb, and the bladder.

A helper, as shown in FIG. 1, makes a patient P lie on the surgical table 12 and performs suitable processing, such as disinfection or anesthesia. If the manipulator system 1 is started, electric power is supplied to the slave apparatus 10, the master apparatus 50, the master controller 72, or the like from the power source 78.

The front of the insertion section 16 is illuminated by supplying electric power from the power source 78 to the illumination unit 17. The operator O checks an image in front of the insertion section 16, which is acquired by the imaging unit 18, using the display unit 54. The changeover switch 53 makes a switching so that the arm section 13b of the multi-joint robot 13 is operated by the master arms 51. The master arms 51 are operated to drive the arm section 13b, and the insertion section 16 of the endoscope device 11 is introduced to the stomach through a mouth P1 of the patient P. While the bending portion 16c is appropriately bent, as shown in FIG. 3, the distal surface 16b of the insertion section 16 is made to face a target tissue P3 formed in a stomach wall P2 and this state is held.

A helper inserts a syringe (not shown) through the working channel 16a of the endoscope device 11. The operator O performs a switching using the changeover switch 53 so that the manipulators 19A and 19B are operated by the master arms 51. The syringe is gripped by operating the pair of grip pieces 25A of the manipulator 19A so as to come close to each other. The manipulator 19A is driven to puncture the target tissue P3 with a syringe, and a physiological salt solution is injected into a submucosal layer (not shown) under the target tissue P3 to cause the target tissue P3 to bulge. The gripping of the syringe by the gripper 24A is released while extracting the syringe from the target tissue P3. The helper extracts the syringe from the working channel 16a of the endoscope device 11.

The instrument operating part 33 of the hook-shaped knife 14 is operated to move (pull back) the slider 45 to the proximal end side with respect to the operating part body 44, and the knife part 31 is housed within the sheath 30. The hook-shaped knife 14 is inserted through the working channel 16a of the endoscope device 11. At this time, the switch 36 of the grip detector 32 is made to protrude forward from the working channel 16a. The cord 201 of the high-frequency generator 200 is attached to the connecting connector 45c of the hook-shaped knife 14. The contact platform 44b of the hook-shaped knife 14 is attached to the connector 74 of the control apparatus 70.

The target tissue P3 caused to bulge is gripped by the gripper 24B of the manipulator 19B. As shown in FIG. 4, the portion of the sheath 30 of the hook-shaped knife 14 provided with the switch 36 is gripped so as to be pinched in the reference direction D by the pair of grip pieces 25A of the manipulator 19A, and this gripped state is maintained. Both of distal portions of the spring member 39 are elastically deformed so as to come close to each other, and the pair of electrodes 40 come into contact with each other. Accordingly, the state between the pair of contacts 38 is switched from the cutoff state to the conduction state where an electrical connection is made. Although the instrument controller 75 detects that the state between the pair of contacts 38 is the conduction state, that is, the gripping state, an instruction signal from the foot switch 52 is not detected at this time. Therefore, a high-frequency current is not output to the high-frequency generator 200. Since an image in which the hook-shaped knife 14 is gripped by the gripper 24A of the manipulator 19A is displayed on the display unit 54, the operator O can easily check the type of an instrument gripped by the manipulator 19A.

The instrument operating part 33 of the hook-shaped knife 14 is operated to push in the slider 45, and the knife part 31 is made to protrude from the distal portion of the sheath 30.

If the operator O pushes the foot switch 52 with his/her foot, an instruction signal is output from the foot switch 52 to the control apparatus 70. If the instrument controller 75 detects the instruction signal, the state between the pair of contacts 38 at this time is the conduction state, and the gripping state is detected. Therefore, a high-frequency current is output to the high-frequency generator 200.

While the hook-shaped knife 14 is gripped by the gripper 24A of the manipulator 19A, the manipulator 19A is moved in a state where the foot switch 52 is pushed with a foot, and the knife part 31 of the hook-shaped knife 14 is pressed against the target tissue P3 caused to bulge, thereby incising the target tissue P3.

The target tissue P3 is altogether incised and exfoliated. If the operator O removes his/her foot from the foot switch 52, an instruction signal is no longer output from the foot switch 52, and the instrument controller 75 stops the output of the high-frequency current by the high-frequency generator 200. The slider 45 is pulled back so that the knife part 31 is kept from protruding to the outside from the distal portion of the sheath 30. The gripping of the hook-shaped knife 14 by the manipulator 19A is released, and the gripping of the target tissue P3 by the manipulator 19B is released.

Gripping forceps (not shown) are inserted through an empty working channel 16a of the endoscope device 11. The target tissue P3 endoscopically exfoliated by operating the gripping forceps is taken out outside. The insertion section 16 is extracted from the mouth P1 of the patient P, and a required treatment is made to end a series of procedures.

According to the manipulator system 1 of the present embodiment and the control method of the hook-shaped knife 14, only when the holding state where the manipulator 19A holds the hook-shaped knife 14 within the body of the patient P is detected, the hook-shaped knife 14 is operated only in a case where an instruction for operating the hook-shaped knife 14 by the operator O is detected. Accordingly, the operator O can reliably perform a treatment with the hook-shaped knife 14.

Additionally, according to the hook-shaped knife 14 of the present embodiment, the gripping state where the hook-shaped knife 14 is gripped by the gripper 24A of the manipulator 19A can be detected by the grip detector 32. For this reason, an instrument that is intended to operate can be reliably recognized by comparing and checking the detection result of the gripping state and the image in which the hook-shaped knife 14 is gripped by the manipulator 19A displayed on the display unit 54. Accordingly, a treatment can be reliably performed by the hook-shaped knife 14.

Since the grip detector 32 has the switch 36, the state between the pair of contacts 38 is switched from the cutoff state to the conduction state as the switch 36 is pressed in the reference direction D by the gripper 24A. For this reason, the gripping state can be detected with a simple configuration referred to as the switch 36.

Second Embodiment

Next, although a second embodiment of the present invention will be described referring to FIGS. 5 and 6, the same parts as the above embodiment will be designated by the same reference numerals and the description thereof will be omitted, and only different points will be described.

Figure 5:
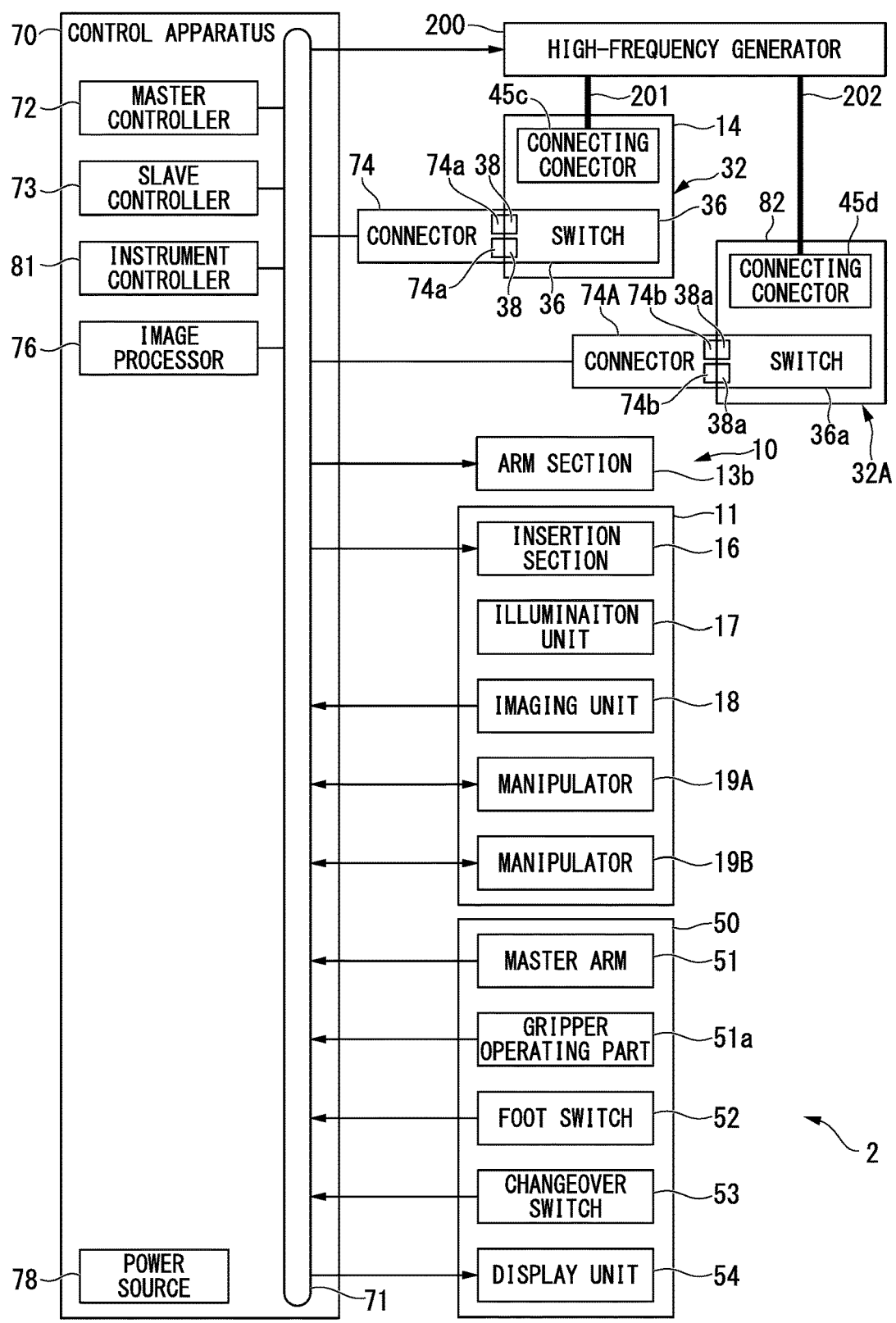
FIG. 5 is a block diagram of a manipulator system of a second embodiment of the present invention.
Figure 6:
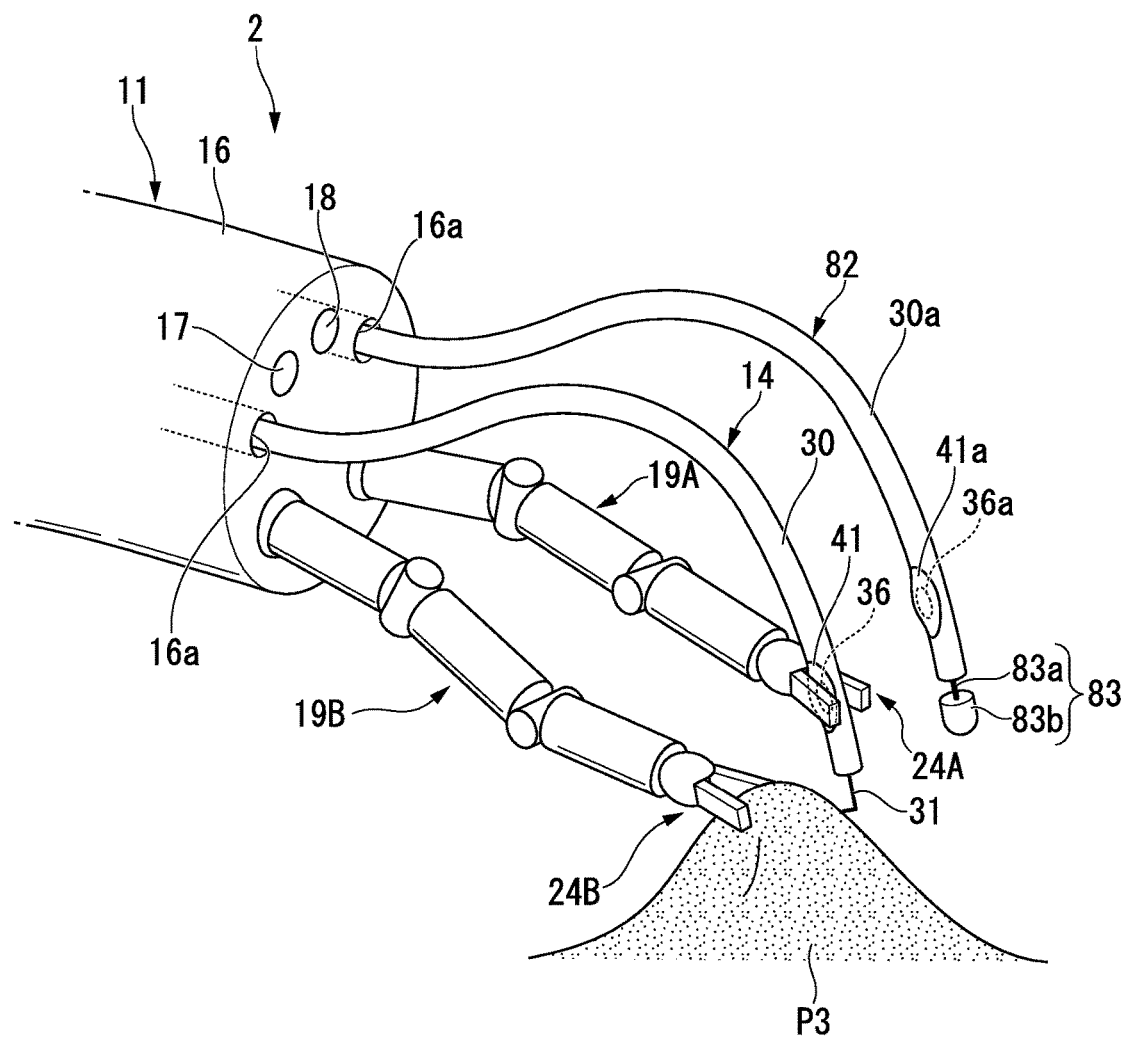
FIG. 6 is a perspective view of a distal portion in an endoscope device of the manipulator system.

As shown in FIGS. 5 and 6, a manipulator system 2 of the present embodiment includes an instrument controller 81 instead of the instrument controller 75 of the manipulator system 1 of the first embodiment, and includes a rod-shaped high-frequency knife (second instrument) 82 in addition to the above hook-shaped knife (first instrument) 14 as an instrument.

The control apparatus 70 includes the same connector 74A as the connector 74 separately from the connector 74. The connector 74A is connected to the bus 71.

The high-frequency knife 82 includes a sheath 30a, and a knife part 83 instead of the knife part 31 of the hook-shaped knife 14. In the knife part 83, a distal portion of the rod-shaped electrode 83a formed in the shape of a rod is provided with an insulated distal 83b formed to have a larger diameter than the rod-shaped electrode 83a.

The high-frequency knife 82 is also provided with a grip detector 32A with the same configuration as the same grip detector 32. The grip detector 32A has a switch 36a with the same configuration as the switch 36, a connecting connector 45d with the same configuration as the connecting connector 45c, and the same sealing member 41a as the sealing member 41.

By attaching the contact platform 44b of the high-frequency knife 82 to the connector 74A, each body-side contact 74b of the connector 74A and the contact 38a of the high-frequency knife 82 are electrically connected to each other. A cord 202 provided in the high-frequency generator 200 is attachable to and detachable from to the connecting connector 45d of the high-frequency knife 82.

The instrument controller 81 is different from the instrument controller 75 of the first embodiment only in terms of the following control contents. That is, when the grip detector 32 has detected the gripping state between the manipulator 19A and the hook-shaped knife 14, only the hook-shaped knife 14 is operated and the high-frequency knife 82 is not operated (a high-frequency current is not applied) in a case where the instrument controller 81 has detected an instruction signal output from the foot switch 52. Additionally, when the grip detector 32A has detected the gripping state between the manipulator 19A and the high-frequency knife 82, only the high-frequency knife 82 is operated and the hook-shaped knife 14 is not made to operate in a case where the instrument controller 81 has detected an instruction signal output from the foot switch 52.

According to the manipulator system 2 of the present embodiment configured in this way, when the foot switch 52 is pushed with a foot, a high-frequency current is applied to only an instrument gripped by the manipulator 19A. Additionally, the instrument gripped by the manipulator 19A can be easily checked with an image displayed on the display unit 54. Accordingly, the operator O can reliably perform a treatment with the instrument.

Additionally, since the number of the foot switch 52 provided in the manipulator system 2 is one, the operation by the operator O can be kept from becoming complicated.

The present embodiment may include a hook-shaped knife different from the hook-shaped knife 14 in terms of the size of the knife part 31, or the like, instead of the high-frequency knife 82.

The number of instruments provided in the manipulator system 2 is not limited, and the manipulator system 2 may include three or more instruments.

Third Embodiment

Next, although a third embodiment of the present invention will be described referring to FIGS. 7 and 8, the same parts as the above embodiment will be designated by the same reference numerals and the description thereof will be omitted, and only different points will be described.

Figure 7:
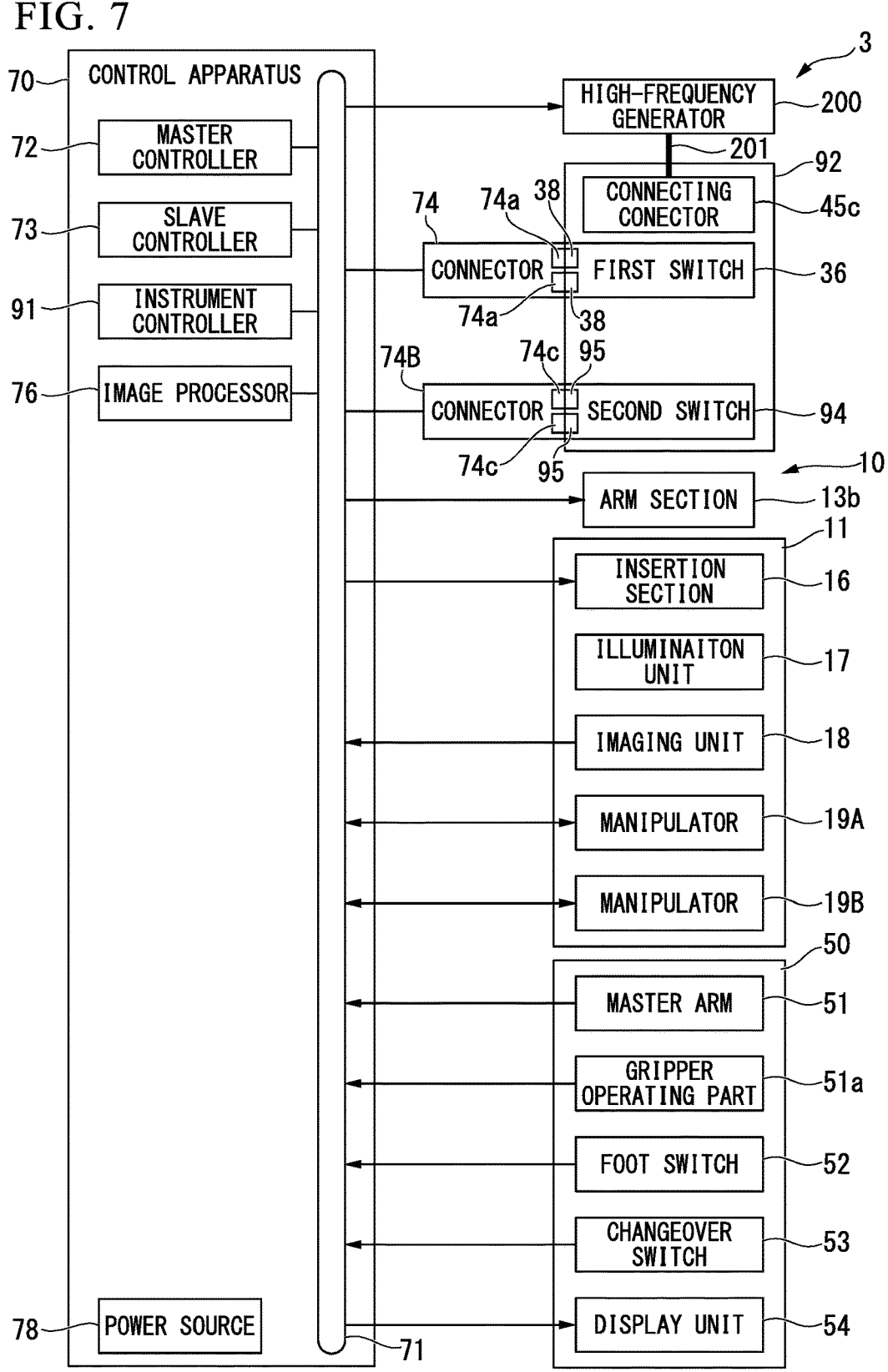
FIG. 7 is a block diagram of a manipulator system of a third embodiment of the present invention.
Figure 8:
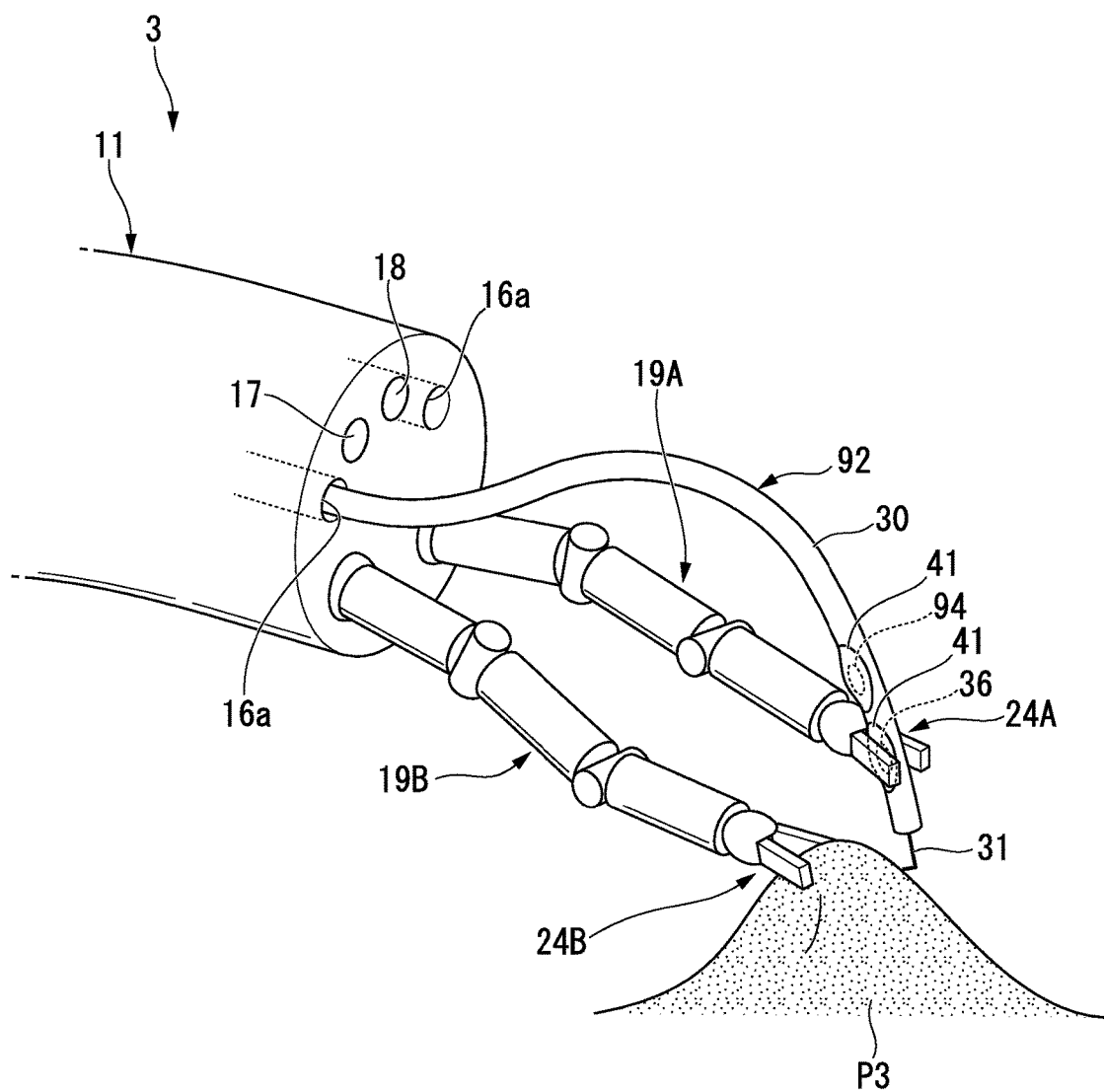
FIG. 8 is a perspective view of a distal portion in an endoscope device of the manipulator system.

As shown in FIGS. 7 and 8, a manipulator system 3 of the present embodiment includes an instrument controller 91 and a hook-shaped knife 92, instead of the instrument controller 75 and the hook-shaped knife 14 of the manipulator system 1 of the first embodiment.

The hook-shaped knife 92 has a second switch 94, a pair of second wiring lines (not shown) having distal portions connected to the second switch 94, and a pair of second contacts 95 electrically connected to proximal end portions of the second wiring lines, in addition to the respective configurations of the hook-shaped knife 14 of a first embodiment. In addition, the above switch 36 is equivalent to the first switch, and the contacts 38 are equivalent to the first contacts.

The second switch 94, the second wiring lines, and the second contacts 95 have the same configurations as the switch 36, the wiring lines 37, and the contacts 38, respectively. The second contacts 95 can be connected to a pair of body-side contacts 74c of a connector 74B.

If the portion of the sheath 30 of the hook-shaped knife 92 configured in this way, which is provided with the second switch 94, is gripped by the gripper 24A of the manipulator 19A, the state between the pair of second contacts 95 is switched from the cutoff state to the conduction state.

The instrument controller 91 is different from the instrument controller 75 of the first embodiment only in terms of the following control contents. That is, the instrument controller 91 makes the hook-shaped knife 92 perform the operation of solidifying a tissue as a first operation in a case where the instrument controller has detected an instruction signal output from the foot switch 52 when it is detected that the state between the pair of contacts 38 is the holding state and the conduction state. On the other hand, the instrument controller 91 makes the hook-shaped knife 92 perform the operation of incising a tissue as a second operation different from the first operation in a case where the instrument controller 91 has detected an instruction signal output from the foot switch 52 when it is detected that the state between the pair of second contacts 95 is the conduction state and the holding state.

In a case where a tissue is solidified and in a case where a tissue is incised, wave-like patterns of high-frequency currents supplied from the high-frequency generator 200 are different. The instrument controller 91 issues instructions to the high-frequency generator 200 according to the contacts in the conduction state, and the high-frequency generators 200 outputs high-frequency currents of patterns with mutually different patterns. Accordingly, even if the shape of the knife part 31 of the hook-shaped knife 92 is the same, a tissue that comes into contact with the knife part 31 is solidified or incised.

According to the manipulator system 3 of the present embodiment configured in this way, the operator O can reliably perform a treatment with the hook-shaped knife 92.

Additionally, since two types of operations can be performed simply by pushing one foot switch 52 with a foot, the operativity of the operator O can be improved.

In the present embodiment, the instrument is the hook-shaped knife 92, and the hook-shaped knife 92 performs a solidifying operation and an incising operation as the first operation and the second operation. However, the type of the instrument and the types of the first operation and the second operation corresponding to the instrument are not limited to this. For example, when the instrument is an ultrasonic instrument, the first operation and the second operation may be the operations of generating supersonic vibrations with mutually different frequencies.

The number of switches provided in the hook-shaped knife 92 is not limited, and the hook-shaped knife 92 may include three or more switches.

Additionally, the switch provided in the hook-shaped knife or the manipulator 19A may be configured so as to be capable of detecting a first gripping force that is a weaker gripping force generated by the gripper 24A and a second gripping force that is a stronger gripping force. By providing the switch with, for example, a strain gauge, and detecting the distortion amount of the strain gauge, two or more types of such gripping forces can be detected. In this case, the instrument controller is set so as to perform mutually different operations when the first gripping force is detected and when the second gripping force is detected.

Fourth Embodiment

Next, although a fourth embodiment of the present invention will be described referring to FIGS. 9 to 11, the same parts as the above embodiment will be designated by the same reference numerals and the description thereof will be omitted, and only different points will be described.

Figure 9:
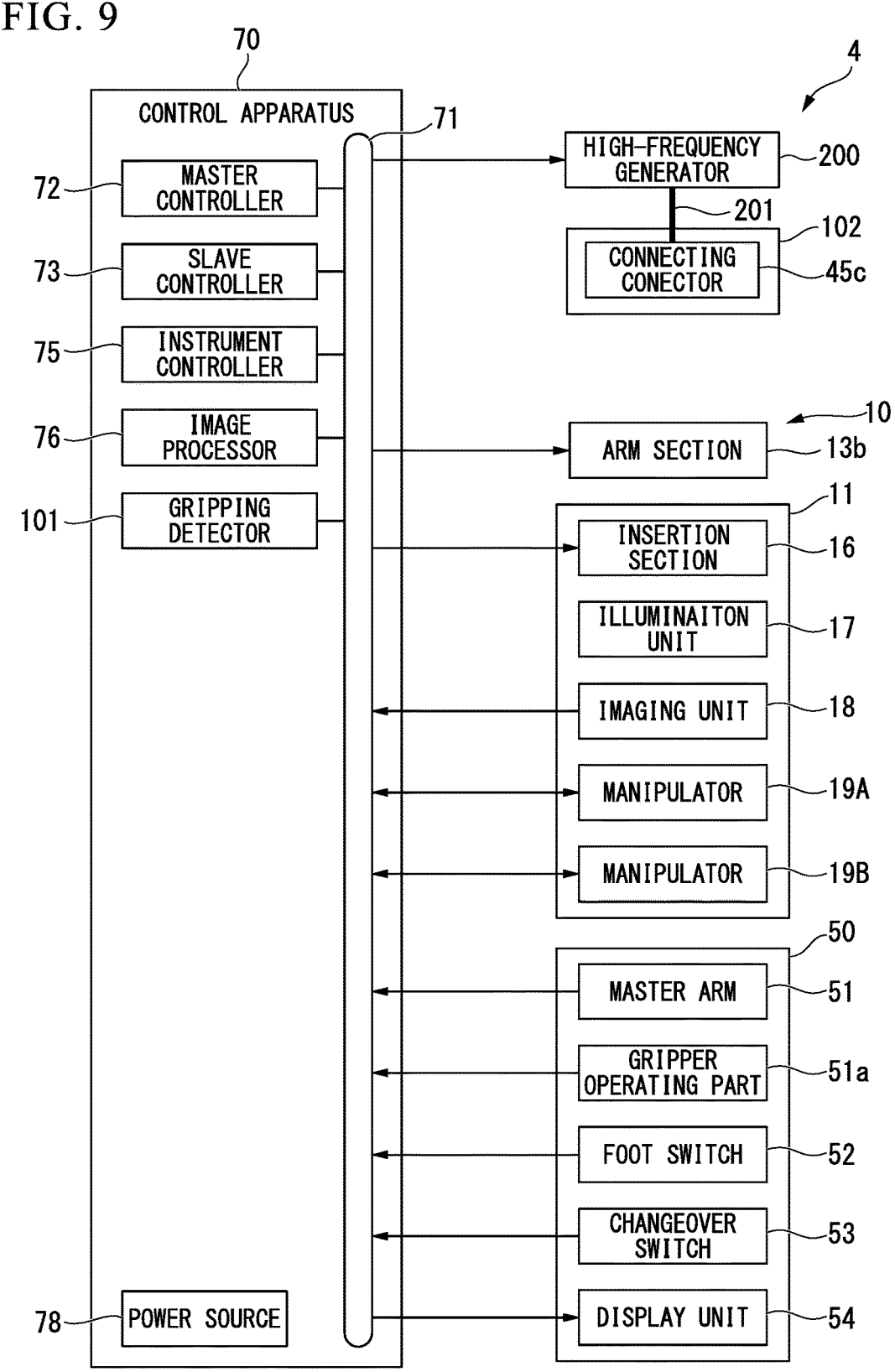
FIG. 9 is a block diagram of a manipulator system of a fourth embodiment of the present invention.
Figure 10:
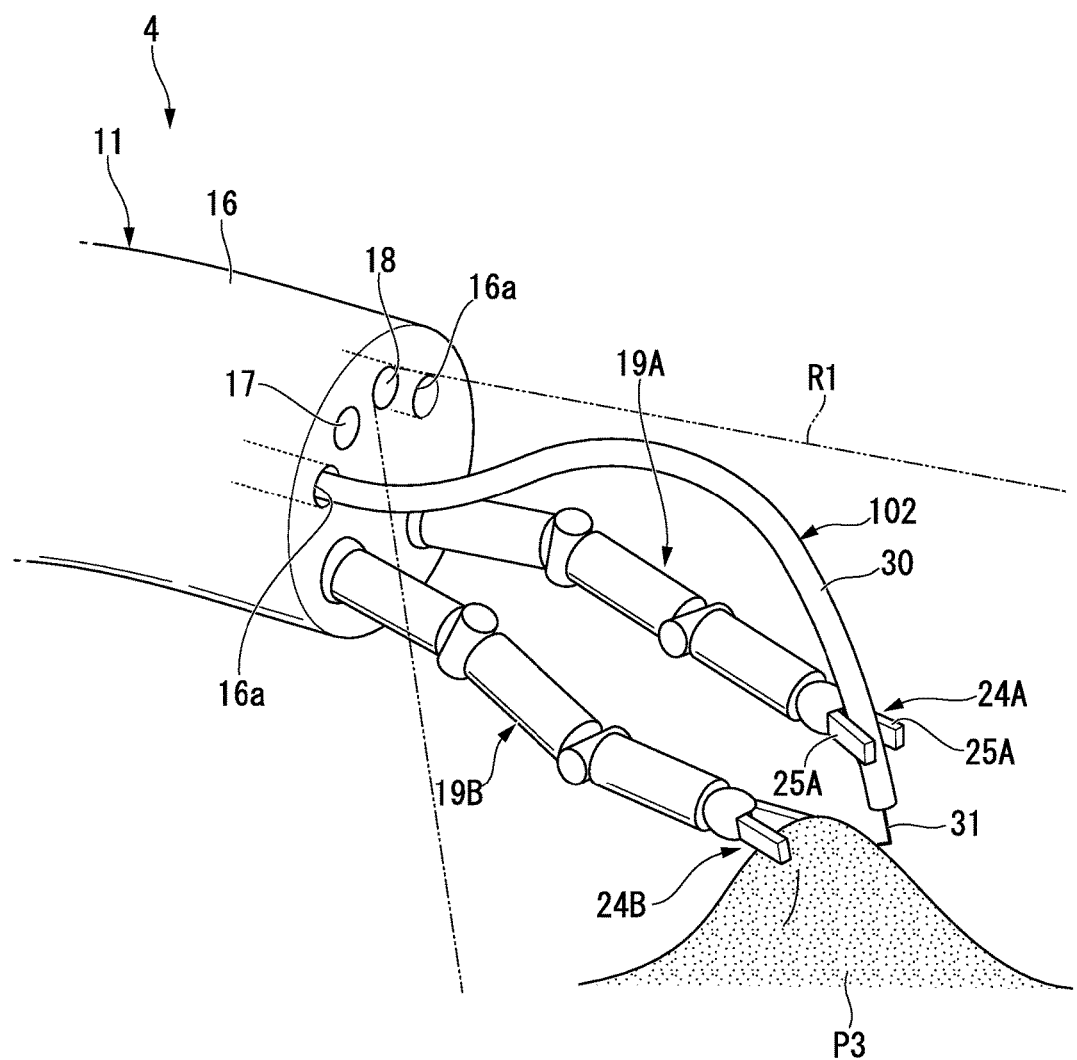
FIG. 10 is a perspective view of a distal portion in an endoscope device of the manipulator system.

As shown in FIGS. 9 and 10, the manipulator system 4 of the present embodiment includes a grip detector (holding detector) 101 and a hook-shaped knife 102, instead of the connector 74 and the hook-shaped knife 14 of the manipulator system 1 of the first embodiment.

The hook-shaped knife 102 has a configuration that does not include the grip detector 32 for the hook-shaped knife 14 of the first embodiment.

A grip detector 101 is provided in the control apparatus 70 and connected to the bus 71.

Figure 11:
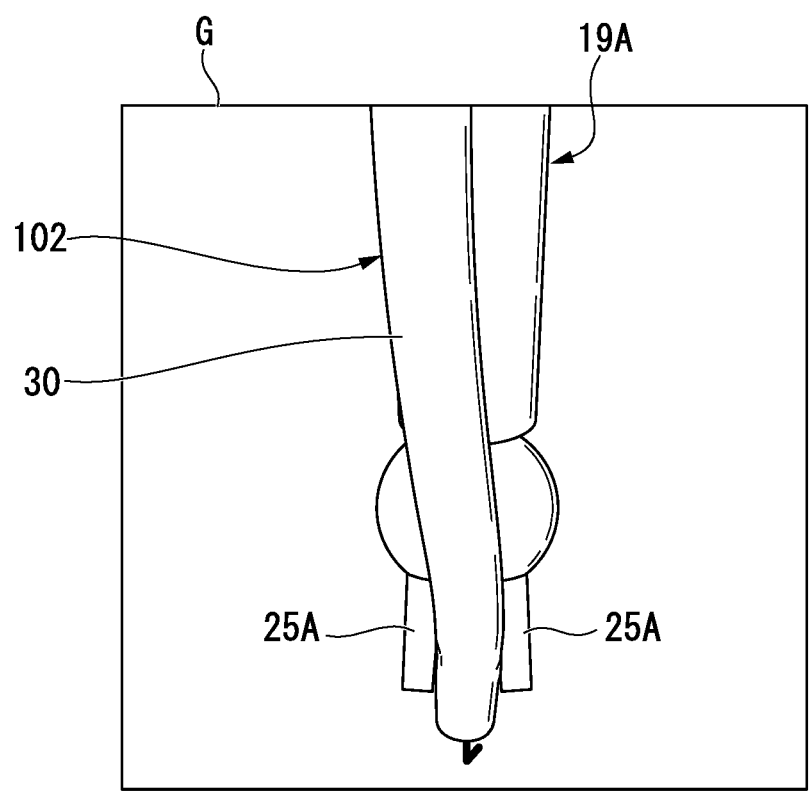
FIG. 11 is a view showing an example of an image acquired in an imaging unit of the endoscope device.

The grip detector 101, as shown in FIG. 11, detects a gripping state where the manipulator 19A grips the hook-shaped knife 102, using a well-known image analysis technique, on the basis of an image G in which the manipulator 19A and the hook-shaped knife 102 are captured.

As the image analysis technique, well-known techniques can be used appropriately. For example, a method of calculating the positions of the pair of grip pieces 25A of the manipulator 19A and the position of the sheath 30 of the hook-shaped knife 102 to detect the gripping state from a pair of images by using the endoscope device 11 that can simultaneously acquire the pair of images with parallax can be mentioned.

According to the manipulator system 4 of the present embodiment configured in this way, the operator O can reliably perform a treatment with the hook-shaped knife 102.

Additionally, since the hook-shaped knife 102 is not attached to the connector, the members connected to the hook-shaped knife 102 decrease, and the hook-shaped knife 102 can be handled easily.

The gripping state can be detected in non-contact.

In the present embodiment, the hook-shaped knife 102 may be provided with a marker. The gripping state may be detected in non-contact by calculating the position and orientation of the hook-shaped knife 102 from an image of this marker and calculating the position and orientation of the distal of the manipulator 19A.

Fifth Embodiment

Next, although a fifth embodiment of the present invention will be described referring to FIGS. 12 to 14, the same parts as the above embodiment will be designated by the same reference numerals and the description thereof will be omitted, and only different points will be described.

Figure 12:
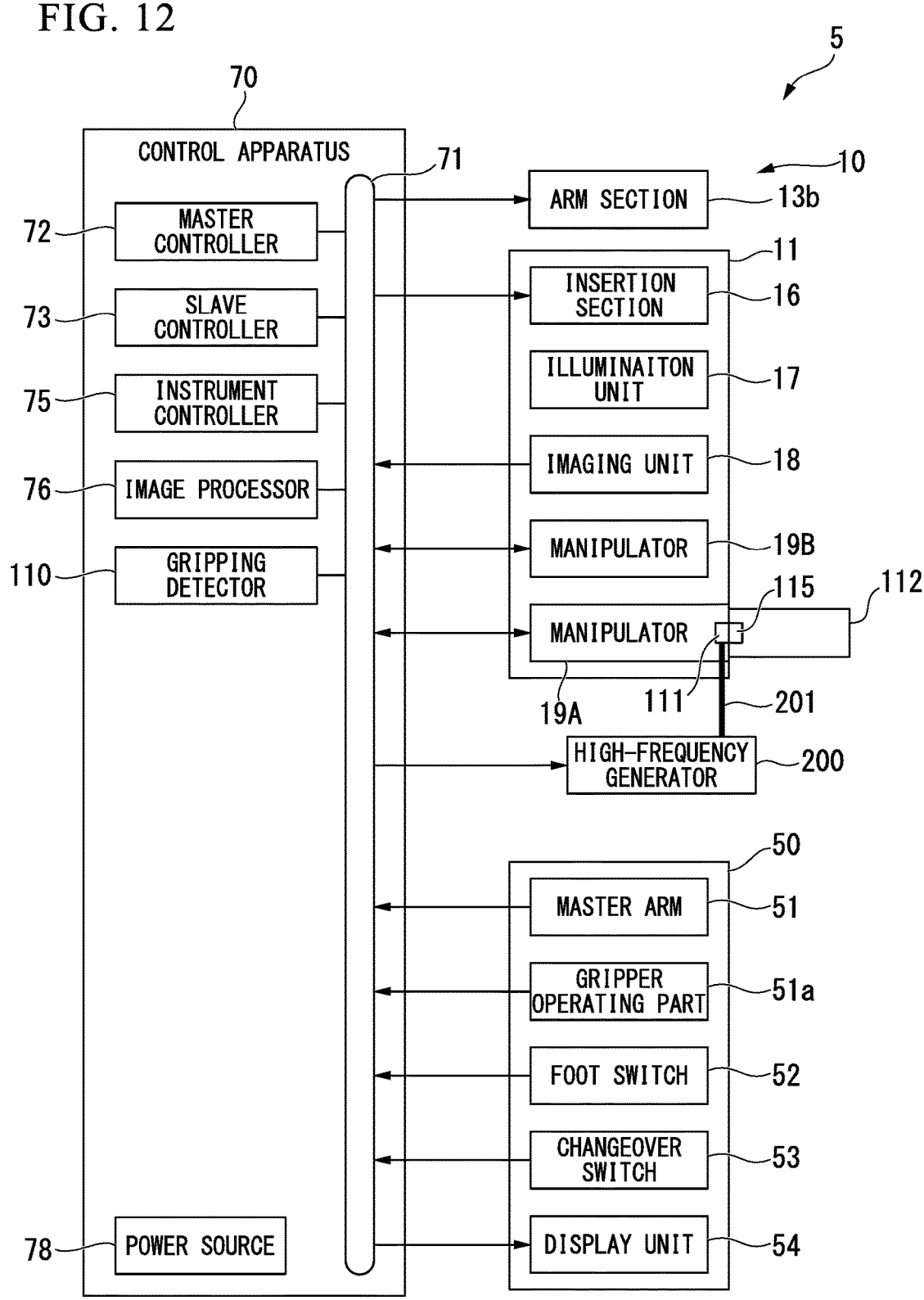
FIG. 12 is a block diagram of a manipulator system of a fifth embodiment of the present invention.
Figure 13:
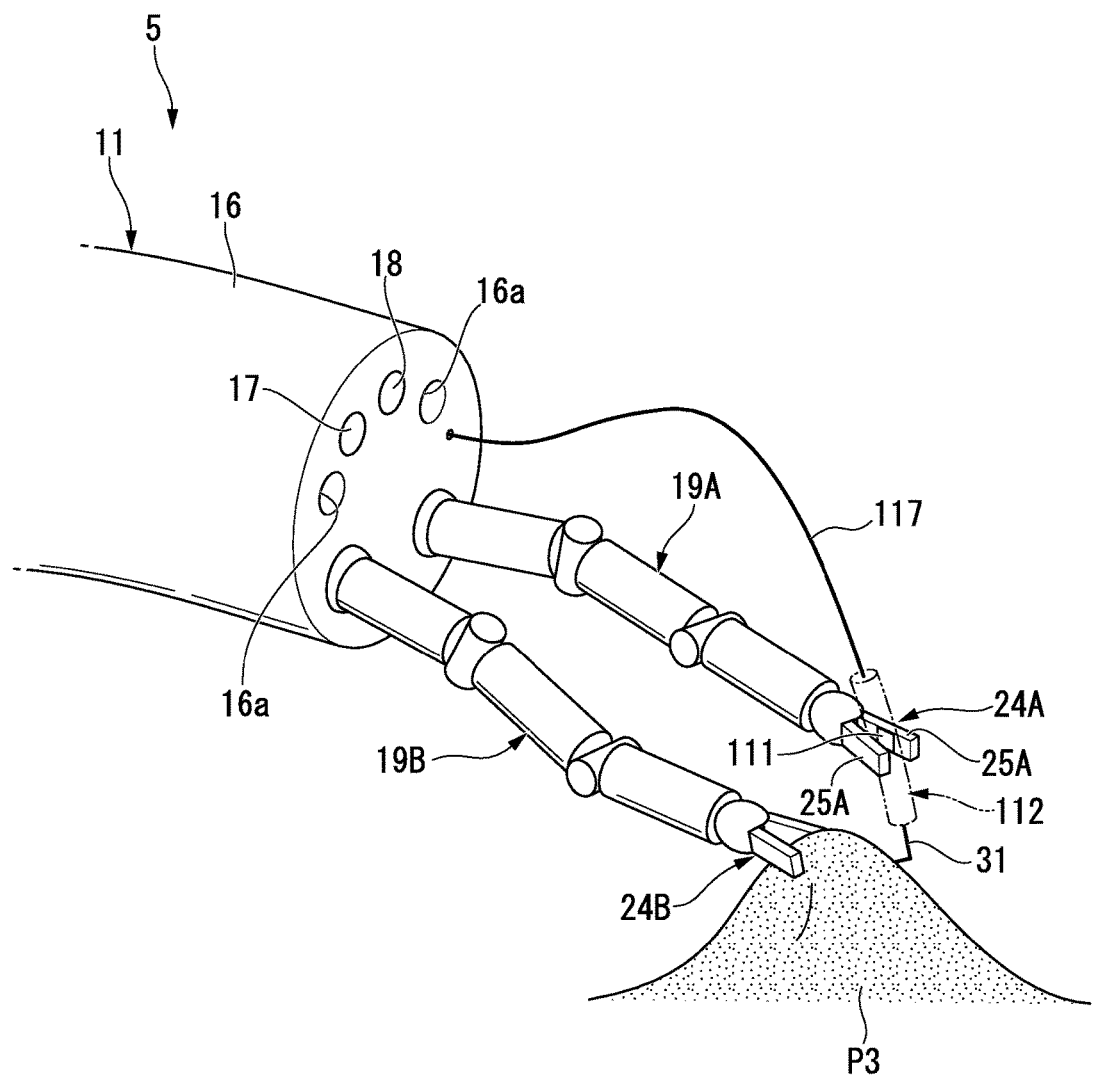
FIG. 13 is a perspective view of a distal portion in an endoscope device of the manipulator system.

As shown in FIGS. 12 and 13, a manipulator system 5 of the present embodiment includes a grip detector 110, a gripper-side electrode 111 provided on an inner surface of a grip piece 25A of the manipulator 19A, and a hook-shaped knife 112, instead of the grip detector 101 and the hook-shaped knife 102 of the manipulator system 4 of the fourth embodiment. In FIG. 13, a portion of the hook-shaped knife 112 is shown by a two-dot chain line for convenience of description.

The gripper-side electrode 111 is provided on one of the pair of grip pieces 25A in a state where the gripper-side electrode is exposed to the outside. A cord 201 of a high-frequency generator 200 is electrically connected to the gripper-side electrode 111.

Figure 14:
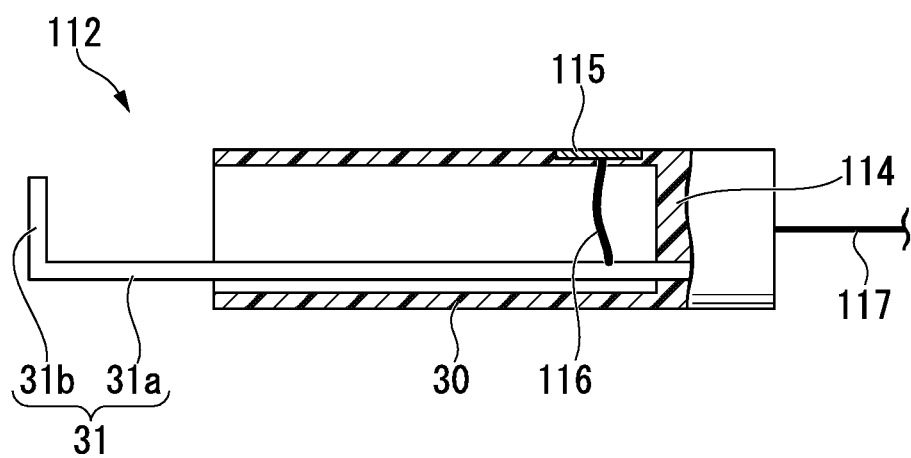
FIG. 14 is a side view when a portion of a hook-shaped knife of the manipulator system is broken.

The hook-shaped knife 112, as shown in FIGS. 13 and 14, is attached to the sheath 30 in a state where the hook portion 31b of the knife part 31 protrudes from the sheath 30. A fixing portion 114 is provided on a proximal end side of the inner surface of the sheath 30 to fix a proximal end side of the knife body 31a to the sheath 30. The fixing portion 114 is formed from a material having an insulation property.

A sheath-side electrode 115 is provided on an outer peripheral surface of the sheath 30 in a state where the sheath-side electrode is exposed to the outside. The sheath-side electrode 115 and the hook portion 31b are electrically connected to each other with a connecting wiring line 116. The proximal end portion of the sheath 30 and the insertion section 16 are connected to each other with a corded body 117.

That is, in this example, the hook-shaped knife 112 needs not to be inserted through a working channel 16a of the endoscope device 11, and the hook-shaped knife 112 may be connected to the endoscope device 11 to such a degree that the position of the hook-shaped knife 112 is clearly recognized within the body of the patient P.

In the manipulator system 5 configured in this way, when the hook-shaped knife 112 is gripped by the gripper 24A of the manipulator 19A, the gripper-side electrode 111 of the gripper 24A and the sheath-side electrode 115 of the hook-shaped knife 112 are electrically connected to each other.

The grip detector 110 detects whether or not the gripper-side electrode 111 of the manipulator 19A and the sheath-side electrode 115 of the hook-shaped knife 112 come into contact with each other. The grip detector 110 can detect the gripping state where the manipulator 19A grips the hook-shaped knife 112 in a state where the gripper-side electrode 111 and the sheath-side electrode 115 come into contact with each other, using well-known methods, such as measuring the electric resistance between the gripper-side electrode 111 and the sheath-side electrode 115 (applying an electric current therebetween) and measuring electrostatic capacitance.

The instrument controller 75 makes the high-frequency generator 200 output a high-frequency current in a case where the gripping state is detected when the foot switch 52 is pushed with a foot. The high-frequency current output from the high-frequency generator 200 flows to the knife part 31 via the cord 201, the gripper-side electrode 111, the sheath-side electrode 115, and the connecting wiring line 116. The knife part 31 of the hook-shaped knife 112 is pressed against the target tissue P3 to incise the target tissue P3.

According to the manipulator system 5 of the present embodiment configured in this way, the same effects as the manipulator system 4 of the embodiment can be exhibited. Moreover, since the hook-shaped knife 112 is not inserted through the working channel 16a of the endoscope device 11, the hook-shaped knife 112 can be handled more easily.

The present embodiment may include an instrument holder that can attach and detach the hook-shaped knife 112 to/from the distal portion of the insertion section 16 and can be removed and attached by the manipulators 19A and 19B within the body of the patient P. Particularly, in a case where a plurality of instruments that are not inserted through the working channels 16a are provided as in the hook-shaped knife 112, it is effective to perform a treatment while replacing these instruments within the body. That is, when an instrument is replaced within the body, the instrument can be replaced even if the insertion section 16 is not pulled out of the inside of the body of the patient P. Therefore, a procedure can be performed smoothly.

The grip detector provided in the manipulator system of the present embodiment is not limited to the grip detector 110 that detects the gripping state on the basis of the gripper-side electrode 111 and the sheath-side electrode 115 having come into contact with each other. For example, a configuration in which the gripping state where the manipulator 19A grips the hook-shaped knife 102 on the basis of the image in which the manipulator 19A and the hook-shaped knife 102 are captured, as in the grip detector 101 of the embodiment, and a configuration in which it is detected that the state between the pair of contacts 38 is the conduction state, as in the grip detector 32, may be adopted.

Sixth Embodiment

Next, although a sixth embodiment of the present invention will be described referring to FIGS. 15 and 16, the same parts as the above embodiment will be designated by the same reference numerals and the description thereof will be omitted, and only different points will be described.

The present embodiment is different from other embodiments in terms of the configuration of an instrument provided in the manipulator system.

Figure 15:
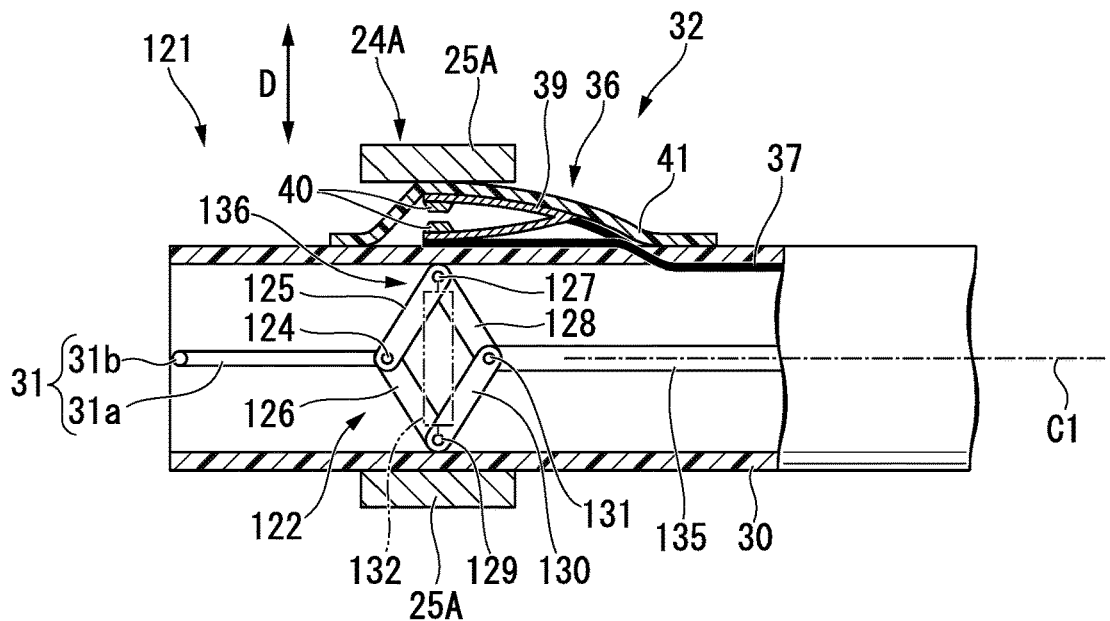
FIG. 15 is a side view of a distal side when a portion of a hook-shaped knife of a sixth embodiment of the present invention is broken.
Figure 16:
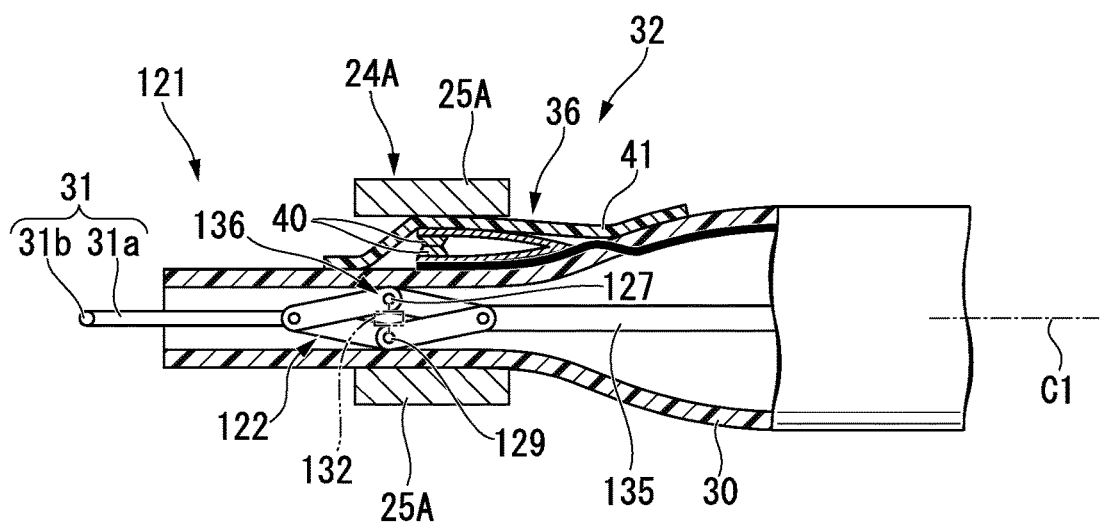
FIG. 16 is a side view of the distal side when a portion of the hook-shaped knife is broken, showing a state where the hook-shaped knife is gripped by a gripper.

As shown in FIG. 15, a hook-shaped knife 121 of the present embodiment includes an extendable mechanism 122 that is provided within the sheath 30 and that is capable of extending and contracting, and a supporting wire 135 having a distal portion connected to the extendable mechanism 122, in addition to the respective configurations of the hook-shaped knife 14 of the first embodiment.

The extendable mechanism 122 is a so-called link mechanism of the pantograph structure. The extendable mechanism 122 has a pair of distal-side link members 125 and 126 whose mutual distal portions are rotatable supported around a shaft member 124, a proximal end-side link member 128 whose distal portion is rotatably supported around a shaft member 127 provided at a proximal end portion of the distal-side link member 125, and a proximal end-side link member 130 whose distal portion is rotatably supported around a shaft member 129 provided at a proximal end portion of the distal-side link member 126. A proximal end portion of the proximal end-side link member 128 and a proximal end portion of the proximal end-side link member 130 are rotatably supported by a shaft member 131. The length of the distal-side link members 125 and 126 and the length of the proximal end-side link members 128 and 130 are set to be approximately equal to each other.

The shaft members 127 and 129 are biased by a spring member 132 so as to separate from each other. Accordingly, a state where proximal end portions of the distal-side link members 125 and 126, and distal portions of the proximal end-side link members 128 and 130 abut against the inner surface of the sheath 30 in a natural state is held.

The proximal end portions of the distal-side link members 125 and 126 and the distal portions of the proximal end-side link members 128 and 130 are equivalent to an action portion 136.

A distal portion of the supporting wire 135 is connected to the shaft member 131 so as to be rotatable with respect to the shaft member 131. A proximal end portion of the supporting wire 135 is connected to the slider 45. In this example, the slider 45 is fixed to the instrument operating part 33.

The proximal end portion of the knife body 31a of the knife part 31 is rotatably connected to the shaft member 124 of the extendable mechanism 122. In the natural state, the knife part 31 is housed within the sheath 30.

The switch 36 of the above grip detector 32 is provided on the outer surface of the sheath 30. The axis C1 side of the sheath 30 with respect to the action portion 136 and the reference direction D are set so as to become parallel to each other. The grip detector 32 is provided so that the position of the switch 36 of the grip detector 32 and the position of the extendable mechanism 122 match each other in the direction of the axis C1.

In the hook-shaped knife 121 configured in this way, as shown in FIG. 15, the pair of grip pieces 25A of the manipulator 19A are arranged so as to pinch the switch 36 and the extendable mechanism 122 in the radial direction of the sheath 30. As shown in FIG. 16, if the pair of grip pieces 25A are operated so as to come close to each other, the action portion 136 moves to the axis C1 side, and the shaft member 127 and 129 are brought close to each other against the biasing using the spring member 132. The shaft member 124 moves to the distal side with respect to the supporting wire 135 (the extendable mechanism 122 is extended in the direction of the axis C1), and the hook portion 31b of the knife part 31 protrudes from the sheath 30.

Additionally, at this time, the pair of electrodes 40 come into contact with each other, and the state between the pair of contacts 38 is switched from the cutoff state to the conduction state.

If the pair of grip pieces 25A are separated from each other, the shaft members 127 and 129 move so as to be separated from each other by the biasing force of the spring member 132, and as shown in FIG. 15, the knife part 31 is housed within the sheath 30.

According to the hook-shaped knife 121 of the present embodiment configured in this way, since the extendable mechanism 122 is included, the hook portion 31b protrudes from the sheath 30 only when the hook-shaped knife 121 is gripped by the gripper 24A of the manipulator 19A. Accordingly, a peripheral tissue can be kept from receiving load due to the hook portion 31b.

Since the knife part 31 is housed within the sheath 30 when the gripping state of the hook-shaped knife 121 by the manipulator 19A is released, a procedure can be performed more reliably.

Additionally, the axis C1 side with respect to the action portion 136 and the reference direction D are set so as to become parallel to each other. For this reason, when the switch 36 and the extendable mechanism 122 are pinched by the pair of grip pieces 25A, the extendable mechanism 122 can be extended in the direction of the axis C1, and the state between the pair of contacts 38 can be switched to the conduction state. That is, two operations of extending the extendable mechanism 122 and switching the state between the contacts 38 to the conduction state can be simultaneously performed as a series of operations simply by gripping by the gripper 24A.

The gripping state of the hook-shaped knife 121 by the manipulator 19A may be detected by the following method without including the hook-shaped knife 121 of the present embodiment in the grip detector 32.

For example, an image in which the knife part 31 protrudes from the sheath 30 may be acquired by the imaging unit 18, and the gripping state may be detected by applying the image analysis technique to this image. Additionally, a coil (not shown) is provided within the sheath 30. The gripping state may be detected as the metallic knife part 31 moves to this coil and the inductance (L) of the coil changes.

Although the first to sixth embodiments of the present invention have been described above in detail with reference to the drawings, specific configuration is not limited to the embodiments, and changes of the configuration are also included without departing from the scope of the present invention. Moreover, it is obvious that the respective configurations shown in the respective embodiments may be combined and used appropriately.

For example, in the first to sixth embodiments, the hook-shaped knifes are used as the instruments. However, the instruments are not limited to these and are not limited particularly if, for example, instruments, such as the high-frequency knife and the ultrasonic instrument, which are operated by applying an electric current or generating supersonic vibration, are used. The operation in this case generates supersonic vibration if the instrument is the ultrasonic instrument. Additionally, instruments having a movable part, which operates electrically such that the grip pieces are opened and closed by a motor in the gripping forceps, can be applied as the instruments of the present embodiments. As the operation in this case, the movable part moves.

In the first to fourth embodiments, the state between the pair of contacts is the cutoff state in the natural state, and the gripping state is detected by the state between the pair of contacts being the conduction state. However, the state between the pair of contacts is the conduction state in the natural state, and the gripping state may be detected by the state between the pair of contacts being the cutoff state.

In the first to fourth embodiments, a hook-shaped knife is held by the manipulator 19A by gripping the hook-shaped knife with the gripper 24A of the manipulator 19A. However, for example, a distal portion of the manipulator 19A may be formed with a convex portion, the hook-shaped knife 14 may be formed with a concave portion that engages this convex portion, and a hook-shaped knife may be held by the manipulator 19A as the convex portion and the concave portion engage each other. A configuration may be adopted in which a hook-shaped knife is held by the manipulator 19A as a rod-shaped portion of the manipulator 19A fits into a hole provided in the hook-shaped knife.

Additionally, a grip detector having a switch may be provided in the endoscope device 11. In this case, the switch can be provided on an inner surface of a grip piece 25A of the manipulator 19A.

In the first to sixth embodiments, the instruction-receiving part is the foot switch 52. However, the aspect of the instruction-receiving part is not limited, and may be, for example, a switch that is provided at a master arm 51 and operated by the hand of the operator O.

In the first to sixth embodiments, the manipulator system includes two sets of the manipulators 19A and 19B. However, the number of manipulators provided in the manipulator system is not limited, and may be one or may be three or more.

The conduction or cutoff between the pair of contacts 38 is switched by pressing the portion provided with the switch 36. However, the switching of the conduction or cutoff between the pair of contacts 38 is not limited to this method. For example, an electromagnet provided at the gripper 24A of the manipulator 19A may be brought close to a permanent magnet provided between the pair of contacts 38, and the conduction and cutoff between the pair of contacts 38 may be switched by switching whether or not an electric current is applied to this electromagnet.

In procedures using the manipulator systems of the first to fifth embodiments, the insertion section 16 of the endoscope device 11 is introduced from the mouth P1 of the patient P. However, parts that introduce the insertion section 16 may be other natural openings, such as the nose and the anus, or the insertion section may be introduced from an opening formed by incising the body wall of the patient P.

Additionally, medical actions using the manipulator system of the present invention may not be limited to the above-described treatments, and may be diagnosis or treatment actions.

In an instrument within an object described in Japanese Unexamined Patent Application, First Publication No. 2005-046361, the diameter of a tubular member becomes large in order to provide a plurality of peripheral holes. Therefore, there is a problem in that insertion into a patient becomes difficult and invasion becomes large. Additionally, there is also a problem in that a plurality of instruments interfere with each other and a procedure becomes complicated.

The following seventh and eighth embodiments are accomplished in view of the above problems, and provide a method and medical system that can efficiently deliver plurality of instruments from one channel. Moreover, another object of the seventh and eighth embodiments is to provide an introducer that can favorably deliver a plurality of instruments from one channel.

Seventh Embodiment

Figure 17:
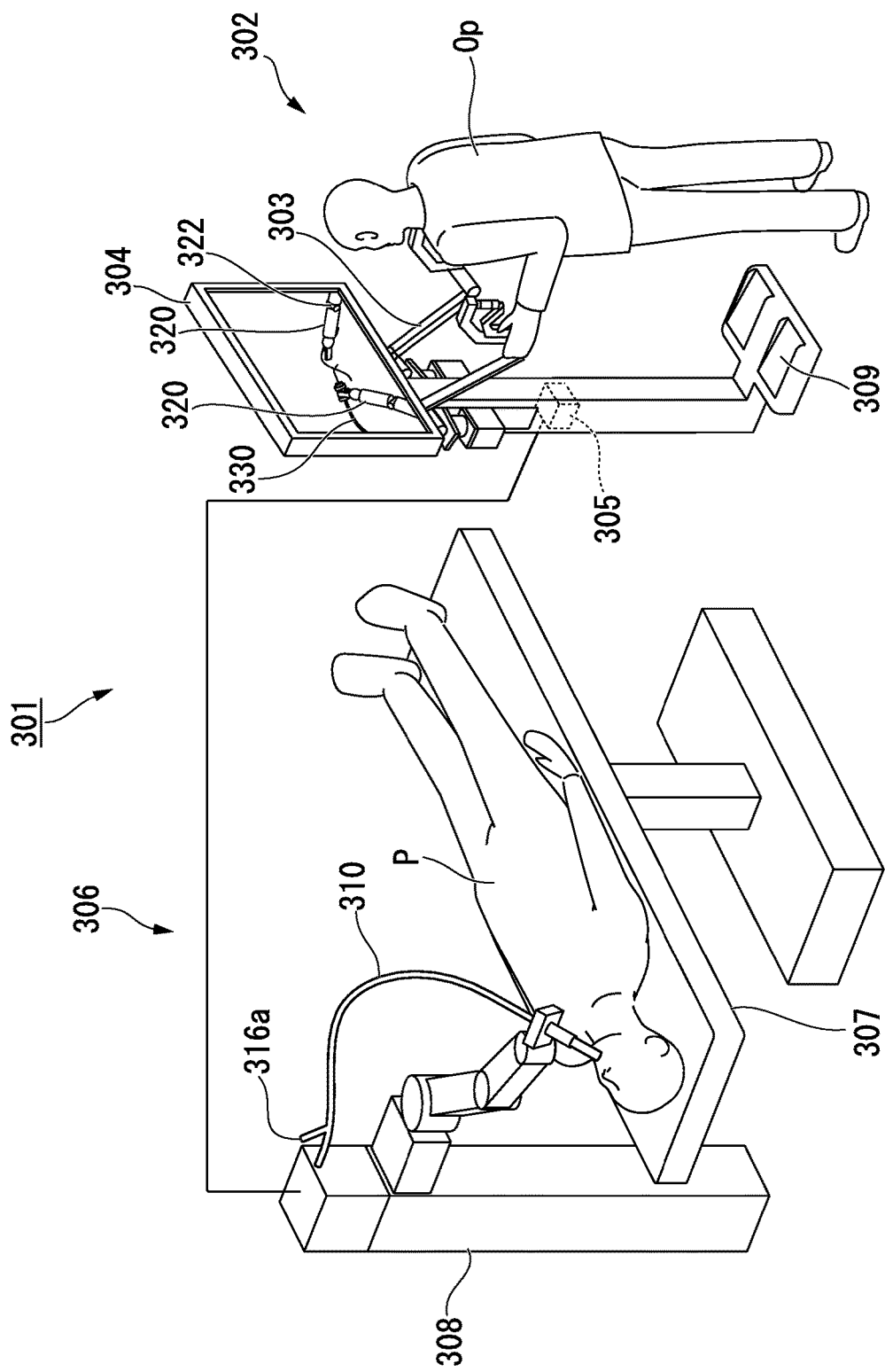
FIG. 17 is a view showing an overall configuration of a medical system related to a seventh embodiment of the present invention.

A seventh embodiment of the present invention will be described with reference to FIGS. 17 to 29. FIG. 17 is an overall view of a medical system of the present embodiment.

As shown in FIG. 17, a medical system 301 of the present embodiment is a so-called master slave type system including a master manipulator 302 operated by an operator Op, and a slave manipulator 306 provided with an endoscopic device 310.

The master manipulator 302 includes a master arm 303 with which the operator Op performs an operation input, a display unit 304 that displays an image captured using the endoscopic device 310, and a controller 305 that generates an operating command for operating the slave manipulator 306 on the basis of the operation of the master arm 303.

In the present embodiment, the master arm 303 is an operating part for operating respective parts of the slave manipulator 306 including a holding tool 320 (to be described below) that is attached to the endoscopic device 310. Additionally, although not shown in detail, the master manipulator 302 has a pair of the master arms 303 corresponding to the right hand and left hand of the operator Op, respectively. The master arm 303 has a multi-joint structure in order to operate joint parts 322 of the holding tool 320 having at least one degree of freedom. The end portion of the master arm 303 located on the operator Op side is provided with a gripper operating part (not shown) for operating a gripper 326 (to be described below) of the holding tool 320.

The display unit 304 is a device on which an image of a target part captured by an observation unit 315 (to be described below) attached to the endoscopic device 310 is displayed. The holding tool 320 and an instrument (to be described below) together the target part are also displayed on the display unit 304.

The slave manipulator 306 has a bed 307 on which the patient P is placed, a multi-joint robot 308 arranged in the vicinity of the bed 307, and the endoscopic device 310 attached to the multi-joint robot 308. The multi joint robot 308 and the endoscopic device 310 operate according to an operating command issued from the master manipulator 302.

Figure 18:
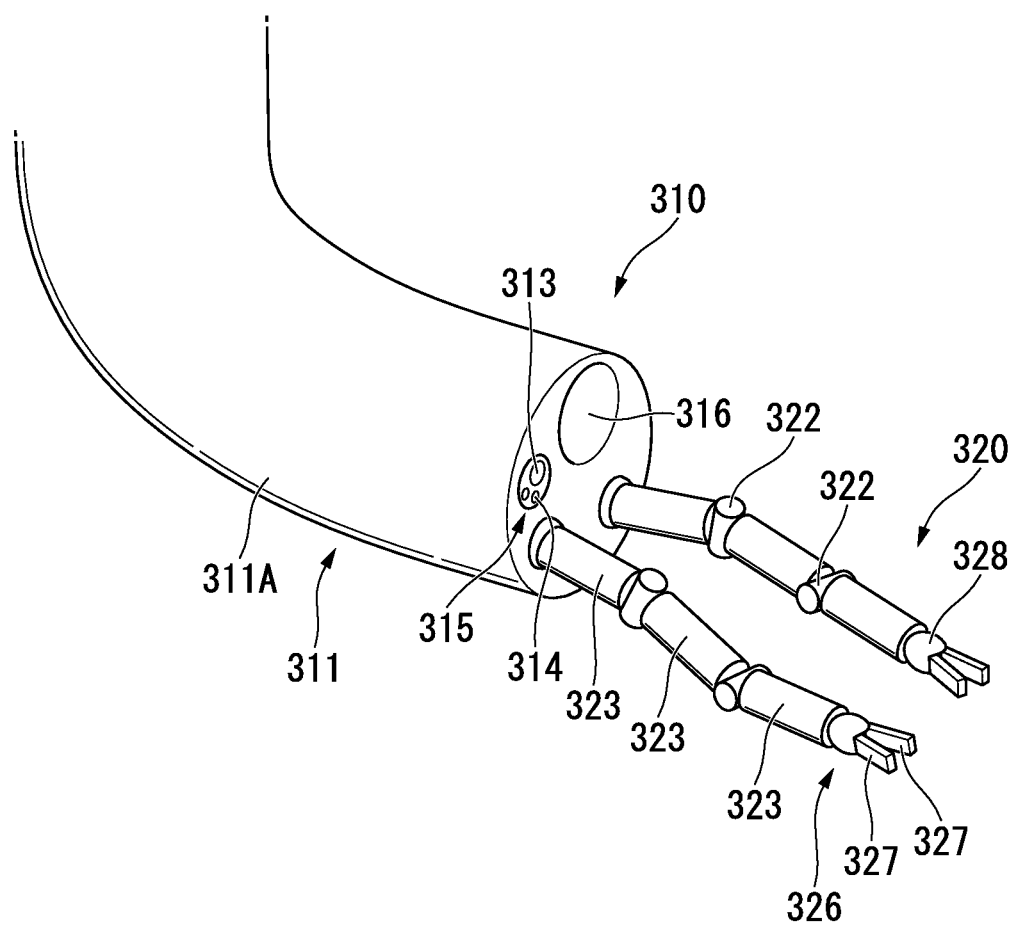
FIG. 18 is a view showing a distal portion of an endoscopic device in the medical system.

In the medical system of the present embodiment, a multi joint robot is not indispensable, and for example, a configuration in which an assistant (not shown) holds the endoscopic device 310 may be adopted. FIG. 18 is a perspective view showing the distal portion of the endoscopic device 310 inserted into the body of the patient P. As shown in FIG. 18, the endoscopic device 310 has a tubular member 311 (insertion section) having flexibility, and a pair of holding tools 320 are attached to a distal end of the tubular member 311.

The tubular member 311 is a longitudinal member inserted into the body of the patient P. The tubular member 311 has a well-known bending mechanism 311A including joint rings, bending pieces, or the like, and can change the orientation of its distal portion by bending the bending mechanism 311A with an operation input to a master arm 303.

Additionally, the tubular member 311 has an instrument channel 316 that is a path for delivering an instrument, and the observation unit 315. The instrument channel 316 opens to the distal of the tubular member 311. The instrument channel 316 also opens to a proximal end portion of the tubular member 311, and the opening is a delivery port 316a (refer to FIG. 17) for an instrument.

The observation unit 315, which is a device for observing a target part, has a well-known configuration including an imaging mechanism 313 and an illumination mechanism 314. In the present embodiment, the observation unit 315 is fixed to the distal portion of the tubular member 311. However, the observation unit may be enabled to be advanced and retracted with respect to the tubular member or may be enabled to be bent, by using a well-known endoscope as the observation unit and inserting the endoscope through a channel for observation means provided in the tubular member.

Each holding tool 320 includes the joint parts 322 turned by the operation of the master arm 303, the gripper 326 (holder) attached to the joint part 322, and long tubular parts 323 that connect the joint parts 322 together or connect the joint part 322 and the gripper 326 together.

The gripper 326 has a pair of gripper members 327 for holding an instrument. The gripper members 327 are opened and closed by operating the gripper of the master arm 303. Additionally, the gripper 326 is further provided with a biaxial joint 328 for adjusting the orientation of the gripper 326 on the distal side of the holding tool 320.

The holding tool 320 with the above configuration can perform a desired procedure by driving the joint parts 322 and the joint 328 while gripping an instrument with the gripper 326. Additionally, each holding tool 320 can be advanced and retracted with respect to the tubular member 311 and can be housed within the tubular member 311.

In the medical system of the present embodiment, various changes may be made to the holding tool 320. For example, the number or degree-of-freedom of the joint parts may be appropriately set in consideration of the contents of a procedure, or the like. Additionally, the same mechanism as the above-described bending mechanism 311A may be used instead of the combination of the joint part and the tubular part. Moreover, the number of the holding tools may be one or more arbitrary numbers. The mechanisms for driving the joint parts or gripper or advancing and retracting the holding tool with respect to the tubular member are not limited particularly. For example, well-known mechanisms including an actuator, such as a motor, and a transmission member, such as a wire, which transmits a driving force, can be used.

Figure 19:
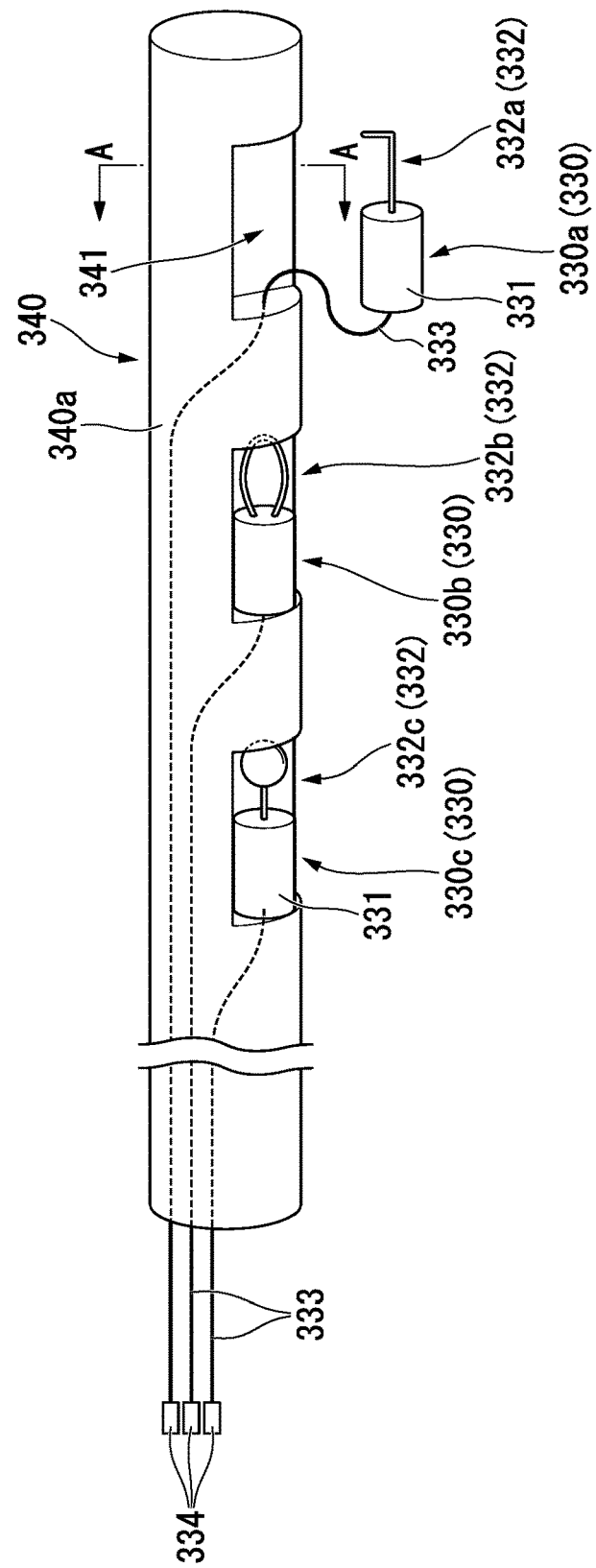
FIG. 19 is a perspective view of an instrument introducer in the medical system.

FIG. 19 is a view showing an instrument and an instrument introducer (hereinafter referred to as an "introducer") for delivering the instrument. The introducer 340 includes a main body 340a formed in a substantially columnar shape with a diameter such that the main body can be inserted into the instrument channel 316. The main body 340a has a rigidity such that the main body can be advanced and retracted within the instrument channel 316 and a flexibility such that the main body can follow meandering of the instrument channel 316 accompanying the bending of the tubular member 311. As a surface material of such a main body 340a, resin is suitable, and fluorine-based resin or the like can be used in consideration of biocompatibility or the like.

Figure 20:
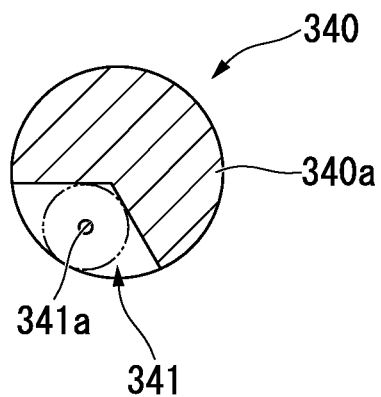
FIG. 20 is a cross-sectional view in line A-A of FIG. 19.

Since an outer peripheral surface of the main body 340a is provided with a plurality of concave portions 341, it is possible to hold instruments 330 in a state where the instruments are housed in the respective concave portions 341. The respective concave portions 341 are provided side by side in the direction of the axis of the main body 340a, and as shown in FIG. 20, are formed so that the cross-section of the main body 340a in the axial direction has substantially a sector shape. However, the shape of the concave portions is not limited particularly. However, if the shape of the concave portions is set so that the instruments housed in the concave portions does not protrude from the outer peripheral surface of the introducer, this is preferable because advance and retraction of the introducer to be described below are easily performed.

Each instrument 330 includes a substantially rod-shaped grip 331, and a treatment part 332 attached to a distal portion of the grip 331. Although three instruments 330a, 330b, and 330c each including a hook-shaped knife 332a, a snare 332b, and a ball-tip type knife 332c are shown as treatment parts in FIG. 19, the type of the treatment parts is not limited to this. For example, it is natural that treatment parts in various well-known instruments for endoscopes can be adopted.

A cable 333 is attached to a proximal end side of the grip 331 of each of the instruments 330a, 330b and 330c. The cable 333 enters an internal space of the introducer 340 through a hole 341a formed in the wall surface of each concave portion 341 on the proximal end side, and protrudes from a proximal end portion of the introducer 340. Distal sides of the respective cables 333 are electrically connected to the treatment parts, respectively, and plug 334s for connection with terminals (not shown) of the multi-joint robot 308 are provided on proximal end sides of the cables.

The operation when the medical system 301 with the above configuration is used will be described. First, in a state where the pair of holding tools 320 are housed within the tubular member 311, the distal portion of the tubular member 311 is inserted into the body of the patient P and advanced to near a target part. Next, while checking an image of an operative field acquired by the observation unit 315 with the display unit 304, the operator Op operates a master arm 303 to cause a holding tool 320 protrude from the tubular member 311.

When a treatment is performed on the target part using a plurality of instruments, the instrument are fed using the introducer 340. A flow of an instrument delivery method of the present embodiment using the introducer 340 will be described.

The operator Op or assistant (not shown) houses the instruments 330a to 330c in the respective concave portions 341 of the introducer 340, and holds the three instruments within the concave portions 341, for example, by pulling the cables 333 to the proximal end side. Next, the plugs 334 of the respective cables 333 are connected to the terminals of the multi-joint robot 308, and the distal of the introducer 340 is inserted into the instrument channel 316 from the delivery port 316a.

The above step is a first step of simultaneously inserting the plurality of instruments into one instrument channel. In the present invention, the term "simultaneously inserting" does not means that the timing with which a plurality of instruments enters the instrument channel is simultaneous, but means that a plurality of instruments are inserted so that a state where the instruments are simultaneously present within the instrument channel.

The first step may be performed before the tubular member 311 is inserted into the patient P. Additionally, in the first step, any of the insertion of the introducer 340 into the instrument channel 316 and the connection between the plugs 334 and the terminals may be performed first.

Figure 21:
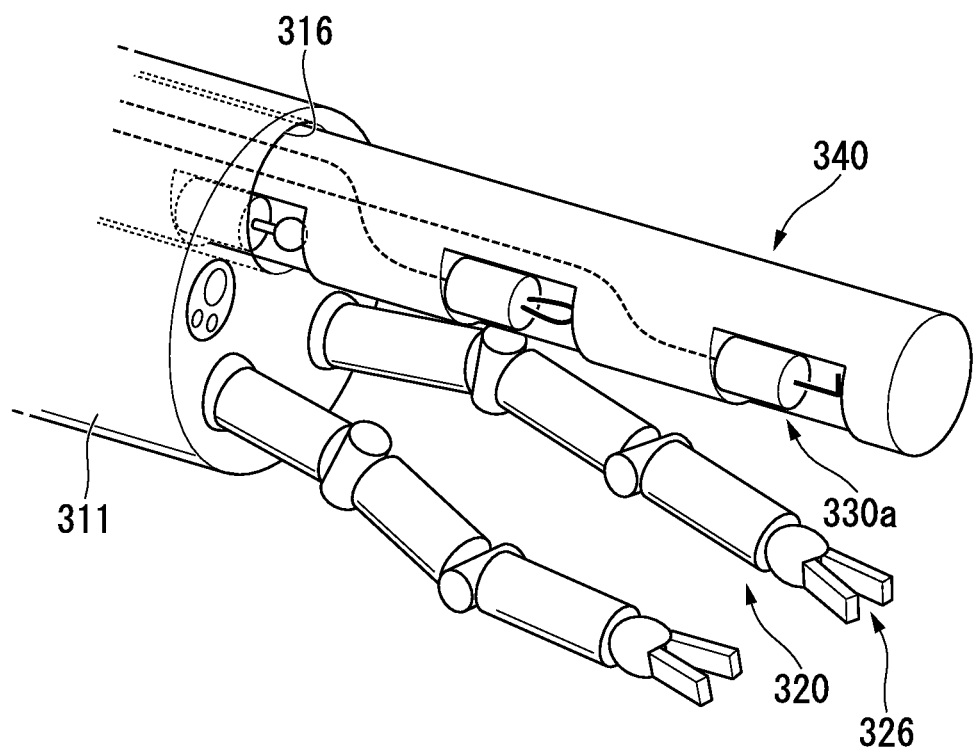
FIG. 21 is a view showing the operation when the medical system is used.

Next, the assistant advances the introducer 340 with respect to the tubular member 311 to cause the tubular member to protrude from the instrument channel 316 as shown in FIG. 21, and moves an instrument to be used, for example, the instrument 330a to near the gripper 326 of a holding tool 320.

The above step is a second step of advancing the introducer to move at least one instrument to the front of the tubular member.

Figure 22:
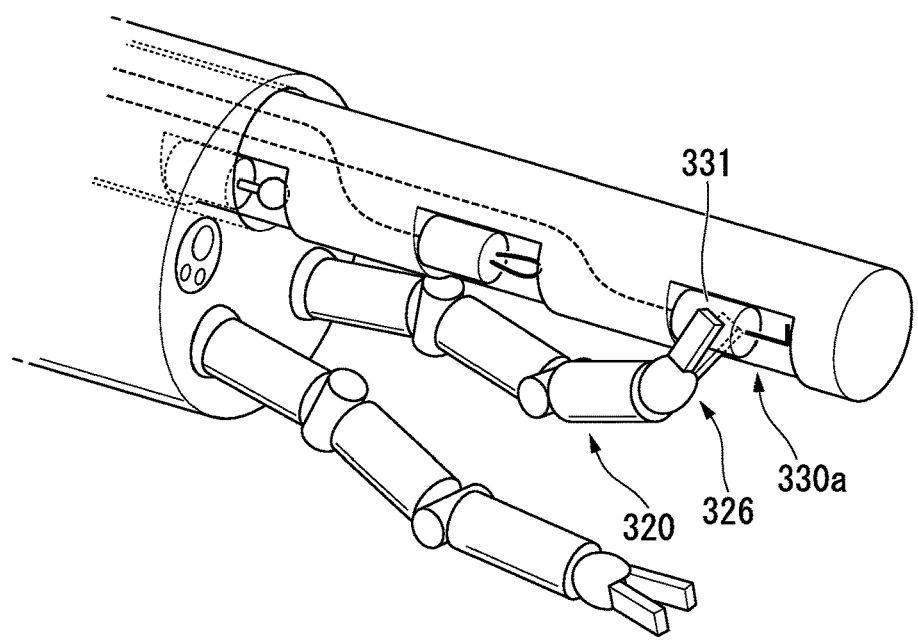
FIG. 22 is a view showing the operation when the medical system is used.

The operator Op operates the holding tool 320 with a master arm 303 while checking the instrument 330a with the display unit 304, and as shown in FIG. 22, holds the grip 331 of the instrument 330a with the gripper 326.

Figure 23:
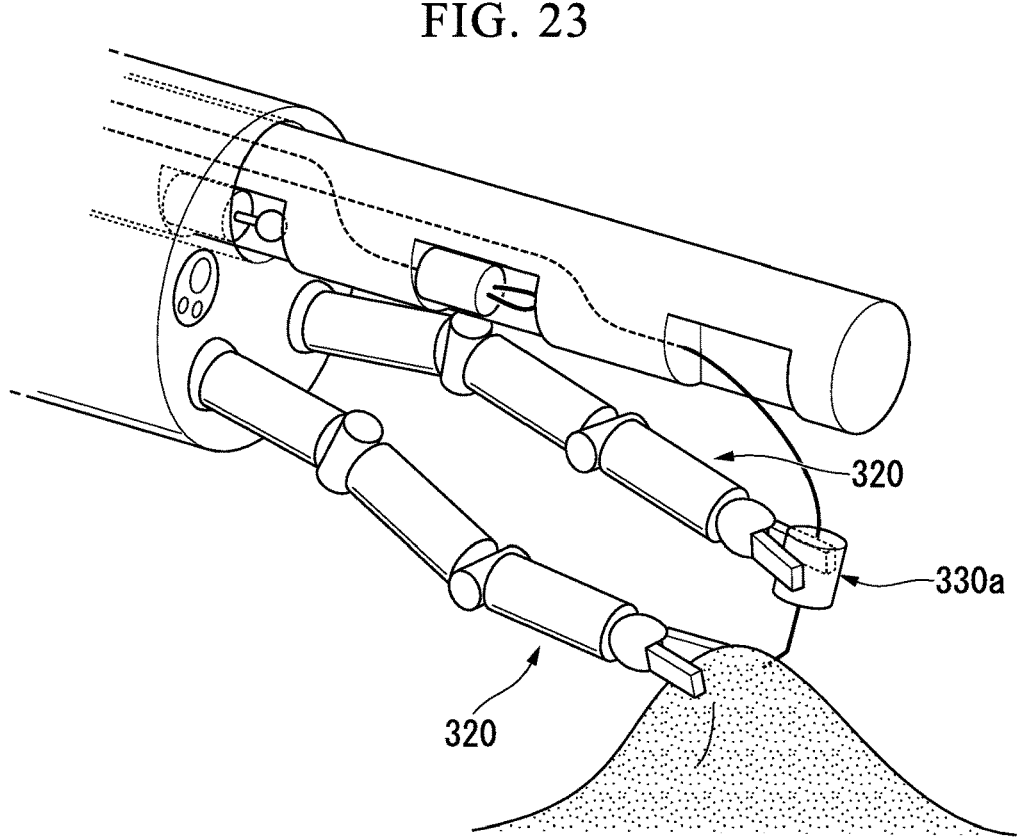
FIG. 23 is a view showing the operation when the medical system is used.

Thereafter, the operator Op performs an appropriate procedure on the target part as shown in FIG. 23, using the pair of holding tools 320 and the instrument 330a. If the foot switch 309 (refer to FIG. 17) of the master manipulator 302 is stepped on when an electric current is applied to the treatment part, a high-frequency current or the like is supplied to the treatment part from a cable 333.

When the operator Op replaces an instrument, the assistant advances and retracts the introducer 340 to move the introducer to a position where an instrument to be used next is easily gripped by the gripper 326, and then, the operator Op operates the gripper 326 to grip the instrument again. The instrument that is being used may be housed within the concave portion 341 again, for example, by pulling the cable 333 to the proximal end side, or may be put out of the concave portion if a procedure is not hindered. Additionally, and a procedure may be performed with an instrument being gripped by each of the pair of holding tools 320.

If the procedure is finished, the operator Op releases the gripping of the instruments by the grippers 326 and houses the holding tool 320 within the tubular member 311. Then, the tubular member 311 is removed from the patient P, and a series of treatment is ended. In this case, the plurality of instruments 330 may be housed within the concave portions 341 of the introducer 340 and housed within the instrument channel 316, or the tubular member may be removed in a state where the plurality of instruments are held to such a degree that the instruments are not popped out in the radial direction of the tubular member 311 in the front of the tubular member 311, for example, by towing the cables 333.

As described above, according to the instrument delivery method of the present embodiment, the plurality of instruments 330 are simultaneously inserted into one instrument channel 316 in the first step. Therefore, if all instruments scheduled to be used for a treatment are inserted into the instrument channel, even when an instrument is replaced during a procedure, the replacement can be easily performed in a short time without removing an instrument, which is being used, from the instrument channel.

Additionally, according to the introducer 340 of the present embodiment, the main body 340a having the plurality of concave portions 341 on the outer peripheral surface of the introducer is provided. Therefore, by housing and holding the plurality of instruments 330 into the plurality of concave portions 341, the plurality of instruments can be simultaneously inserted into one instrument channel without interference. Accordingly, although the medical system 301 in which the introducer 340 is combined has the configuration having only one instrument channel, the instrument delivery method of the present invention can be performed favorably. As a result, the diameter of the tubular member inserted into a patient can be made small, both a mechanism that observes a target part and a mechanism that performs a treatment can be introduced through a hole provided in one natural opening, the abdominal wall, or the like, and invasion of the patient can be reduced markedly.

The introducer of the present embodiment is not limited to the above-described introducer 340, and various configurations can be adopted. A portion of a modification example of the introducer will be described below. In addition, in the following description, components common to those already described will be designated by the same reference numerals, and duplicate description will be omitted.

In the introducer 340, the columnar or rod-shaped main body is formed with the concave portion 341 and the internal space through which the cable passes. However, when the diameter of members is small, the process of forming the concave portions, the internal space, or the like may become complicated. Thus, if the introducer is formed by using a tubular member as the main body, the instruments can be housed inside the introducer simply by boring holes in the outer peripheral surface, and it is also not necessary to newly form a space through which the cables or the like are passed. Therefore, the introducer is simple. However, it may be difficult to hold the instruments at predetermined positions within the introducer. Schematic views of an introducer of a modification example that solves this problem while the introducer is formed from the tubular member are shown in FIGS. 24 and 25.

Figure 24:
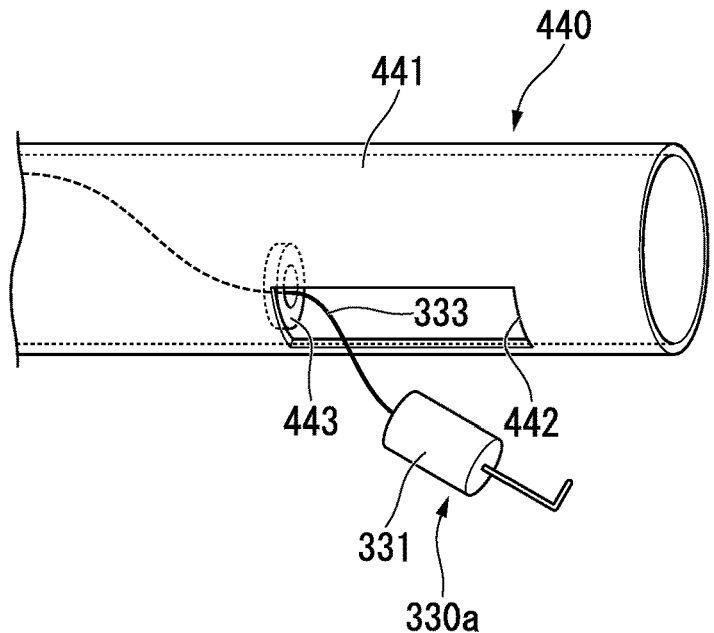
FIG. 24 is a view showing a modification example of the instrument introducer.

In an introducer 440 shown in FIG. 24, a hole 442 communicating with an internal space is provided in an outer peripheral surface of a main body 441 made of a tubular member so as to be able to house the instrument 330a. Moreover, an annular holding member 443 is attached to the inner wall of the hole 442 on the proximal end side. The internal diameter of the holding member 443 can be smaller than the external diameter of the grip 331 so that the grip 331 cannot pass through the holding member. A cable 333 connected to the grip 331 passes through the holding member 443 and extends to the proximal end side.

In the introducer 440, if the cable 333 is towed to the proximal end side, the proximal end side of the grip 331 comes into contact with the holding member 443. Moreover, since the grip 331 cannot pass through the holding member 443 even if the cable 333 is further towed, the instrument 330a stays in a part where the hole 442 is formed, and is held within the introducer 440.

Figure 25:
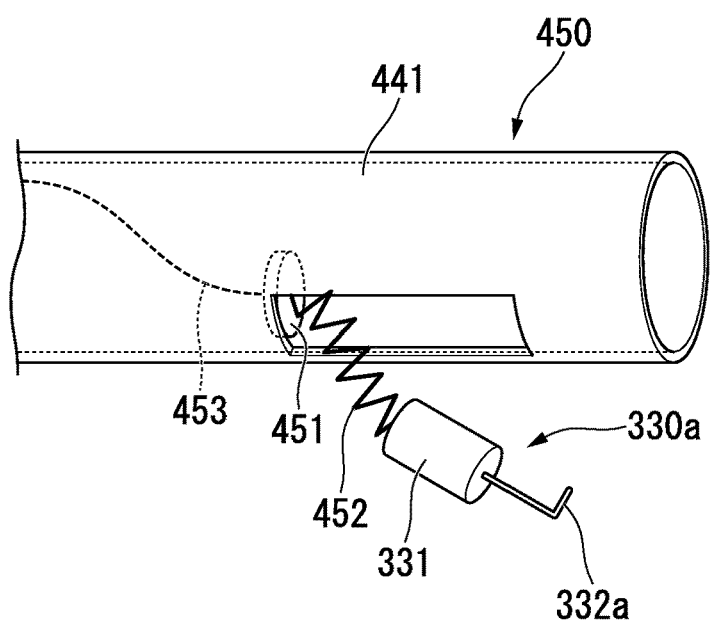
FIG. 25 is a view showing a modification example of the instrument introducer.

In an introducer 450 shown in FIG. 25, a holding member 451 is attached instead of the holding member 443. The grip 331 of the instrument 330a and the holding member 451 are connected to each other with a spring 452 formed from a conductor. Electric power is supplied to the hook-shaped knife 332a, which is a treatment part, via the cable 453 and spring 452 that are connected to the holding member 451.

In the introducer 450, if the gripping of the holding tool 320 that is gripping the instrument 330a is released, the instrument 330a returns to an initial position in the vicinity of the holding member 451 due to the elastic force of the spring 452. Accordingly, the operation of returning the instrument in instrument replacement can be made easy or unnecessary, and the instrument replacement can be made simpler.

Figure 26:
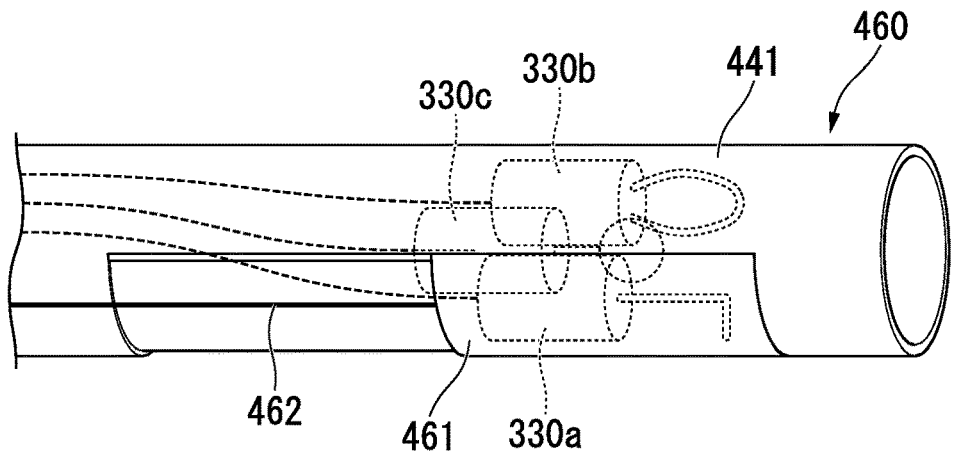
FIG. 26 is a view showing another modification example of the instrument introducer.
Figure 27:
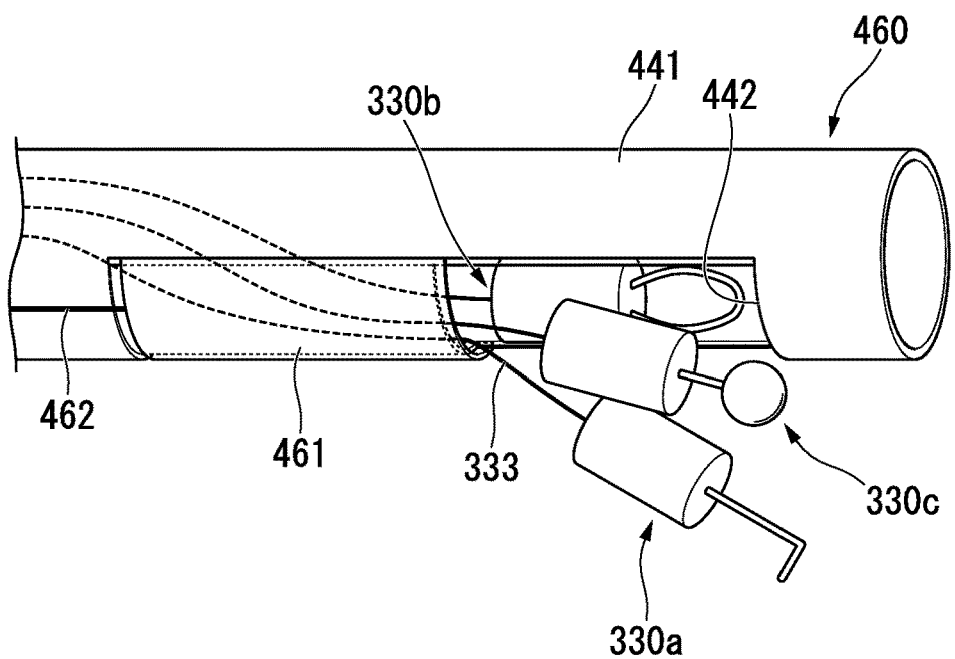
FIG. 27 is a view showing still another modification example of the instrument introducer.

An introducer 460 shown in FIGS. 26 and 27 is also formed using the tubular main body 441. The introducer 460 is configured by providing the main body 441 with the hole 442 and attaching a shutter 461, which opens and closes the hole 442, slidably with respect to the main body 441.

A plurality of instruments (the instruments 330a to 330c are shown as an example in FIGS. 26 and 27) are collectively housed in an internal space of the introducer 460. Thus, if the shutter 461 is opened with the hole 442 turned downward (in the direction of gravitational force), the instruments, as shown in FIG. 27, come out from the hole 442, and are brought into a state where the instruments can be gripped by the holding tools 320.

The introducer 460 has advantages in that structure is simple and manufacture is easy. Additionally, by towing the cables 333, the instruments can be easily housed in the internal space. In addition, although an example where an opening and closing wire 462 is attached to the shutter 461 is shown in FIG. 26, a configuration may be adopted in which the shutter is supported on the main body with a guide or the like without using the wire and the shutter is gripped and opened and closed by a holding tool.

Figure 28:
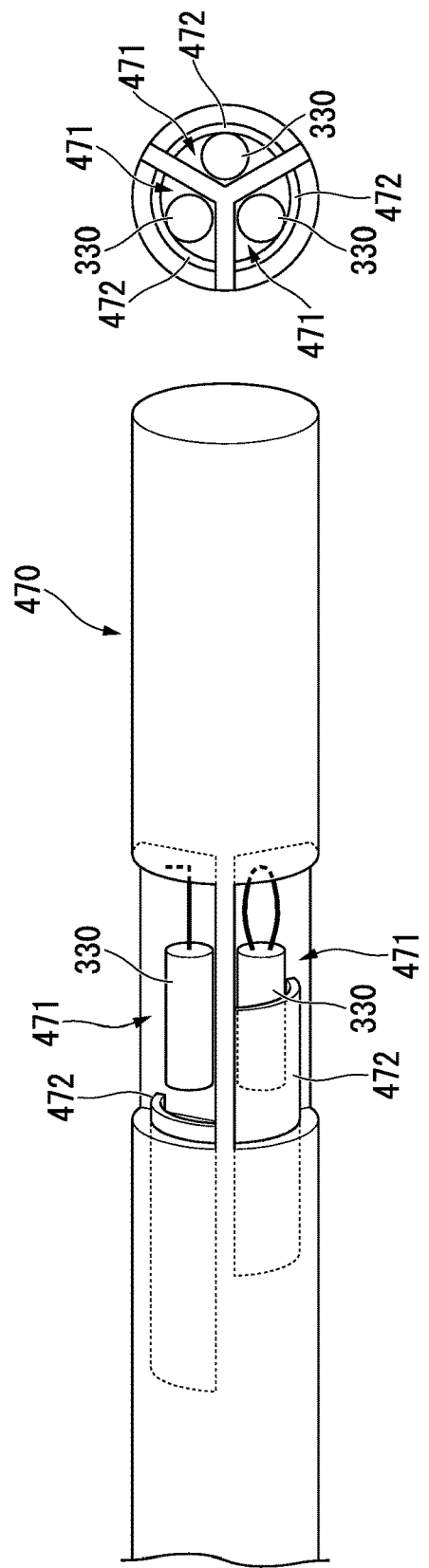
FIG. 28 is a view showing a still further modification example of the instrument introducer.
Figure 29:
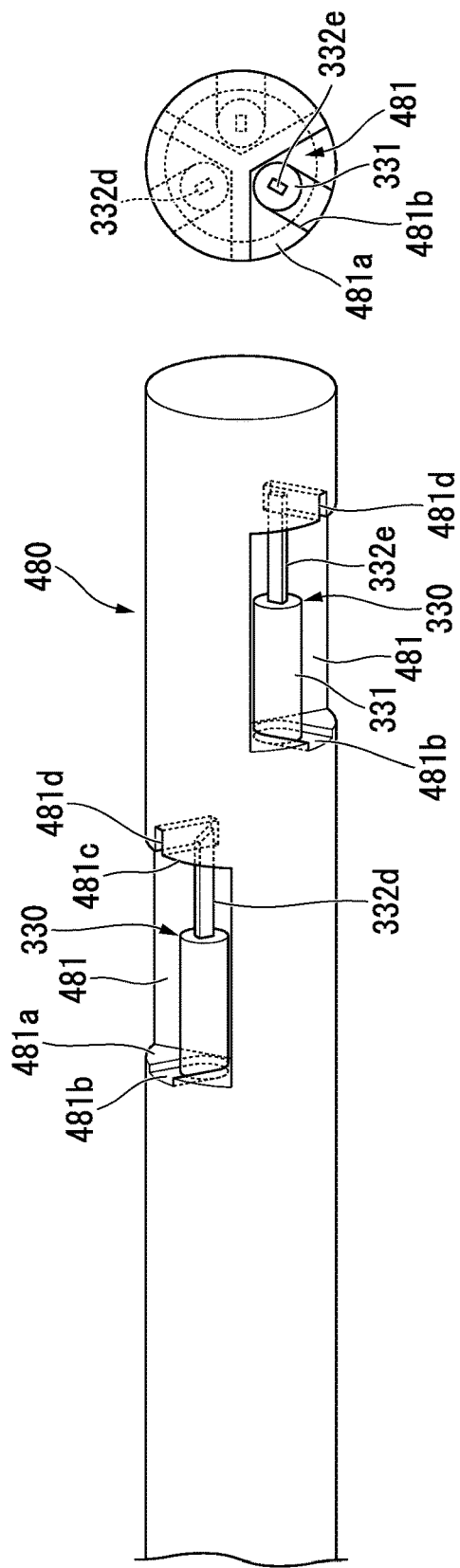
FIG. 29 is a view showing a still further modification example of the instrument introducer.

A modification example in which spaces that house instruments are arranged side by side in the circumferential direction of an introducer is shown in FIGS. 28 and 29.

In an introducer 470 shown in FIG. 28, three concave portions 471 are arranged side by side in the circumferential direction. A shutter 472 is provided in each concave portion. When the instruments 330 are fed using the introducer 470, the introducer 470 is rotated around an axis to make an adjustment so that the concave portions 471 that house required instruments come to positions where access of the holding tools 320 is easy. By closing the shutters 472, the instruments 330 are prevented from falling from the concave portions 471 even if the introducer 470 is rotated.

A modification example shown in FIG. 29 is an example in which an instrument that does not include the cables 333 is fed. In an introducer 480 shown in FIG. 29, while three concave portions 481 are arranged in the circumferential direction, the concave portions are arranged such that the positions thereof in the direction of the axis are made different. Such an arrangement is effective, for example, when instruments are large compared to the introducer and it is difficult to arrange all required concave portions such that the positions thereof in the direction of the axis are made to match each other.

Treatment parts of the instruments 330 to be fed in the present modification example, as shown in FIG. 29, include a cold knife 332d that does not require power supply, a retractor 332e, and the like. A wall surface 481a of each concave portion 481 on the proximal end side is formed with the diameter of the grip 331 of the instrument 330 and a groove 481b of the same width. A groove 481d is formed in a wall surface 481c of each concave portion 481 on the distal side in conformity with the width, thickness, or the like of a treatment part of each instrument 330. By inserting a proximal end side of the grip 331 into the groove 481b and causing the treatment part to enter the groove 481d to house the instrument in the introducer 480, the instrument 330 can be locked within the concave portion 481 while determining the orientation of the treatment part when being housed.

It is natural that this locking mechanism can be appropriately applied to the above-described other introducers. Additionally, the mechanism that locks the instrument to the concave portion is not limited to this, and various well-known locking structures can be applied.

Eighth Embodiment

An eighth embodiment of the present invention will be described. This embodiment is an example in which the instrument delivery method of the present invention is executed without using an introducer.

Figure 30:
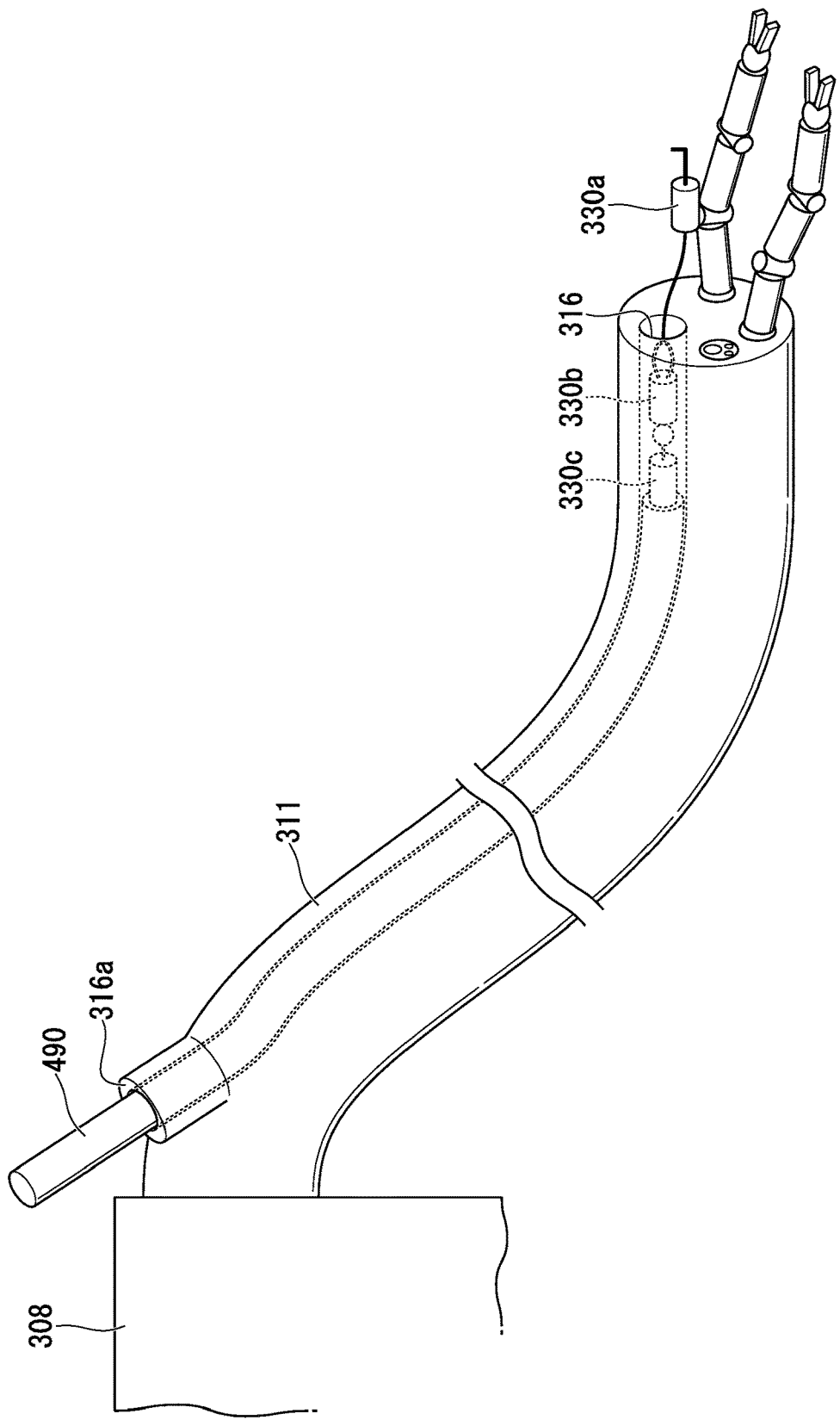
FIG. 30 is a view showing the operation when a medical system related to an eighth embodiment of the present invention is used.

FIG. 30 is a schematic view showing a second step in the present embodiment. In the present embodiment, in a first step, the plurality of instruments 330a to 330c are inserted into the instrument channel 316 from the delivery port 316a side by side in the direction of the axis. Thereafter, the assistant inserts a rod-shaped pusher 490 from the delivery port 316a. In the second step, the instruments inserted side by side as shown in FIG. 30 are moved to the front of the tubular member 311 in order by advancing the pusher 490.

The pusher 490 has the rigidity such that the instruments can be pushed out, and flexibility such that the pusher can follow meandering of the instrument channel. The same material as sheaths of general instruments for endoscopes can be used the material of the pusher 490. Additionally, the pusher 490 may be tubular as long as the pusher can push out the instruments. Even in the present embodiment, similar to the seventh embodiment, a replacement can be easily performed in a short time without removing an instrument, which is being used, from the instrument channel.

Figure 31:
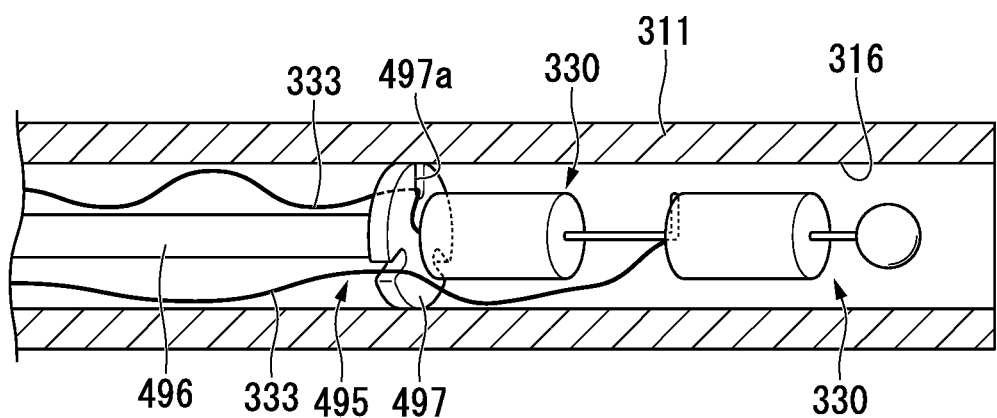
FIG. 31 is a view showing a modification example of a pusher in the medical system.

A modification example of the pusher used in the present embodiment is shown in FIG. 31. A pusher 495 includes a rod-shaped main body 496 and a pressing member 497 attached to the distal of the main body 496. Since the external diameter of the main body 496 is smaller than the internal diameter of the instrument channel 316, friction or interference with the cables 333 connected to the instruments 330 is not easily caused. The pressing member 497 is a substantially disk-shaped member, and the diameter of the pressing member is larger than the main body 496 and is made slightly smaller than the internal diameter of the instrument channel 316. Additionally, a cutout 497a is formed at a peripheral edge portion of the pressing member 497 to prevent interference with the cables 333. If such a pusher 495 is used, the second step can be performed more favorably.

While the present invention has been described above using the embodiments and modification examples, the technical scope of the present invention is not limited to the above embodiments. Combinations of constituent elements can be changed, various alternations can be added to respective constituent elements, or omissions can be made, without departing from the concept of the present invention.

For example, as the structure of the holders that hold the instruments in the holding tools, a configuration using a magnetic force or the like instead of the above-described gripper may be adopted.

For example, the instruments used in the present invention are not limited to those used by applying an electric current to the treatment parts, and instruments, such as a cold cutter, can also be used. When such instruments are fed, the cables are not indispensable. When there is no cable, it is difficult to return an instrument to the instrument channel after the end of a treatment. However, all the instruments may be housed, for example, using a holding tool for a net for recovery, and an endoscopic device may be removed from a patient in a state where the instruments are gripped by the holding tool.

Additionally, the cables may have functions other than supply of electric power or prevention of dropping of the instruments. For example, when an instrument includes a syringe needle, a hollow cable is connected to the instrument. Fluids, such as a medical fluid, can be supplied to the instrument by this cable.

Additionally, although an example in which advance and retraction of the introducers or the pushers are performed by an assistant has been described in the above-described respective embodiments, it is possible to automate this in the medical system. In this case, for example, drive mechanisms, such as actuators that generate driving forces for advance and retraction or rotation around the axis, can be provided so as to be operable from the master manipulator. Additionally, when the introducer 340 or the like in which the concave portions and the instrument correspond one-to-one with each other is used, an encoder that detects the amount of advance and retraction or the amount of rotation may be provided in the medical system. In this case, by giving to the controller information, such as the type of the instruments housed in the respective concave portions, or the amount of advance and retraction of the introducer, the amount of rotation of the introducer, or the like, which is required to move the respective concave portions to positions suitable for replacement, it is possible to drive the introducer by an amount required to move an instrument to be used next, to a position where the holding tool is enabled to hold the instrument, thereby automating the second step.

Additionally, although the master-slave type medical system has been described in the above-described embodiment, the medical system of the present invention is not limited to a medical system that performs a remote operation as in the master slave type. Accordingly, an operating part that the operator performs an operation input may be directly connected to a mechanism that performs the treatment of the endoscopic device or the like.

In the technique described in U.S. Pat. No. 7,083,571, when more instruments than the number of arms are used, it is necessary to perform replacement for attachment and detachment of the instruments with respect to the arms, and this replacement is complicated. Additionally, in the technique of U.S. Pat. No. 6,309,397, since a part that performs the operation of an end effector tool and a part that performs the operation of an arm are separate, it is hard to operate both of the parts when being apart from each other. Additionally, since an end effector should continue to be held in the arm, actual operation is not easy.

In light of the above-described problems, the object of the following ninth and tenth embodiments is to provide a medical manipulator that can easily perform an operation, though the medical manipulator has a configuration in which an instrument is replaceably held by an arm.

Ninth Embodiment

Figure 32:
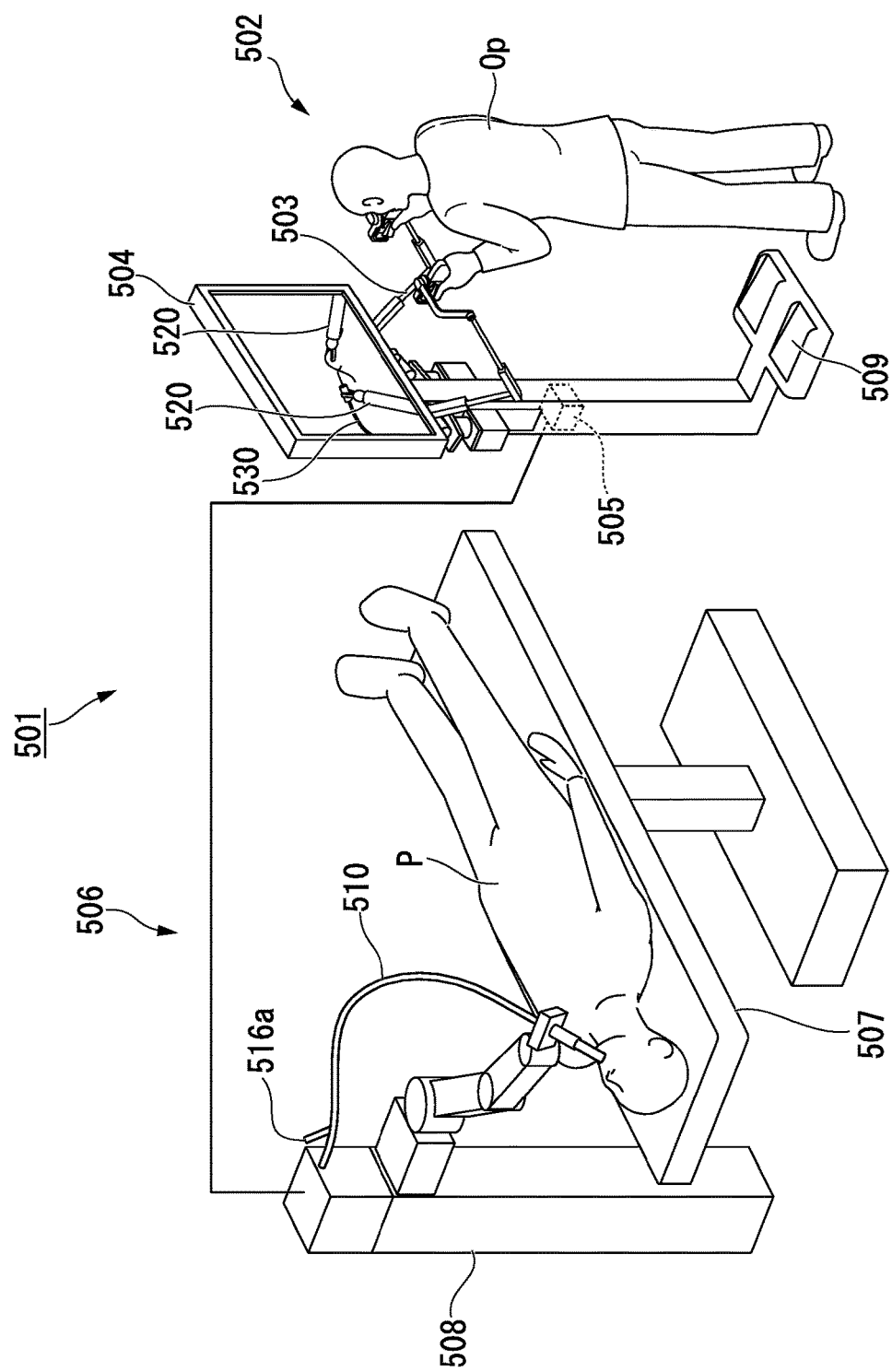
FIG. 32 is a view showing an overall configuration of a medical manipulator related to a ninth embodiment of the present invention.

A ninth embodiment of the present invention will be described with reference to FIGS. 32 to 40. FIG. 32 is an overall view of a medical manipulator of the present embodiment.

As shown in FIG. 32, a medical manipulator 501 of the present embodiment is a so-called master slave type manipulator including a master manipulator 502 operated by the operator Op, and a slave manipulator 506 provided with an endoscopic device 510.

The master manipulator 502 includes a master arm 503 with which the operator Op performs an operation input, a display unit 504 that displays an image captured using the endoscopic device 510, and a controller 505 that generates an operating command for operating the slave manipulator 506 on the basis of the operation of the master arm 503.

In the present embodiment, the master arm 503 is a mechanism for operating respective parts of the slave manipulator 506 including a holding tool 520 (to be described below) that is attached to the endoscopic device 510. The master manipulator 502 has a pair of the master arms 503 corresponding to the right hand and left hand of the operator Op, respectively. The master arm 503 has a multi-joint structure in order to operate the holding tool 520 having at least one degree of freedom.

Figure 33:
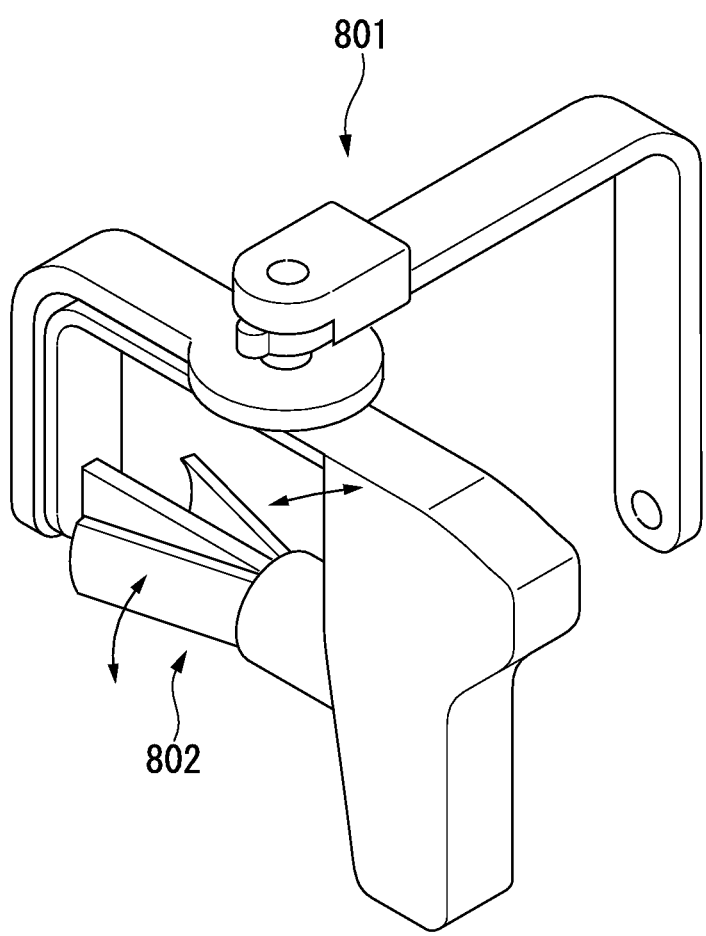
FIG. 33 is a view showing an operating part provided in a master arm of the medical manipulator.

FIG. 33 is a view showing an operation unit 801 provided at the end portion of the master arm 503 located on the operator Op side. The operation unit 801 is provided with a knob part (holder action part) 802 for operating a gripper (to be described below) of the holding tool 520 or an instrument (to be described below) held by the gripper.

Referring back to FIG. 32, the display unit 504 is a device on which an image of a treatment target tissue captured by an observation unit (to be described below) attached to the endoscopic device 510 is displayed. The holding tool 520 and the instrument (to be described below) together with the treatment target tissue are also displayed on the display unit 504.

The slave manipulator 506 has a bed 507 on which the patient P is placed, a multi-joint robot 508 arranged in the vicinity of the bed 507, and the endoscopic device 510 attached to the multi-joint robot 508. The multi joint robot 508 and the endoscopic device 510 operate according to an operating command issued from the master manipulator 502.

Figure 34:
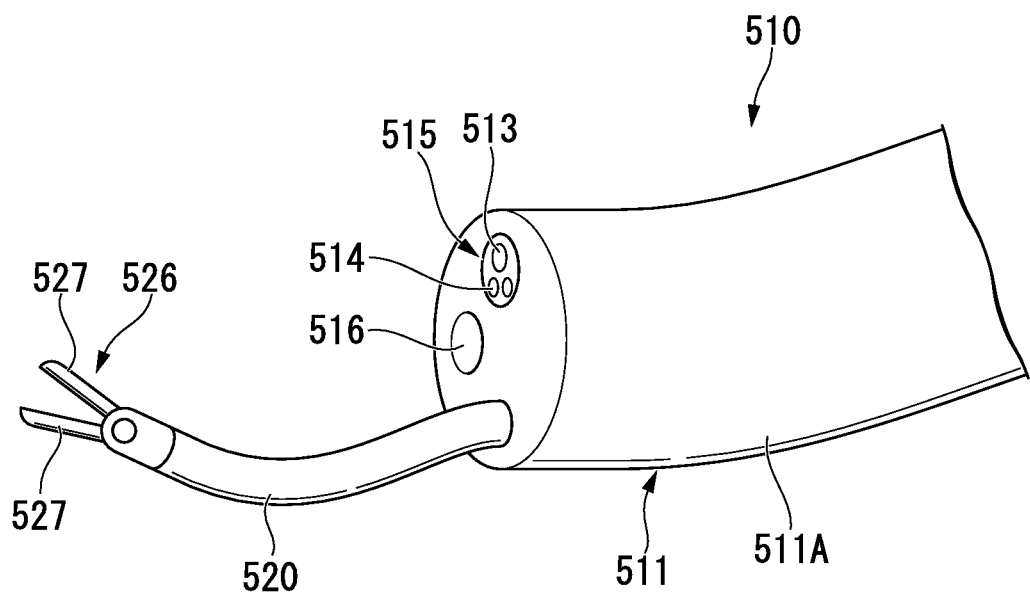
FIG. 34 is a view showing a distal portion of an endoscopic device in the medical manipulator.

In the medical manipulator of the present invention, a multi joint robot is not indispensable, and for example, a configuration in which an assistant (not shown) holds the endoscopic device 510 may be adopted. FIG. 34 is a perspective view showing the distal portion of the endoscopic device 510 inserted into the body of the patient P. As shown in FIG. 34, the endoscopic device 510 has a tubular member 511 (insertion section) having flexibility, and a holding tool 520 is attached to a distal end of the tubular member 511.

The tubular member 511 is a longitudinal member inserted into the body of the patient P. The tubular member 511 has a well-known bending mechanism 511A including joint rings, bending pieces, or the like, and can change the orientation of its distal portion by bending the bending mechanism 511A with an operation input to the master arm 503.

Additionally, the tubular member 511 is provided with an instrument channel 516 that is a path for delivering an instrument, and an observation unit 515. The instrument channel 516 opens to the distal of the tubular member 511. The instrument channel 516 also opens to a proximal end portion of the tubular member 511, and the opening is a delivery port 516a (refer to FIG. 32) for an instrument.

The observation unit 515, which is a device for observing a treatment target part, has a well-known configuration including an imaging mechanism 513 and an illumination mechanism 514. In the present embodiment, the observation unit 515 is fixed to the distal portion of the tubular member 511. However, the observation unit may be enabled to be advanced and retracted with respect to the tubular member or may be enabled to be bent, by using a well-known endoscope as the observation unit and inserting the endoscope through a channel for observation means provided in the tubular member.

The holding tool 520 is configured so as to be bendable by the operation of the master arm 503, and includes a gripper 526 (holder) attached to a distal portion thereof. The gripper 526 has a pair of gripper members 527 for gripping an instrument. The gripper members 527 are opened and closed by operating the knob part 802 of the master arm 503.

The holding tool 520 with the above configuration can perform a desired procedure by performing a bending operation while gripping an instrument with the gripper 526. Each holding tool 520 may be enabled to be housed inside the tubular member 511 so as to be advanceable and retractable with respect to the tubular member 511, or may be configured so as to be fixed to the distal portion of the tubular member 511 and so as not to be housed within the tubular member 511.

In the medical manipulator of the present invention, a specific structure that enables the holding tool 520 to be bent is not limited particularly. For example, the same mechanism as the above-described bending mechanism 511A may be adopted, or a configuration including one or more joint parts, and tubular parts that connect the joint parts or the joint parts and the gripper 526 may be adopted. Additionally, the number of the holding tools 520 may be one or more arbitrary numbers. The mechanisms for driving the joint parts or gripper or advancing and retracting the holding tool with respect to the tubular member are not limited particularly. For example, well-known mechanisms including an actuator, such as a motor, and a transmission member, such as a wire, which transmits a driving force, can be used.

Figure 35:
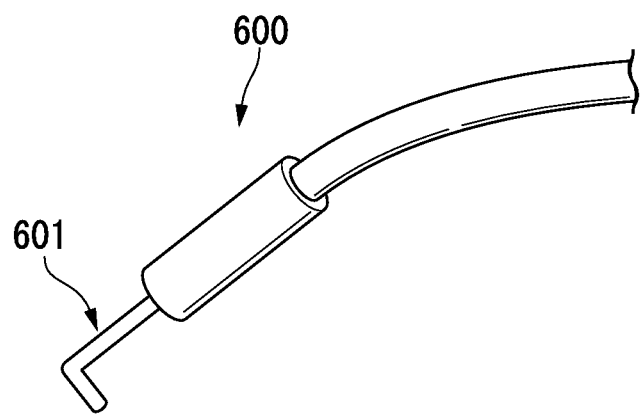
FIG. 35 is a view showing a distal portion of an instrument in the medical manipulator.

FIG. 35 is a view showing an instrument 600 inserted into the instrument channel 516. The instrument 600 has an end effector for performing a treatment at a distal portion thereof. The instrument 600 of FIG. 34 includes a hook knife 601 as the end effector. The hook knife 601 is electrically connected to a cable (not shown). The cable is connected to the multi-joint robot 508 through the inside of the instrument channel 516. The cable may be connected to another operating mechanism (not shown) for operating the hook knife 601. If an operation input is performed on the hook knife 601, application of an electric current from the multi joint robot 508 to the hook knife 601 is performed, and a treatment using the hook knife 601 is enabled.

Figure 36:
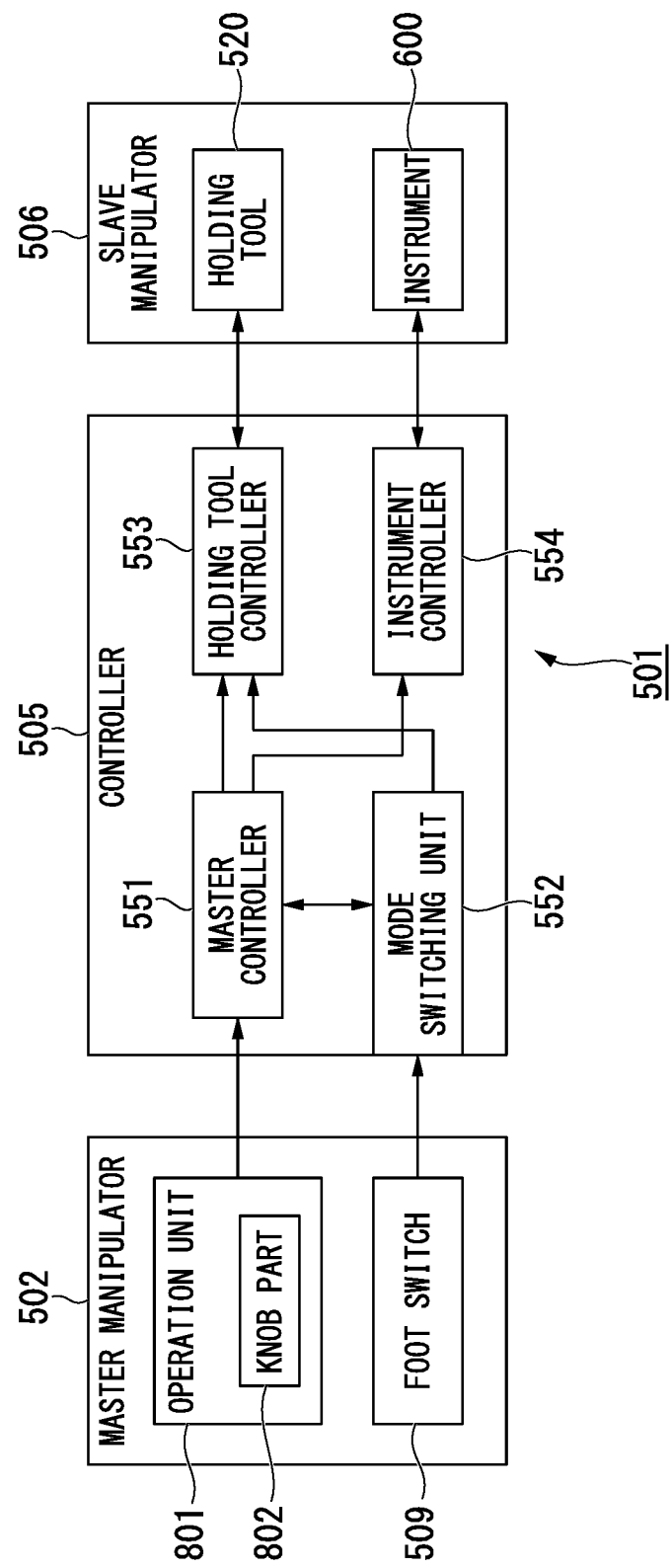
FIG. 36 is a functional block diagram of main portions of the medical manipulator.

FIG. 36 is a functional block diagram of main portions of the medical manipulator 501. The controller 505 includes a master input unit 551 that receives an operation input from the master manipulator 502, a mode-switching unit 552 that switches the operation mode of the medical manipulator 501, a holding tool controller 553 that generates an operating signal for the holding tool 520, and an instrument controller 554 that generates an operating signal for an instrument.

The master input unit 551 receives an operation input of the manipulator Op to the operation unit 801 and the knob part 802, and sends the received operation input to the holding tool controller 553 and the instrument controller 554 according to the operation mode.

The mode-switching unit 552 determines the operation mode on a switching input of the manipulator Op to a foot switch 509 (a mode-switching input unit, refer to FIG. 32) provided in the master manipulator 502, and transmits the switching input to the master input unit 551 and the holding tool controller 553. Although the present embodiment includes two types of a first mode and a second mode as the operation mode, the details thereof will be described below.

The holding tool controller 553 and the instrument controller 554 generate operating signals that drives the holding tool 520 and the instrument 600, respectively, on the basis of the operation input received from the master input unit 551, and transmit the operating signals to the slave manipulator 506.

The operation when the medical manipulator 501 with the above configuration is used will be described. First, an operator Op or an assistant inserts the distal portion of the tubular member 511 into the body of the patient P, and advances the distal portion to near a tissue on which a treatment is performed. Next, while checking an image of an operative field acquired by the observation unit 515 with the display unit 504, the operator Op operates the master arm 503 to operate the holding tool 520. The instrument 600 is inserted into the instrument channel 516 if necessary, and the instrument 600 protruding from the instrument channel 516 is held by the gripper 526 of the holding tool 520. A predetermined treatment is performed on a tissue by using the end effector of the held instrument 600.

The medical manipulator 501 includes two operation modes of the first mode and the second mode. The first mode is an operation mode when the holding tool 520 does not hold the instrument 600. In the first mode, according to well-known kinematics calculation or the like, the holding tool 520 is driven so that the position and orientation of gripper 526 correspond to the position and orientation of the operation unit 801, and the gripper 526 is opened and closed according to an operation input to the knob part 802.

The second mode is an operation mode when the gripper 526 of the holding tool 520 holds the instrument 600. In the second mode, the second mode is the same as the first mode in that the holding tool 520 is driven so that the position and orientation of gripper 526 correspond to the position and orientation of the operation unit 801, but the gripper 526 is locked in a state where the instrument 600 is held, and the end effector of the instrument 600 held according to the operation input to the knob part 802 is operated. That is, in the second mode, even if the knob part 802 is operated, the gripper 526 is not operated, but the knob part 802 functions as an operation input unit that operates the instrument.

Figure 37:
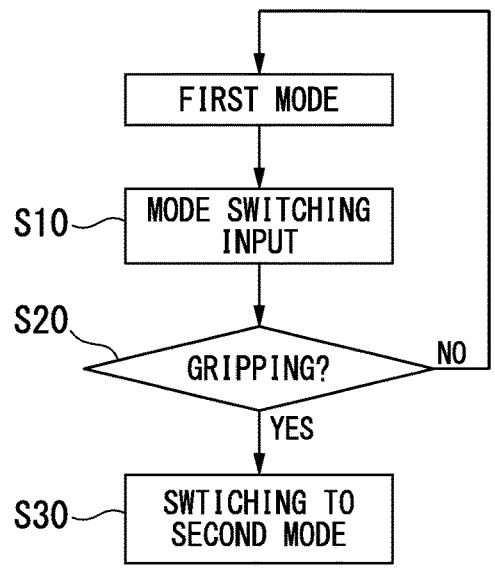
FIG. 37 is a flowchart showing a flow of switching from a first mode to a second mode in the medical manipulator.

FIG. 37 is a flowchart showing the flow of switching from the first mode to the second mode in the medical manipulator 501. First, in Step S10, the operator Op operates the foot switch 509 to perform a switching input for mode switching after the operator holds the instrument 600 with the gripper 526.

In Step S20, the mode-switching unit 552 determines whether or not the gripper 526 holds the instrument 600. In this determination, information to which the mode-switching unit 552 refers is not limited particularly. For example, a sensor that detects a gripping state or a gripped state may be provided in the gripper 526 or the instrument 600 and a determination can be made on the basis of the detection result of the sensor, or a determination can be made by analyzing the image of the gripper 526 acquired by the observation unit 515. The determination of Step S20 can be automatically performed by providing a holding-detecting mechanism that detects whether or not the holder as described above holds the instrument.

When the determination in Step S20 is No, the mode-switching unit 552 cancels the switching input and continues the first mode. At this time, recognition and addressing of the operator Op may be urged by displaying a message, such as "the instrument is not held", on the display unit 504 if necessary.

When the determination in Step S20 is Yes, the processing proceeds to Step S30. In Step S30, the mode-switching unit 552 switches the operation mode from the first mode to the second mode, and transmits the operation mode to the master input unit 551 and the holding tool controller 553. Accordingly, the mode operation of the medical manipulator 501 is switched to the second mode.

In the second mode, the master input unit 551 transmits the operation input to the knob part 802, to the instrument controller 554. The holding tool controller 553 generates an operating signal on the basis of the operation input received from the master input unit 551. At this time, the operating signal is generated so as to maintain a state where the gripper 526 holds the instrument 600 irrespective of the operation input to the knob part 802. The instrument controller 554 generates an operating signal that operates the end effector on the basis of the operation input to the knob part 802 received from the master input unit 551, and sends the operating signal to the instrument 600.

Figure 38:
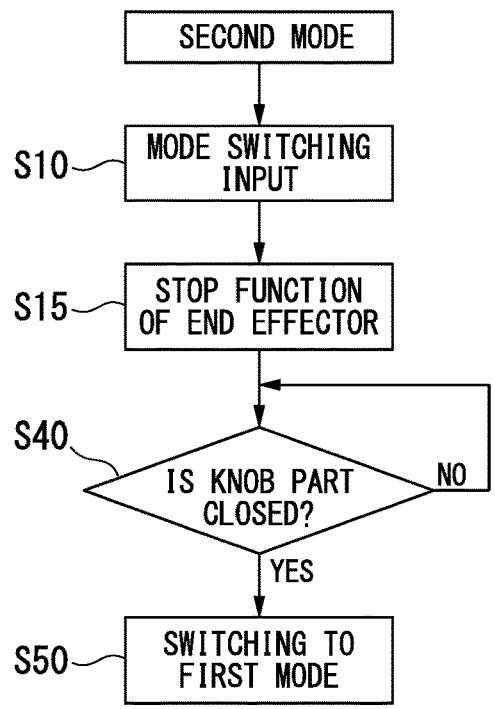
FIG. 38 is a flowchart showing a flow of switching from the second mode to the first mode in the medical manipulator.

FIG. 38 is a flowchart showing the flow of switching from the second mode to the first mode in the medical manipulator 501. In this flowchart, the function of the end effector is stopped in Step S15 after Step S10. Additionally, determination of Step S40 is performed instead of the determination of Step S20. In Step S40, the mode-switching unit 552 determines whether or not the knob part 802 is closed on the basis of the operation input received by the master input unit 551. When the determination in Step S40 is No, the mode-switching unit 552 repeats the determination at predetermined intervals. The operator Op is urged to close the knob part, using a message or the like if necessary. When the determination in Step S40 is Yes, the processing proceeds to Step S50 where the operation mode is switched to the first mode. By performing the determination of Step S40, it is possible to prevent a situation where the gripper 526 is opened unintentionally and the instrument 600 drops out of the holding tool 520.

According to the medical manipulator 501 of the present embodiment, the controller 505 has the mode-switching unit 552 that switches between the first mode and the second mode, and can perform a switching input from the foot switch 509 to thereby switch the operation mode. As a result, by switching the operation mode to the second mode when the instrument 600 is held by the gripper 526 of the holding tool 520, the end effector of the instrument 600 can be operated by the knob part of the operation unit 801 gripped by the operator Op. That is, since the operator Op may operate only the operation unit 801 and the knob part 802 even when the instrument 600 is held by the holding tool 520, the operation when a treatment is performed can be markedly simplified.

In the present embodiment, the mode-switching input unit is not limited to the foot switch, and can take various aspects. For example, the knob part 802 may be provided with a switch for mode switching. In this case, if a switch, such as a slide type or a toggle type, is used, this is preferable because the operator Op can intuitively recognize the present operation mode from the orientation or position of the switch. Additionally, a configuration may be adopted in which a switching input is performed by displaying the switch for switching on the display unit 504 and moving the gripper 526 to the position of the switch on the screen of the display unit 504. In addition, a configuration may be adopted in which the operator Op performs a switching input with voice or a predetermined operation (for example, operating the holding tool so that the holder draws a circle) of the holding tool. In these cases, a mechanism that recognizes a voice input, an image-processing mechanism that recognizes a predetermined operation, or the like function as the mode-switching input unit.

Figure 39:
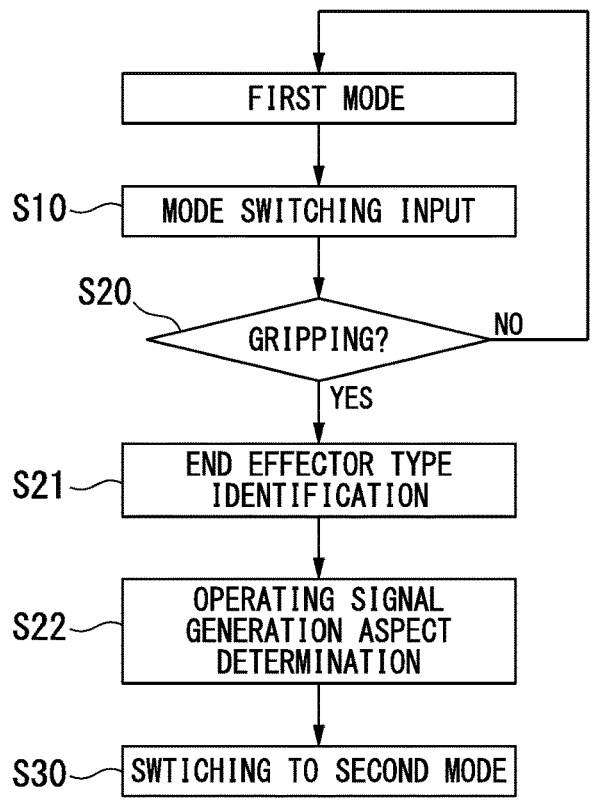
FIG. 39 is a flowchart showing a modification example of the flow of switching from the first mode to the second mode in the medical manipulator.

Additionally, when the medical manipulator of the present embodiment is configured so that a plurality of instruments can be used, a processing flow in mode switching may be as shown in FIG. 39. In the flowchart of a modification example shown in FIG. 39, when the determination of Step S20 is Yes, the processing proceeds to Step S21 and the type of the end effector of the instrument that the gripper 526 is gripping is recognized. Subsequently, in Step S22, the instrument controller 554 determines the generation aspect (for example, a part or function that operates according to the operation input to the knob part, whether or not the operating signal is digital or analog, the correspondence relationship between an operation input value and an operating signal value, or the like) of the operating signal, on the basis of the type of the end effector identified in Step S21. Thereafter, the processing proceeds to Step S30 where the operation mode is switched to the second mode.

Figure 40:
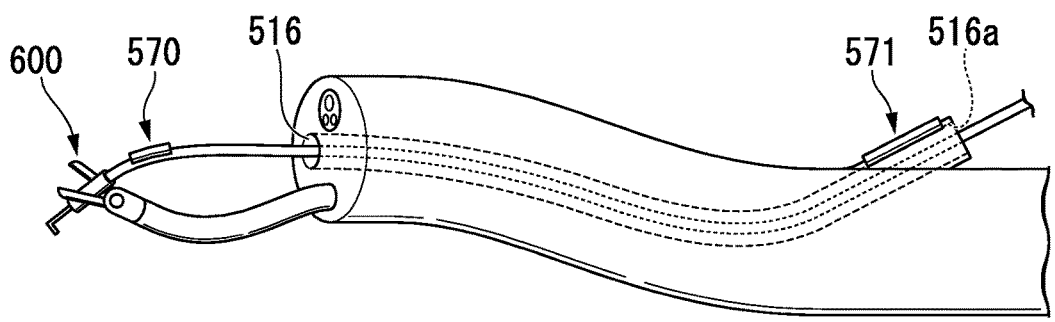
FIG. 40 is a view showing a configuration example for automatically identifying the type of an end effector.

In this modification example, the specific method of type recognition of the end effector in Step S21 is not limited particularly. If an example is taken, as shown in FIG. 40, identification information 570, such as a bar code or an RFID tag, may be attached to the instrument 600, and the delivery port 516a may be provided with an identification unit 571 that can read the identification information 570. By doing so, when the instrument 600 is inserted into the instrument channel 516 from the delivery port 516a, identification can be automatically performed. In addition, the type recognition may be performed by recognizing the shape or color of the end effector, the marker provided for identification from an image acquired by the observation unit 515. Moreover, the gripper 526 may be provided with a sensor, and the type recognition of the end effector of the instrument gripped may be performed using the sensor. Other well-known recognition methods may be used. In addition, such type of recognition can also be applied to a case where only one instrument is used, and there is a merit that input of the type of the end effector by the operator can be omitted.

Additionally, Step S20 where it is determined whether or not the holding tool holds the instrument may be omitted. In this case, the operator may determine in advance whether or not the mode switching may be performed immediately after a switching input and perform a switching input after checking that there is no problem.

Tenth Embodiment

A tenth embodiment of the present invention will be described. The difference between the medical manipulator of the present embodiment and the medical manipulator of the ninth embodiment is that the first mode and the second mode are different from each other in terms of the control of position and orientation on the slave manipulator side. In addition, in the following description, components common to those already described will be designated by the same reference numerals, and duplicate description will be omitted.

FIG. 41 is a view showing a difference in control between the first mode and the second mode in the medical manipulator of the present embodiment. In the first mode of the present embodiment, similar to the ninth embodiment, the holding tool 520 is driven so that the position and orientation of the gripper 526 of the holding tool 520 correspond to the position and an orientation of the operation unit 801. That is, the gripper 526 is a target part Ps in the control of position and orientation. On the other hand, in the second mode, the hook knife (end effector) 601 of the instrument 600 held by the gripper 526 serves as the target part Ps. Accordingly, the holding tool 520 is driven so that the position and orientation of the hook knife 601 correspond to the position and orientation of the operation unit 801.

Figure 42:
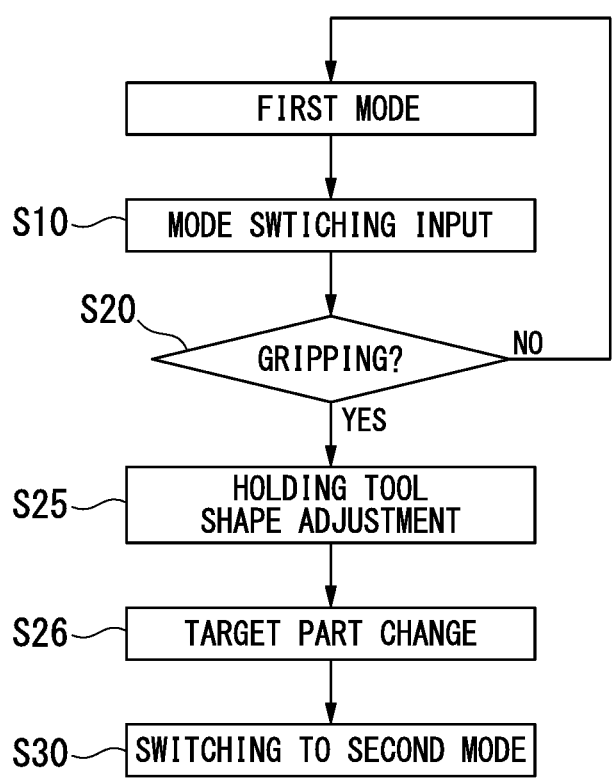
FIG. 42 is a flowchart showing a flow of switching from the first mode to the second mode in the medical manipulator.

FIG. 42 is a flowchart showing the flow of switching from the first mode to the second mode in the medical manipulator of the present embodiment. In this embodiment, if the determination in Step S20 is Yes, the processing proceeds to Step S25. In Step S25, the mode-switching unit 552 sends a command to the holding tool controller 553 so that the orientation of the gripper 526 is adjusted. The holding tool controller 553 that has received the command generates an operating signal that drives the holding tool 520 so that the orientation of the hook knife 601 and the orientation of the operation unit 801 match each other on the basis of the orientation of the hook knife 601 and the orientation of the operation unit 801 at this time. If this operating signal is transmitted to the slave manipulator 506, the respective parts of the holding tool 520 are driven, the overall shape of the holding tool 520 is adjusted, and the orientation of the hook knife 601 and the operation unit 801 match each other. During Step S25, the operation unit 801 is locked so that the operator Op cannot be moved. An example of changes in the shape of the holding tool before and after Step S25 is shown in FIG. 43. Since the target part Ps is the gripper 526 in a state before Step S25 shown on the left side, the orientation of the gripper 526 and the orientation of the operation unit 801 match each other. In a state after Step S25 shown on the right side, as the holding tool 520 is driven, the orientation of the hook knife 601 changes, and has almost the same orientation as the right gripper 526. Since the operation unit 801 is locked during this time, the orientation of the hook knife 601 and the orientation of the operation unit 801 substantially match each other.

In the subsequent Step S26, the target part Ps is changed from gripper 526 to the hook knife 601, and the position of the hook knife 601 and the position of the operation unit 801 at this time are matched with each other. Thereafter, the processing proceeds to Step S30 where the operation mode is switched to the second mode.

According to the present embodiment, in the second mode, the target part that becomes a reference for position orientation control is changed to the hook knife 601. Therefore, the operator Op can perform a treatment with a feeling that the hook knife and his/her own fingertip match each other, and a more intuitive operation is realized.

In the above-described example, the holding tool is driven so that the orientation of the end effector (hook knife) is coincident with the orientation of the operating part. However, the method of causing the orientation of the end effector and the orientation of the operating part to match each other is not limited to this. For example, if the movable part of the master arm 503 is provided with a drive mechanism, it is possible to drive the master arm 503 in a state that the holding tool and the instrument are locked, to thereby cause the orientation of the end effector and the orientation of the operating part to match each other.

Moreover, in a state where the holding tool and the instrument are locked, the operator Op can freely operate the respective parts of the master arm in that state, and a desired state is reached where it is easy for the operator Op himself to operate the orientation of the operating part. If the operator Op performs an input for association by the foot switch 509 or the like in this state, the medical manipulator may be configured so that the operation unit 801 and the hook knife 601 are associated with each other. In this case, although the orientation of the end effector and the orientation of the operating part do not necessarily match each other, since these orientations can be reflected, each operator's favorable condition, the sense of operation for the operator is improved.

In the second mode of the present embodiment, the end effector of the instrument held by the holding tool and the operating part are associated with each other. Therefore, when the instrument is held by the holding tool, it is preferable that the relative positional relationship between the holder and the end effector be determined uniquely. In the following, a configuration example for realizing such conditions will be described.

Figure 44:
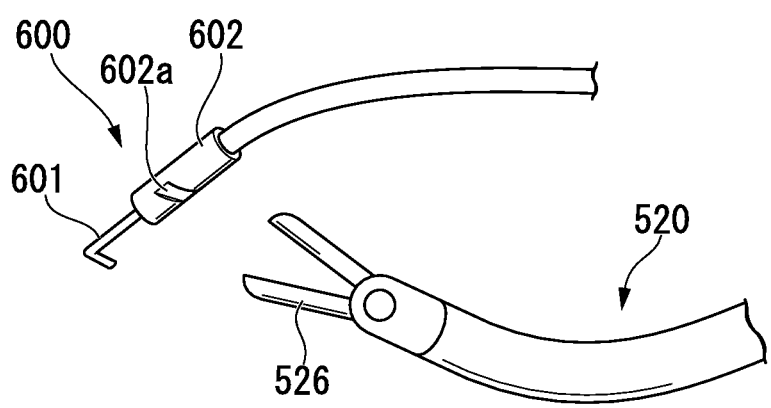
FIG. 44 is a view showing a configuration example for uniquely defining a holding aspect of the instrument by the holder.
Figure 45:
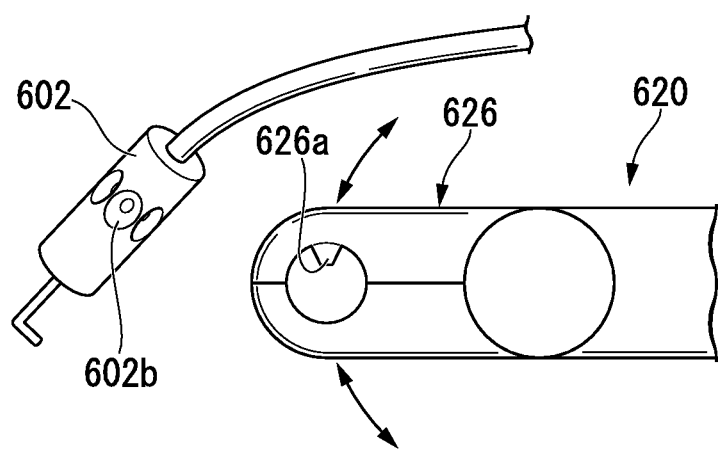
FIG. 45 is a view showing a configuration example for uniquely defining a holding aspect of the instrument by the holder.
Figure 46:
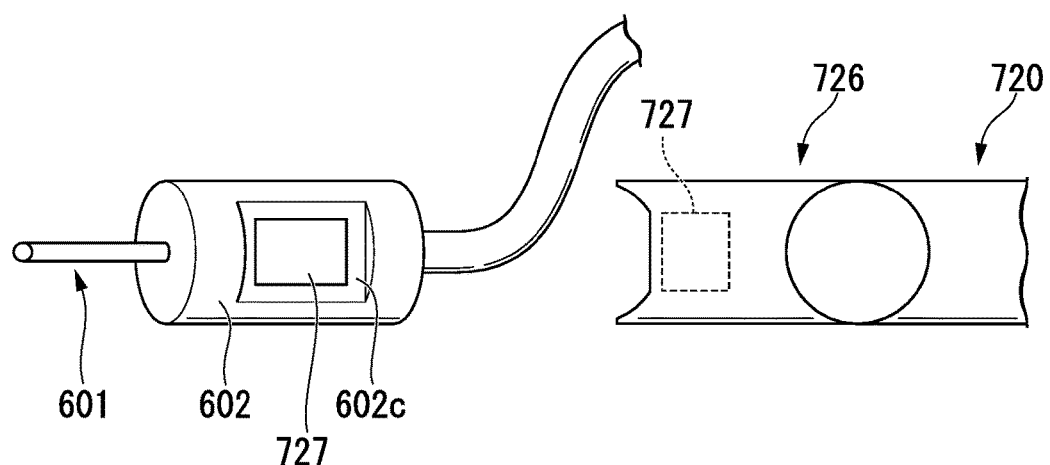
FIG. 46 is a view showing a configuration example for uniquely defining a holding aspect of the instrument by the holder.

In an example shown in FIG. 44, a supporting portion 602 of the instrument 600 to which the hook knife 601 is attached is provided with a groove 602*a* capable of housing the gripper 526. Accordingly, the relative positional relationship between the gripper 526 and the end effector (hook knife) can be determined substantially uniquely by holding the instrument 600 with the holding tool 520 so that gripper 526 enters the groove 602*a*. The same effect can be obtained even if the supporting portion 602 is provided with a concave portion 602*b* as shown in FIG. 45 instead of the groove, and the holding tool 620 is provided with a gripper 626 having a convex portion 626*a* engageable with the concave portion 602*b*. Holding may be made easy by a plurality of the grooves provided and the concave portions as shown in FIG. 45. Additionally, a configuration may be adopted in which a treatment can be performed with the instrument being held in a relative positional relationship suitable for treatment contents or the like by changing the relative positional relationship between the holder and the end effector for every plurality of grooves or concave portions. Moreover, as shown in FIG. 46, a configuration may be adopted in which magnets 727 are provided in the concave portion 602*c* and a holder 726 of a holding tool 720, respectively, so that holding is performed by a magnetic force and the relative positional relationship is determined uniquely.

Figure 47:
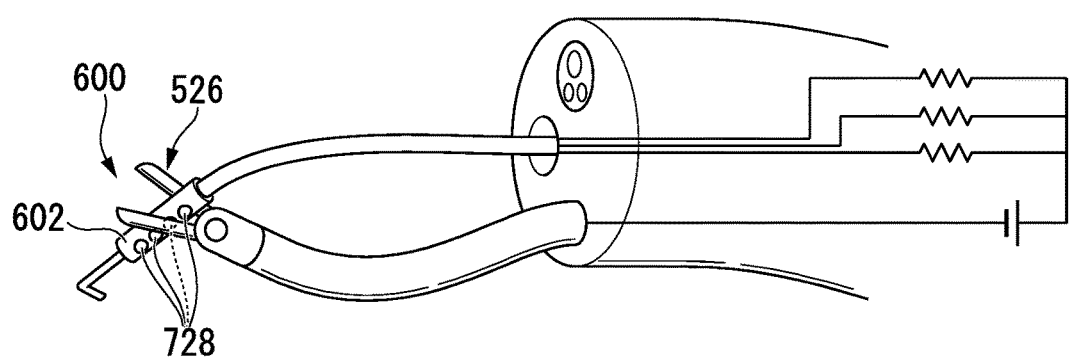
FIG. 47 is a view showing a configuration example in which a position held by the holder in the instrument is capable of being specified.

In the case of a holding aspect in which the relative positional relationship between the holding tool and the end effector is not determined uniquely, a configuration may be adopted in which a holding position that is a position where the holding tool holds the instrument and the position and orientation of the end effector can be detected. In an example shown in FIG. 47, the supporting portion 602 of the instrument 600 is provided with a plurality of contacts 728 that can be held by the gripper 526. By holding the contacts 728 with the metallic gripper 526, an electric current is applied to any one of detecting circuits connected to the contacts 728, respectively, and a contact held by gripper 526 can be specified.

Figure 48:
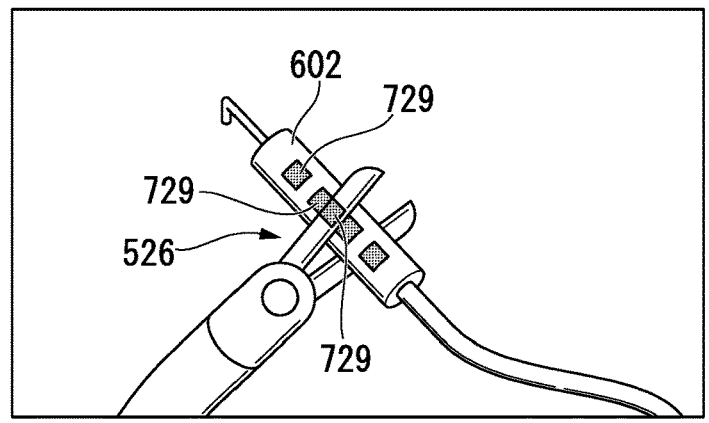
FIG. 48 is a view showing a configuration example in which a position held by the holder in the instrument is capable of being specified.

In an example shown in FIG. 48, the supporting portion 602 and the gripper 526 are provided with markers 729 with the same color. Since a marker seemingly becomes large at a holding position, the holding position can be specified using an image acquired by the observation unit 515.

The position and orientation of the end effector can be specified by using a 3D camera as the observation unit and detecting the distance from the specified holding position to the distal of the end effector, and vectors.

Moreover, although being slightly different from the purport of the present embodiment, when the operator Op has performed an input for correlation, the mode-switching unit may determine whether the orientation of the operating part is closer to any of the holder and the end effector, and may perform a switching to the first mode when closer to the holder, and may perform a switching to the end effector when closer to the second mode.

While the present invention has been described above using the respective embodiments, the technical scope of the present invention is not limited to the above embodiments. Combinations of constituent elements can be changed, various alternations can be added to respective constituent elements, or omissions can be made, without departing from the concept of the present invention.

Figure 49:
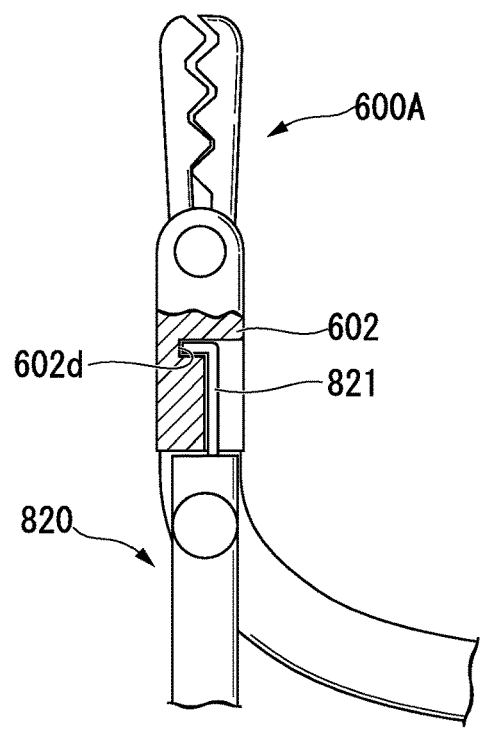
FIG. 49 is a view showing another example of holding of the instrument by the holder.
Figure 50:
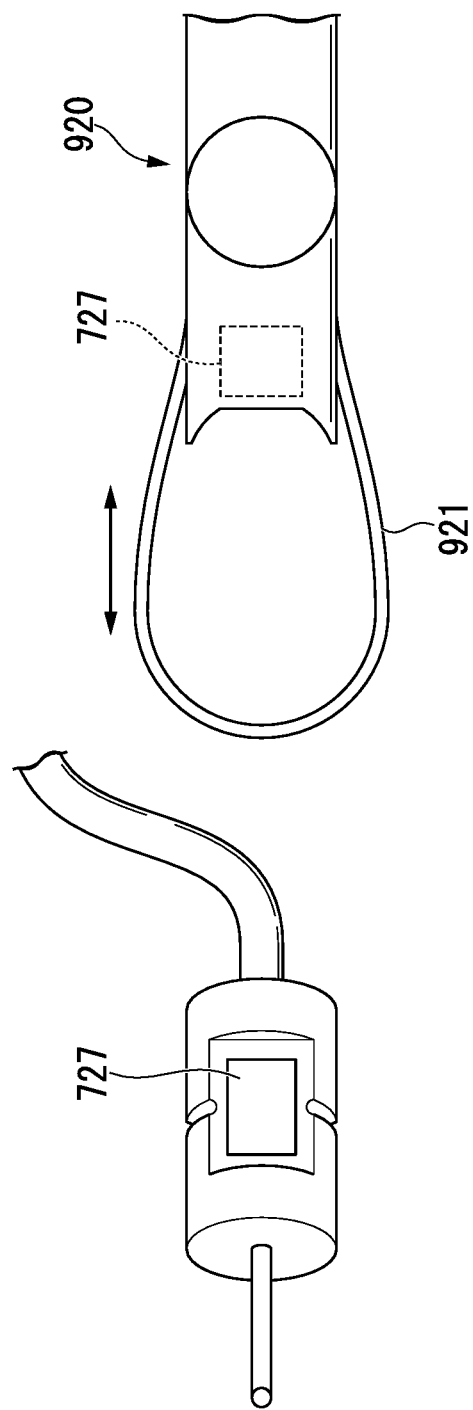
FIG. 50 is a view showing still another example of holding of the instrument by the holder.

First, in the medical manipulator of the present invention, an aspect in which an instrument is held is not limited to the above-described gripping using the gripper. For example, as shown in FIG. 49, a distal portion of a holding tool 820 is a hook knife 821, and an instrument 600A may be held by engaging the hook knife 821 with an engaged portion, such as a groove 602*d* provided in the supporting portion 602 of an instrument 600A. In this case, the hook knife 821 functions as the holder. Additionally, an example shown in FIG. 50 provides a configuration in which a distal portion of a holding tool 920 is a snare loop 921 and the instrument 600 is held by using the snare loop 921 and a magnet 727 as the holder. In addition, the specific aspect of the holder for holding the instrument is not limited particularly.

Additionally, the instruments used in the above respective embodiments are not limited to those used by applying an electric current to the end effectors, such as a hook knife, and may be those exhibiting predetermined functions with an operation input. For example, there may be an instrument that has a needle or a tube as the end effector and performs liquid delivery or suction with an operation input, and an instrument that has a pair of forceps members opening and closing as the end effector and opens and closes the forceps members with an operation input.

In the medical manipulator of the present invention, some of the plurality of instruments to be used may not exhibit predetermined functions with an operation input. In this case, a function may not be allocated to the knob part in the second mode, but the gripper may simply be brought into a locked state. Even in this way, since the operator may not need to continue closing the knob part while performing a treatment using the instrument, the operability is improved.

Figure 51A:
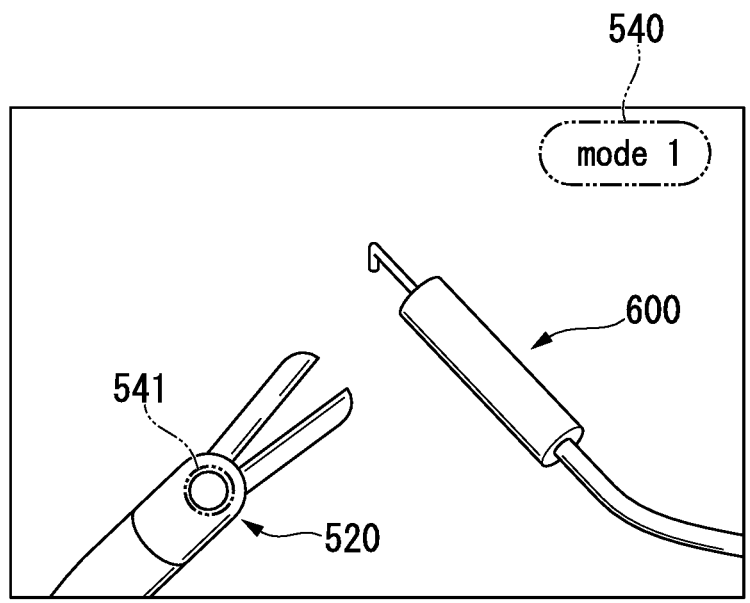
FIG. 51A is a view showing an example of a screen displayed on a display unit in a modification example of the present invention.
Figure 51B:
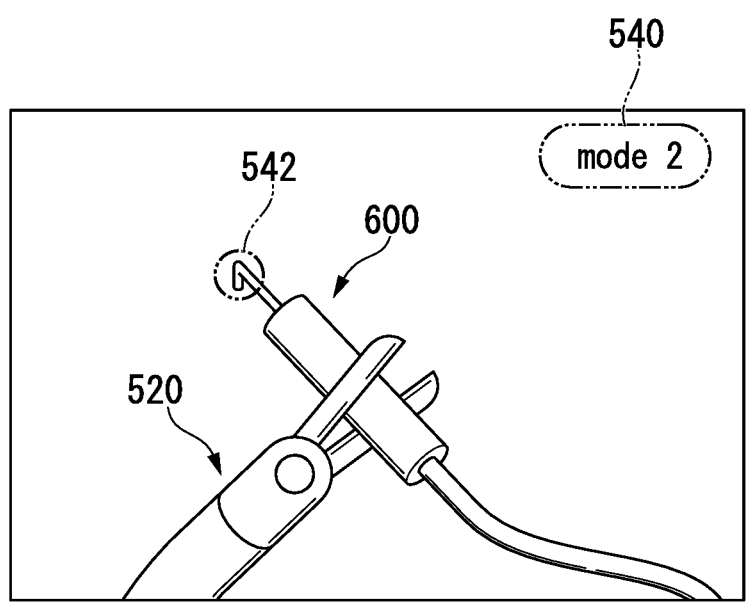
FIG. 51B is a view showing an example of a screen displayed on a display unit in a modification example of the present invention.

Additionally, as shown in FIGS. 51A and 51B, a display region 540 that displays an operation mode at that time may be provided on an image displayed on the display unit 504. Here, as in the tenth embodiment, when target parts are changed in the first mode and the second mode, the target parts in the respective modes may be displayed on the display unit 504 by markers 541 and 542 or the like.

Additionally, although only the example in which the medical manipulator includes the tubular member having flexibility has been described in the above-described respective embodiments, the medical manipulator of the present invention is not limited to this. Accordingly, a medical manipulator may be adopted in which a hole is made in the abdominal wall or the like and a robot arm is used after being inserted into the hole.

Additionally, although only the configuration example in which the slave manipulator and the master manipulator are arranged apart from each other and a remote operation is performed has been described in the above-described respective embodiments, the present invention is not limited to this, and components equivalent to both of the manipulators may be integral.

In addition, the present invention is not limited by the above description and is limited only by the scope of the appended claims.

Additionally, although the description has the same names but different Reference Signs in the first to tenth embodiments, and the relevant components are substantially the same.

The invention claimed is:

1. A manipulator system comprising:
a medical instrument configured to be inserted into a body;
a manipulator configured to hold a portion of the instrument positioned in the body;
a switch configured to detect whether or not the manipulator holds the portion of the instrument positioned in the body;
an instruction-receiving part configured to detect an instruction for operating the instrument; and
a controller comprising hardware, the controller being configured to operate the instrument based on the instruction from the instruction-receiving part only when the switch detects that the manipulator holds the portion of the instrument positioned in the body,
wherein the switch detects whether or not the manipulator holds the portion of the instrument positioned in the body according to a conduction state and a cutoff state between a pair of contacts,
the switch switches the conduction state and the cutoff state between the pair of contacts by being pressed in a reference direction,
the manipulator has a gripper that grips the switch in the reference direction,
the instrument comprises a first instrument and a second instrument, and the controller is configured to:
 operate only the first instrument where the instruction-receiving part detects the instruction when the switch detects whether or not the manipulator holds a portion of the first instrument positioned in the body, and
 operate only the second instrument where the instruction-receiving part detects the instruction when the switch detects whether or not the manipulator holds a portion of the second instrument positioned in the body.

2. A manipulator system comprising:
a medical instrument configured to be inserted into a body;
a manipulator configured to hold a portion of the instrument positioned in the body;
a switch configured to detect whether or not the manipulator holds the portion of the instrument positioned in the body;
an instruction-receiving part configured to detect an instruction for operating the instrument; and
a controller comprising hardware, the controller being configured to operate the instrument based on the instruction from the instruction-receiving part only when the switch detects that the manipulator holds the portion of the instrument positioned in the body,
wherein the switch detects whether or not the manipulator holds the portion of the instrument positioned in the body according to a conduction state and a cutoff state between a pair of contacts,
the switch switches the conduction state and the cutoff state between the pair of contacts by being pressed in a reference direction,
the manipulator has a gripper that grips the switch in the reference direction,
the switch comprises a first switch that switches a first conduction state and first cutoff state between a pair of first contacts, and a second switch that switches a second conduction state and a second cutoff state between a pair of second contacts,
the instrument is provided with the first switch and the second switch, and
the controller is configured to:
 operate the instrument to perform a first operation where the instruction-receiving part detects the instruction when the first conduction state or the first cutoff state is detected between the pair of first contacts, and
 operate the instrument to perform a second operation different from the first operation in a case where the instruction-receiving part detects the instruction when the second conduction state or the second cutoff state is detected between the pair of second contacts.

* * * * *